(12) United States Patent
Liu et al.

(10) Patent No.: US 10,975,082 B2
(45) Date of Patent: Apr. 13, 2021

(54) INHIBITOR OF FLT3 KINASE AND USE THEREOF

(71) Applicant: PRECEDO PHARMACEUTICALS CO., LTD, Anhui (CN)

(72) Inventors: Qingsong Liu, Anhui (CN); Jing Liu, Anhui (CN); Xixiang Li, Anhui (CN); Aoli Wang, Anhui (CN); Ziping Qi, Anhui (CN); Hong Wu, Anhui (CN); Jiaxin Wu, Anhui (CN); Wenchao Wang, Anhui (CN); Chen Hu, Anhui (CN); Cheng Chen, Anhui (CN); Li Wang, Anhui (CN); Beilei Wang, Anhui (CN)

(73) Assignee: PRECEDO PHARMACEUTICALS CO., LTD, Anhui (CN)

(*) Notice: Subject to any disclaimer, the term of this patent is extended or adjusted under 35 U.S.C. 154(b) by 31 days.

(21) Appl. No.: 16/306,647

(22) PCT Filed: Jun. 5, 2017

(86) PCT No.: PCT/CN2017/087159
§ 371 (c)(1),
(2) Date: Dec. 3, 2018

(87) PCT Pub. No.: WO2017/206962
PCT Pub. Date: Dec. 7, 2017

(65) Prior Publication Data
US 2020/0010471 A1   Jan. 9, 2020

(30) Foreign Application Priority Data
Jun. 3, 2016  (CN) .......................... 201610409235.5

(51) Int. Cl.
*C07D 487/04* (2006.01)
*A61P 35/02* (2006.01)
*A61K 45/06* (2006.01)

(52) U.S. Cl.
CPC ............ *C07D 487/04* (2013.01); *A61P 35/02* (2018.01); *A61K 45/06* (2013.01)

(58) Field of Classification Search
CPC ............................ A61K 31/519; C07D 487/04
USPC ........................................ 514/262.1; 544/262
See application file for complete search history.

(56) References Cited

FOREIGN PATENT DOCUMENTS

| WO | WO 2014/015673 A1 | 1/2014 |
| WO | WO 2014/017659 A1 | 1/2014 |
| WO | WO 2015/043492 A1 | 4/2015 |

OTHER PUBLICATIONS

International Search Report dated Sep. 11, 2017 issued in PCT/CN2017/087159.
European Supplementary Search Report dated Dec. 10, 2019 received in European Application No. 17 80 5907.7.
Li X. et al., "Discovery of (R)-1-(3-(4-Amino-3-(4-Phenoxyphenyl)-1H-Pyrazolo[3,4-d]Pyridmidin-1-yl)Piperidin-1-yl)-2-(Dimethylamino)Ethanone (CHMFL-FLT3-122) as a Potent and Orally Available FLT3 Kinase Inhibitor for FLT3-ITD Positive Acute Myeloid Leukemia", Journal of Medicinal Chemistry 58:9625-9638 (2015).

*Primary Examiner* — Jeffrey H Murray
(74) *Attorney, Agent, or Firm* — Scully, Scott, Murphy & Presser, P.C.

(57) ABSTRACT

The present invention provides a novel inhibitor of FLT3 kinase, comprising a compound of formula (I) or a pharmaceutically acceptable salt, solvate, isomer, ester, acid, metabolite or prodrug thereof. The present invention also provides a pharmaceutical composition comprising the compound of formula (I), as well as the use and method for preventing or treating FLT3-related conditions, especially conditions related to mutant FLT3 kinase (particularly, FLT3/ITD mutant kinase).

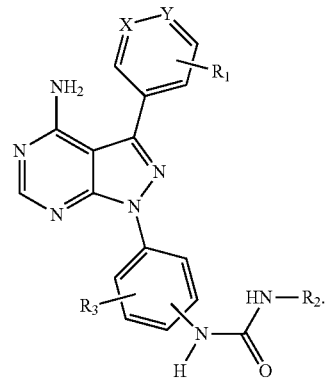

Formula (I)

14 Claims, 4 Drawing Sheets a b c

INHIBITOR OF FLT3 KINASE AND USE THEREOF

TECHNICAL FIELD

The present invention relates to compounds used as novel inhibitors of FLT3 kinase, pharmaceutical compositions comprising the compounds, as well as uses and methods for using these compounds and compositions to reduce or inhibit the activity of wild-type FLT3 kinase and/or mutant FLT3 kinase in a cell or a subject, and uses and methods of these compounds and compositions for preventing or treating FLT3-related conditions in a subject.

BACKGROUND OF THE INVENTION

Protein kinases are enzymatic components of the signal transduction pathways which catalyze the transfer of the terminal phosphate from ATP to the hydroxy group of tyrosine, serine and/or threonine residues of proteins. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. Therefore, inhibitors of protein kinases have particular utility in the treatment of human and animal disease.

FLT3 (Fms-like tyrosine kinase 3), together with c-Kit, c-FMS and PDGFR, belongs to members of receptor tyrosine kinase III (RTK III) family, the protein structure of which include an extracellular region consisting of five immunoglobulin (Ig)-like domains, a transmembrane region, an intracellular juxtamembrane (JM) region, as well as two tyrosine kinase (TK) domains interrupted by a kinase insert in the intracellular region (S. D. Lyman et al., *Oncogene*, 1993, 8, 815-822). In 1996, the FLT3 mutations were first identified in acute myelocytic leukemia (AML) cells, and the mutation type was internal tandem duplications (FLT3/ITD). In recent years, many studies have demonstrated that the FLT3-actived mutations play a very important pathological role in the development of AML and the progression of the disease. AML patients with the FLT3/ITD-actived mutations normally have unique clinical features, such as high peripheral blood leucocyte count, poor clinical prognosis, and easy relapse, and the like. As the method for detecting the FLT3-actived mutations is simple and practicable, more and more researchers are committed to developing FLT3 as a conventional detection means of AML for guiding the therapy and prognostic prediction in AML patients, and as a detection means of minimal residual leukemia, and as a new target for chemotherapy in leukemia patients.

Hematological malignancies are cancers of the body's blood forming and immune systems, the bone marrow and lymphatic tissues. Whereas in normal bone marrow, FLT3 expression is restricted to early progenitor cells, in hematological malignancies, FLT3 is expressed at high levels or FLT3 mutations cause an uncontrolled induction of the FLT3 receptor and downstream molecular pathway, possibly Ras activation. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), adult T-cell ALL, AML with trilineage myelodysplasia (AML/TMDS), mixed lineage leukemia (MLL), myelodysplasia syndromes (MDSs), myeloproliferative disorders (MPD), multiple myeloma (MM) and myeloid sarcoma (Kottaridis, P. D., R. E. Gale et al., FLT3 mutations and leukaemia, British Journal of Haematology, 2003, 122(4):523-38; Ansari-Lari, Ali et al., FLT3 mutations in myeloid sarcoma, British Journal of Haematology, 2004, 126(6):785-91.).

It has been confirmed that there are mainly two classes of FLT3-actived mutations: Internal tandem duplications (ITD) and point mutation in the activation loop (PM point mutation). Both classes of FLT3-actived mutations can cause spontaneous phosphorylation of FLT3, which leads to ligand-independent constitutive activation of FLT3, which further activates its downstream abnormal signal transduction, thereby acing to promote proliferation and inhibit apoptosis, so that the leukemia patients with the mutant phenotype have poor clinical prognosis.

Currently targeted inhibition of wild-type FLT3 and mutant FLT3 has become a research focus, mainly on developing small-molecule tyrosine kinase inhibitors, which inhibit the kinase activity by competing with FLT3 tyrosine kinase for ATP binding sites. Inhibitors of FLT3 kinase, such as AC220, have now been introduced into clinical practice. However, some patients (such as AML patients) who have been treated with existing drugs are found to be resistant to the drugs at a later stage of treatment. Studies have shown that this type of resistance is caused by the high expression of the ligand FL (FLT3 Ligand) co-expressed with FLT3.

SUMMARY OF THE INVENTION

The present invention provides a novel inhibitor of FLT3 kinase, which comprises a compound of Formula (I) or a pharmaceutically acceptable salt, solvate, isomer, ester, acid, metabolite or prodrug thereof:

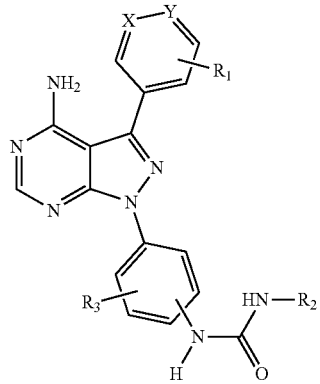

Formula (I)

wherein, at least one of X and Y is C, and the other is selected from the group consisting of C and N;

$R_1$ is selected from the group consisting of hydrogen, halogen, $C_{1-8}$ alkyl, $C_{1-8}$ haloalkyl, $C_{1-8}$ alkoxy, $C_{1-8}$ alkylamino, $C_{1-8}$ haloalkoxy, $C_{1-8}$ aminoalkyl, $C_{1-8}$ aminoalkoxy, $C_{1-8}$ alkylamino $C_{1-8}$ alkoxy, quaternary ammonium $C_{1-8}$ alkoxy, $C_{1-8}$ alkanoyl $C_{1-8}$ alkyl, arylcarbonyl $C_{1-8}$ alkyl, $C_{1-8}$ alkanoyl $C_{1-8}$ alkoxy, arylcarbonyl $C_{1-8}$ alkoxy, aminosulfonyl, $C_{1-8}$ alkylaminosulfonyl, $C_{3-6}$ heterocycloalkyl, aminoacyl, $C_{1-8}$ alkylaminocarbonyl, $C_{3-6}$ heterocycloalkylcarbonyl, $C_{3-6}$ cycloalkyl, $C_{1-8}$ alkyl($C_{3-6}$ heterocycloalkyl), $C_{1-8}$ alkoxy($C_{3-6}$ heterocycloalkyl), $C_{3-6}$ heterocycloalkylcarbonyl $C_{1-8}$ alkyl, aryloxy, $C_{1-8}$ alkylsulfonyl, $C_{1-8}$ alkylsulfonylamino, $C_{3-6}$ cycloalkylsulfonylamino, $C_{3-6}$ heterocycloalkylaminocarbonyl, acylamino($C_{1-8}$ alkylamino $C_{1-8}$ alkyl), and $C_{1-8}$ alkylamino ($C_{1-8}$ alkylamino), wherein aryl and heterocycloalkyl are optionally substituted with 1-3 independent $R_4$;

$R_2$ is selected from the group consisting of $C_{1-8}$ alkyl, $C_{1-8}$ haloalkyl, $C_{1-8}$ alkylamino $C_{1-8}$ alkyl, aryl and heteroaryl, wherein aryl and heteroaryl are optionally substituted with 1-3 independent $R_4$;

$R_3$ is selected from the group consisting of hydrogen, halogen, $C_{1-8}$ alkyl and $C_{1-8}$ haloalkyl;

$R_4$ is independently selected from the group consisting of halogen, $C_{1-8}$ alkyl, $C_{1-8}$ alkoxy, $C_{1-8}$ haloalkyl, $C_{1-8}$ hydroxylalkyl, $C_{1-8}$ aminoalkyl, $C_{1-8}$ alkanoyl, $C_{1-8}$ alkylsulfonyl, and aminoacyl.

In another aspect, the present invention provides a pharmaceutical composition which comprises a therapeutically effective amount of at least one compound of Formula (I) provided herein, or a pharmaceutically acceptable salt, solvate, isomer, ester, acid, metabolite or prodrug thereof, and a pharmaceutically acceptable carrier or excipient, and optionally other therapeutic agents.

In a further aspect, the present invention provides a method for preparing a compound of Formula (I) of the invention, or a pharmaceutically acceptable salt, solvate, isomer, ester, acid, metabolite or prodrug thereof.

In a further aspect, the present invention relates to use of a compound of formula (I), or a pharmaceutically acceptable salt, solvate, isomer, ester, acid, metabolite or prodrug thereof, for reducing or inhibiting the activity of wild-type FLT3 kinase and/or mutant FLT3 kinase in vivo or in vitro.

In a further aspect, the present invention relates to use of a compound of formula (I), or a pharmaceutically acceptable salt, solvate, isomer, ester, acid, metabolite or prodrug thereof, or a pharmaceutical composition comprising a compound of formula (I) for preparation of a medicament for treating FLT3-related conditions.

In particular, said conditions respond to inhibition of wild-type FLT3 kinase or mutant FLT3 kinase. FLT3 mutations include ITD mutations and point mutations, especially FLT3/ITD mutations.

DESCRIPTION OF THE FIGURES

FIG. 1 illustrates the effects of Compound 1 on signaling pathway upstream and downstream of FLT3 in three types of cells, wherein FIG. 1a, FIG. 1b and FIG. 1c show the results in cells MOLM-14, MOLM-13 and MV-4-11, respectively;

FIG. 2 illustrates the effects of Compound 1 on proteases that are closely related to cell apoptosis in three types of cells, wherein FIG. 1a, FIG. 1b and FIG. 1c show the results in cells MOLM-13, MV-4-11 and MOLM-14, respectively;

FIG. 4 illustrates the inhibitory effects of Compound 1 on tumors in nude mice models bearing subcutaneous tumors, wherein FIG. 4a is a curve showing the body weights of mice that vary with the dosing time; FIG. 4b is a curve showing the relative tumor size that varies with the dosing time; and FIG. 4c shows the tumor inhibition rate in groups with different dosing amounts.

DETAILED DESCRIPTION OF THE INVENTION

Terminology

Figure 1:
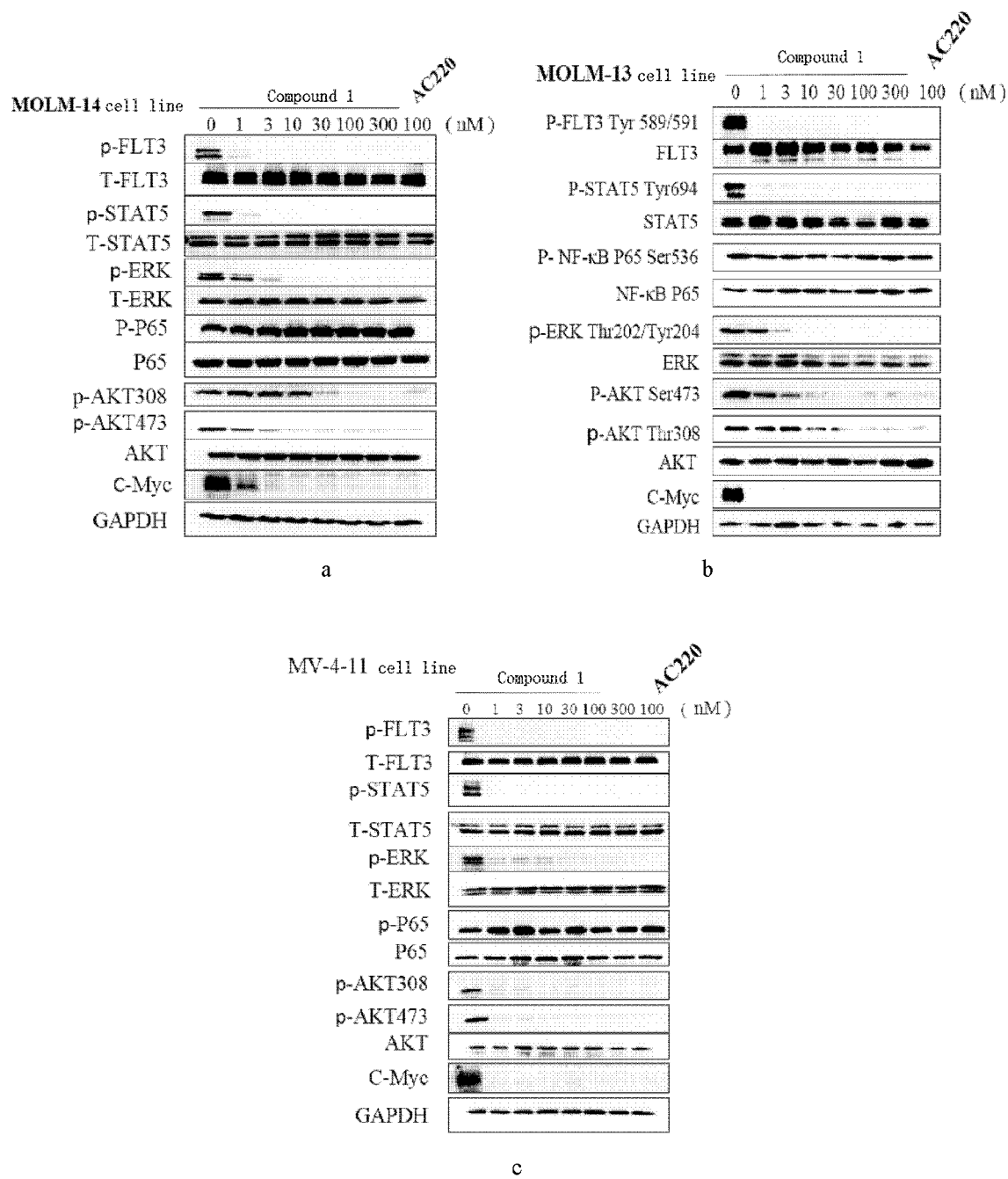

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferably an alkyl having 1 to 8 carbon atoms, more preferably a "lower alkyl" having 1 to 6 carbon atoms, and even more preferably an alkyl having 1 to 4 carbon atoms. Typical alkyl groups include, but are not limited to, methyl, ethyl, propyl, isopropyl, n-butyl, isobutyl, tertiary butyl, pentyl, hexyl, and the like. It should be understood that the "alkyl" as mentioned herein encompasses all configurations and conformations that may exist of the alkyl, e.g., the "butyl" as mentioned herein intends to encompass n-butyl, isobutyl, and tertiary butyl.

"Alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

"Alkoxyalkyl" refers to an alkyl radical, as defined herein, substituted with an alkoxy group, as defined herein.

As used herein, the term "cyano" refers to a group of formula —CN.

The term "sulfonyl" refers to —S(=O)$_2$. The term "aminosulfonyl" refers to —S(=O)$_2$—NH$_2$, and the term "alkylsulfonyl" or "sulfuryl" refers to —S(=O)$_2$—R, wherein R is alkyl.

The term "amino" refers to —NH$_2$. The term "aminoacyl" refers to —CO—NH$_2$. The term "acylamino" or "acylamido" refers to —NR—CO—R', wherein each of R and R' is independently hydrogen or alkyl.

The term "quaternary ammonium group" refers to —N$^+$RR'R'', wherein each of R, R' and R'' is independently selected from the group consisting of $C_{1-8}$ alkyl.

The term "alkylamino" refers to an amino substituent which is further substituted with one or two alkyl groups, specifically the group —NRR', wherein R and R' are each independently selected from the group consisting of the group consisting of hydrogen or lower alkyl, with the proviso that —NRR' is not —NH$_2$. The term "aralkylamino" as used herein refers to the group —NRR', wherein R is lower aralkyl, and R' is hydrogen, lower alkyl, aryl or lower aralkyl. The term "aminoalkyl" refers to an alkyl substituent which is further substituted with one or more amino groups. The term "aminoalkoxy" refers to an alkoxy substituent which is further substituted with one or more amino groups. The term "hydroxyalkyl" or "hydroxylalkyl" refers to an alkyl substituent which is further substituted with one or more hydroxyl groups. The term "cyanoalkyl" refers to an alkyl substituent which is further substituted with one or more cyano groups. The term "alkylcarbonyl" or "alkanoyl" refers to a carbonyl group which is further substituted with one alkyl group. The term "alkylcarbonylalkyl" or "alkanoylalkyl" refers to an alkyl group which is further substituted with an alkylcarbonyl group. The term "alkylcarbonylalkoxy" or "alkanoylalkoxy" refers to an alkoxy group which is further substituted with an alkylcarbonyl group. The term "alkoxycarbonyl" refers to a carbonyl group which is further substituted with an alkoxy group.

The term "alkylaminoalkyl" refers to an alkyl group, as defined herein, substituted with an alkylamino, as defined herein.

The term "alkylaminosulfonyl" refers to a sulfonyl group, as defined herein, substituted with alkylamino as defined herein.

The term "alkylaminocarbonyl" refers to a carbonyl group, as defined herein, substituted with alkylamino as defined herein.

The term "alkylsulfonylamino" or "cycloalkylsulfonylamino" refers to an amino group, as defined herein, substituted with alkylsulfonyl or cycloalkylsulfonyl as defined herein.

The term "aromatic" refers to a planar ring having a delocalized π-electron system containing 4n+2π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

"Alkyl(aryl)" or "aralkyl" means an alkyl radical, as defined herein, substituted with an aryl group, as defined herein. Non-limiting alkyl(aryl) groups include benzyl, phenethyl, and the like.

The term "arylcarbonyl" refers to a carbonyl group, as defined herein, substituted with an aryl group as defined herein.

The term "cycloalkyl" refers to a monocyclic or polycyclic radical that contains only carbon and hydrogen. Cycloalkyl groups include groups having from 3 to 8 ring atoms. Depending on the structure, a cycloalkyl group can be a monoradical or a diradical (e.g., a cycloalkylene group). In the present invention, the cycloalkyl group is preferably a cycloalkyl having 3 to 8 carbon atoms, and more preferably a "lower cycloalkyl" having 3 to 6 carbon atoms.

"Alkyl(cycloalkyl)" or "cycloalkylalkyl" means an alkyl radical, as defined herein, substituted with a cycloalkyl group, as defined herein. Non-limiting alkyl(cycloalkyl) groups include cyclopropylmethyl, cyclobutylmethyl, cyclopentylmethyl, cyclohexylmethyl, and the like.

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

The term "heteroaryl" refers to an aryl group that includes one or more ring heteroatoms selected from the group consisting of nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

As used herein, the term "heterocycloalkyl" or "heterocyclyl" refers to a non-aromatic ring wherein one or more atoms forming the ring is a heteroatom selected from the group consisting of the group consisting of nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heteroaryl)" or "heteroarylalkyl" means an alkyl radical, as defined herein, substituted with a heteroaryl group, as defined herein.

The term "alkyl(heterocycloalkyl)" or "heterocycloalkylalkyl" means an alkyl radical, as defined herein, substituted with a heterocycloalkyl group, as defined herein.

The term "heterocycloalkylcarbonyl" refers to a carbonyl group, as defined herein, substituted with heterocycloalkyl, as defined herein. The term "heterocycloalkylamino" refers to an amino group, as defined herein, substituted with heterocycloalkyl, as defined herein.

The term "halo" or "halogen" means fluoro, chloro, bromo and iodo.

The terms "haloalkyl", "haloalkoxy" and "haloheteroalkyl" include alkyl, alkoxy and heteroalkyl structures in which at least one hydrogen is replaced with a halogen atom. In certain embodiments in which two or more hydrogen atoms are replaced with halogen atoms, the halogen atoms are the same or different as one another.

The term "acyl" means a monovalent radical remaining in an organic or inorganic oxygen-containing acid that removes hydroxyl groups, with the general formula of R-M(O)—, wherein M is generally C.

The term "carbonyl" is an organic functional group (C=O) formed by carbon atom and oxygen atom through a double bond linkage.

The term "substituted" means that the referenced group may be substituted with one or more additional group(s) individually and independently selected from the group consisting of the group consisting of alkyl, cycloalkyl, aryl, heteroaryl, hydroxy, alkoxy, cyano, halo, amide, nitro, haloalkyl, amino, alkylcarbonyl, alkoxycarbonyl, alkyl(heteroaryl), alkyl(heterocycloalkyl), alkylsulfonyl, aminoacyl, and the like.

The terms "inhibits", "inhibiting", or "inhibitor" of a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics*, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The term "isomers" refers to compounds which have identical chemical constitution, but differ with regard to the arrangement of the atoms or groups in space, which is intended to include diastereoisomers, enantiomers, regioisomers, structural isomers, rotational isomers, tautomers, and the like. For compounds which contain one or more stereogenic centers, e.g., chiral compounds, the methods of the present invention may be carried out with an enantiomerically enriched compound, a racemate, or a mixture of diastereomers.

As used herein, the term "target protein" refers to a protein molecule or a portion of a protein capable of being bound by a selective binding compound. In certain embodiments, a target protein is FLT3.

"Drug resistance" refers to the tolerance of microorganisms, parasites and tumor cells to the effects of chemotherapeutic drugs. Once drug resistance occurs, the chemotherapeutic effect of drugs is significantly reduced. Drug resistance can be categorized as acquired drug resistance and intrinsic drug resistance according to its causes. For antitumor drugs, insensitivity of tumor cells to antineoplastic drugs, that is, drug resistance, is an important cause of failure in tumor chemotherapy, and it is also an urgent problem to be solved for tumor chemotherapy. The drug resistance involved in the invention generally refers to the drug resistance developed in patients suffering from FLT3-related diseases after being treated with medicaments other than the compounds of the present invention.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

The term "EGFR" as used in the specification refers to epidermal growth factor receptor.

The term "BMX" as used in the specification refers to bone marrow tyrosine kinase on chromosome X (Bone Marrow X kinase).

The term "ABL" as used in the specification refers to protein expressed by Abelson murine leukemia viral oncogene.

The term "MET" as used in the specification refers to hepatocyte growth factor receptor, also known as HGFR.

The following naming conventions are used to refer to amino acid substitutions in the specification: original amino acid, position, amino acid after substitution. For example, substituting aspartic acid at position 835 (Asp835) for tyrosine (Tyr) is abbreviated as D835Y.

In the specification, a protein having a certain mutation is denoted as: the protein that is mutated, followed by the specific mutation, with "/", "-" or "[ ]" intervening therebetween. For example, a mutated FLT3 kinase having internal tandem duplication is abbreviated as FLT3/ITD, FLT3-ITD or FLT3[ITD]; a mutated FLT3 kinase having D835Y mutation is abbreviated as FLT3/D835Y, FLT3/D835Y or FLT3 [D835Y].

The Novel Kinase Inhibitors of the Present Invention

The present invention provides a novel inhibitor of FLT3 kinase, comprising a compound of Formula (I) or a pharmaceutically acceptable salt, solvate, isomer, ester, acid, metabolite or prodrug thereof:

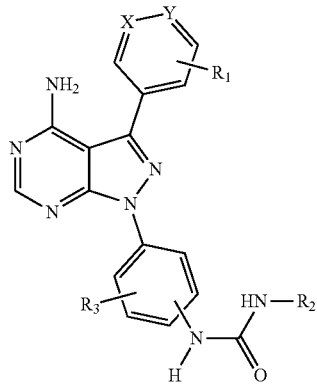

Formula (I)

wherein, at least one of X and Y is C, and the other is selected from the group consisting of C and N;

$R_1$ is selected from the group consisting of hydrogen, halogen, $C_{1-8}$ alkyl, $C_{1-8}$ haloalkyl, $C_{1-8}$ alkoxy, $C_{1-8}$ alkylamino, $C_{1-8}$ haloalkoxy, $C_{1-8}$ aminoalkyl, $C_{1-8}$ aminoalkoxy, $C_{1-8}$ alkylamino $C_{1-8}$ alkoxy, quaternary ammonium $C_{1-8}$ alkoxy, $C_{1-8}$ alkanoyl $C_{1-8}$ alkyl, arylcarbonyl $C_{1-8}$ alkyl, $C_{1-8}$ alkanoyl $C_{1-8}$ alkoxy, arylcarbonyl $C_{1-8}$ alkoxy, aminosulfonyl, $C_{1-8}$ alkylaminosulfonyl, $C_{3-6}$ heterocycloalkyl, aminoacyl, $C_{1-8}$ alkylaminocarbonyl, $C_{3-6}$ heterocycloalkylcarbonyl, $C_{3-6}$ cycloalkyl, $C_{1-8}$ alkyl($C_{3-6}$ heterocycloalkyl), $C_{1-8}$ alkoxy($C_{3-6}$ heterocycloalkyl), $C_{3-6}$ heterocycloalkylcarbonyl $C_{1-8}$ alkyl, aryloxy, $C_{1-8}$ alkylsulfonyl, $C_{1-8}$ alkylsulfonylamino, $C_{3-6}$ cycloalkylsulfonylamino, $C_{3-6}$ heterocycloalkylaminocarbonyl, acylamino($C_{1-8}$ alkylamino $C_{1-8}$ alkyl), and $C_{1-8}$ alkylamino($C_{1-8}$ alkylamino), wherein aryl and heterocycloalkyl are optionally substituted with 1-3 independent $R_4$;

$R_2$ is selected from the group consisting of $C_{1-8}$ alkyl, $C_{1-8}$ haloalkyl, $C_{1-8}$ alkylamino $C_{1-8}$ alkyl, aryl and heteroaryl, wherein aryl and heteroaryl are optionally substituted with 1-3 independent $R_4$;

$R_3$ is selected from the group consisting of hydrogen, halogen, $C_{1-8}$ alkyl and $C_{1-8}$ haloalkyl;

$R_4$ independently selected from the group consisting of halogen, $C_{1-8}$ alkyl, $C_{1-8}$ alkoxy, $C_{1-8}$ haloalkyl, $C_{1-8}$ hydroxyalkyl, $C_{1-8}$ aminoalkyl, $C_{1-8}$ alkanoyl, $C_{1-8}$ alkylsulfonyl, and aminoacyl.

In a preferred embodiment, both X and Y are C.

In another preferred embodiment, $R_1$ is a substituent on X or Y, preferably substituent on Y.

In an embodiment of the invention, the alkyl as mentioned in relation to groups $R_1$, $R_2$, $R_3$ and $R_4$ is preferably methyl, ethyl, n-propyl, isopropyl, n-butyl, isobutyl or tert-butyl; the aryl is preferably phenyl; the heteroaryl is preferably isoxazolyl or thiazolyl; the heterocycloalkyl is preferably 6-membered heterocycloalkyl, e.g., morpholinyl, piperidinyl, piperazinyl or tetrahydropyranyl; the alkanoyl is preferably acetyl or propionyl; the alkylamino is preferably methylamino, ethylamino, dimethylamino, diethylamino or methylethylamino; the alkylsulfonyl is preferably methylsulfonyl, ethylsulfonyl, propylsulfonyl, n-butylsulfonyl, isobutylsulfonyl or tert-butylsulfonyl; the haloalkyl is preferably trifluoromethyl; the alkoxy is preferably methoxy, ethoxy, or propoxy.

In another aspect, the present invention provides a novel inhibitor of FLT3 kinase which comprises a compound of Formula (II) or a pharmaceutically acceptable salt, solvate, isomer, ester, acid, metabolite or prodrug thereof:

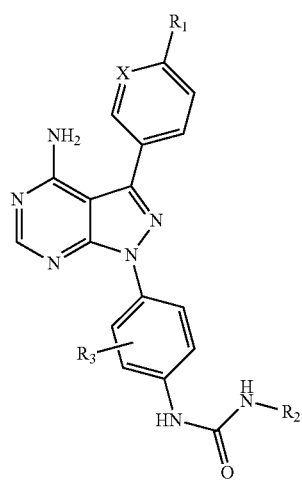

Formula (II)

wherein, X, $R_1$, $R_2$, $R_3$ and $R_4$ are defined as above.

In this embodiment, more preferably, $R_1$ is selected from the group consisting of hydrogen, $C_{1-8}$ alkylamino (such as dimethylamino, etc.), $C_{1-8}$ alkylamino $C_{1-8}$ alkoxy (such as 2-dimethylamino-ethoxy, 2-diethylamino-ethoxy, etc.), quaternary ammonium $C_{1-8}$ alkoxy (such as trimethylammoniummethoxy, etc.), $C_{1-8}$ alkylaminosulfonyl (such as dimethylaminosulfonyl, etc.), optionally substituted $C_{3-6}$ heterocycloalkyl (such as morpholino, piperidin-1-yl, piperazin-1-yl, 4-acetylpiperazin-1-yl, 4-methylpiperazin-1-yl, 4-ethylpiperazin-1-yl, piperidin-4-yl, 1-methylpiperidin-4-yl, 1-ethylpiperidin-4-yl, 1-(2-hydroxylethyl)-piperidin-4-yl, 4-(2-hydroxyethyl)-piperazin-1-yl, 4-(2-aminoethyl)-piperazin-1-yl, etc.), aminoacyl, $C_{1-8}$ alkylaminocarbonyl (such as methylaminocarbonyl, dimethylaminocarbonyl, etc.), optionally substituted $C_{3-6}$ heterocycloalkylcarbonyl (such as piperidine-1-carbonyl, 4-aminoacylpiperidin-1-carbonyl, morpholine-4-carbonyl, 4-ethylpiperazin-1-carbonyl, 4-isopropylpiperazin-1-carbonyl, etc.), optionally substituted $C_{1-8}$ alkyl($C_{3-6}$ heterocycloalkyl) (such as morpholinomethyl, (4-methylpiperidin-1-yl)methyl, (4-methylpiperazin-1-yl)methyl, (4-ethylpiperazin-1-yl)methyl, (4-acetylpiperazin-1-yl)methyl, etc.), optionally substituted $C_{1-8}$ alkoxy($C_{3-6}$ heterocycloalkyl) (such as 2-morpholinomethoxyl, 2-morpholinoethoxy, 3-morpholinopropoxy, (2-piperidin-1-yl)ethoxy, 2-(4-(mesyl)piperazin-1-yl)ethoxy, (4-methylpiperazin-1-yl)ethoxy, etc.), optionally substituted $C_{3-6}$ heterocycloalkylcarbonyl $C_{1-8}$ alkyl (such as 2-morpholino-2-oxoethyl, 3-morpholino-3-oxo-propyl, 3-(4-ethylpiperazin-1-yl)-3-oxo-propyl, etc.), optionally substituted phenoxyl, $C_{1-8}$ alkylsulfonyl (such as mesyl, isopropylsulfonyl, iso-butylsulfonyl, etc.), $C_{1-8}$ alkylsulfonylamino (such as mesylamino, isopropyl sulfonyl amino, etc.), $C_{3-6}$ cycloalkylsulfonylamino (such as cyclopropyl sulfonylamino), optionally substituted $C_{3-6}$ heterocycloalkylaminocarbonyl (such as (tetrahydropyran-4-yl)aminocarbonyl, morpholinoaminocarbonyl, etc.), acylamino($C_{1-8}$ alkylamino $C_{1-8}$ alkyl) (such as 2-(dimethylamino)acetamido, etc.), and $C_{1-8}$ alkylamino($C_{1-8}$ alkylamino) (such as (2-(dimethylamino)ethyl)methylamino, etc.). $R_1$ is most preferably $C_{1-8}$ alkoxy($C_{3-6}$ heterocycloalkyl), especially 2-morpholinomethoxyl, 2-morpholinoethoxy, 3-morpholinopropoxy, and (2-piperidin-1-yl)ethoxy, etc.

In this embodiment, more preferably, $R_2$ is selected from the group consisting of $C_{1-8}$ alkyl (such as isobutyl, etc.), $C_{1-8}$ alkylamino $C_{1-8}$ alkyl (such as 2-(dimethylamino)ethyl, etc.), optionally substituted phenyl (such as 4-(tert-butyl)phenyl, 4-methyl-3-(trifluoromethyl)phenyl, 4-chloro-3-(trifluoromethyl)phenyl, 3,4,5-trimethoxyphenyl, etc.), and optionally substituted heteroaryl (such as isoxazol-3-yl, 5-(methyl)isoxazol-3-yl, 5-(tert-butyl)isoxazol-3-yl, 4-(tert-butyl)thiazol-2-yl, 4-(trifluoromethyl)thiazol-2-yl, etc.). $R_2$ is mostly preferably 5-(tert-butyl)isoxazol-3-yl.

In this embodiment, more preferably, $R_3$ is selected from the group consisting of hydrogen and $C_{1-8}$ alkyl (such as methyl, etc.). $R_3$ is mostly preferably hydrogen.

In this invention, preferred FLT3 kinase inhibitors comprises the compounds of Table 1 as well as the pharmaceutically acceptable salts, solvates, isomers, esters, acids, metabolites or prodrugs thereof:

TABLE 1

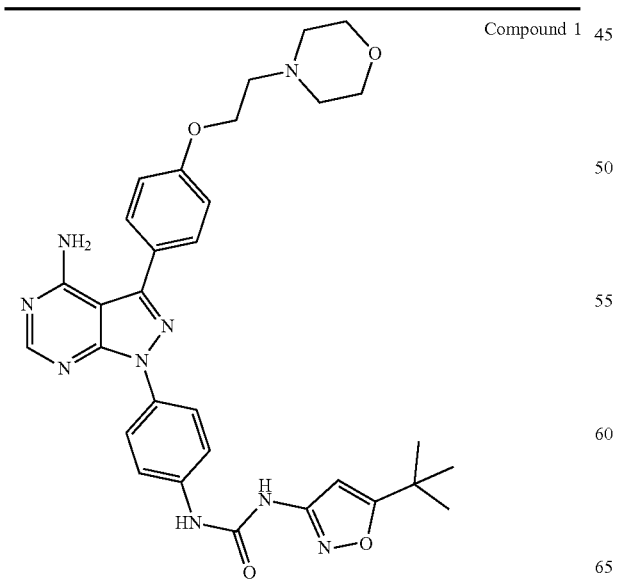

Compound 1

TABLE 1-continued

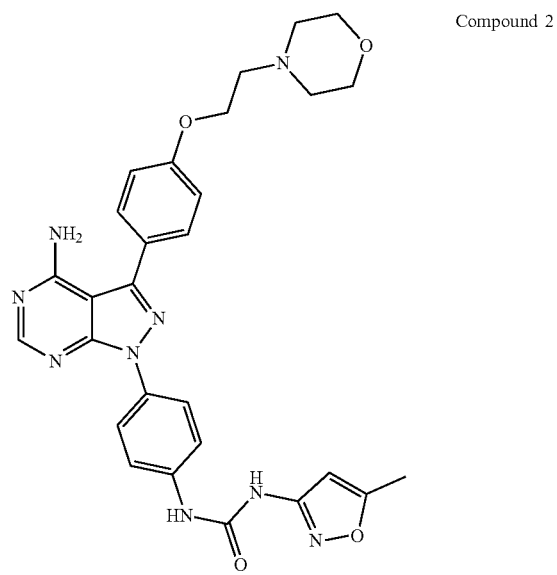

Compound 2

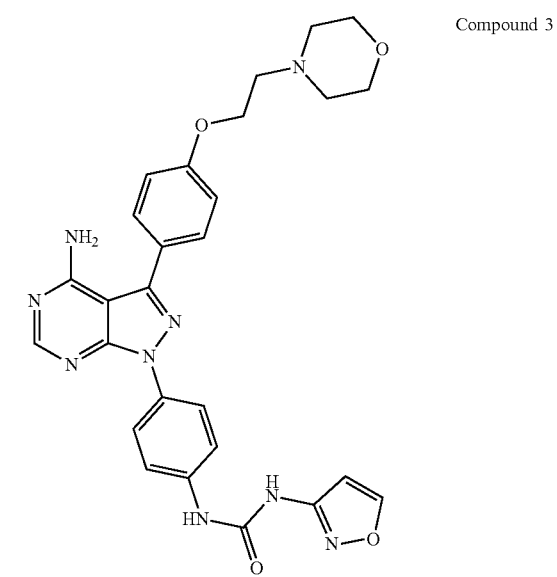

Compound 3

TABLE 1-continued
Compound 4
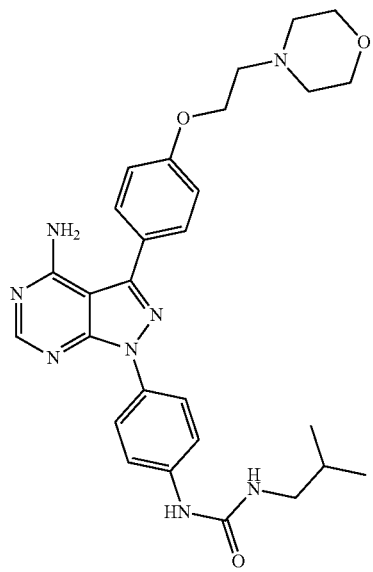 [SMILES: CC(C)CNC(=O)Nc1ccc(-n2nc(-c3ccc(OCCN4CCOCC4)cc3)c3c(N)ncnc32)cc1]
Compound 6
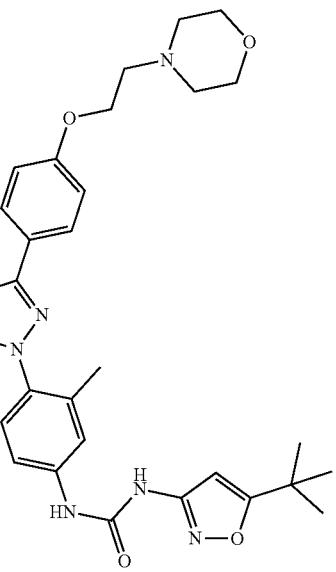
Compound 5
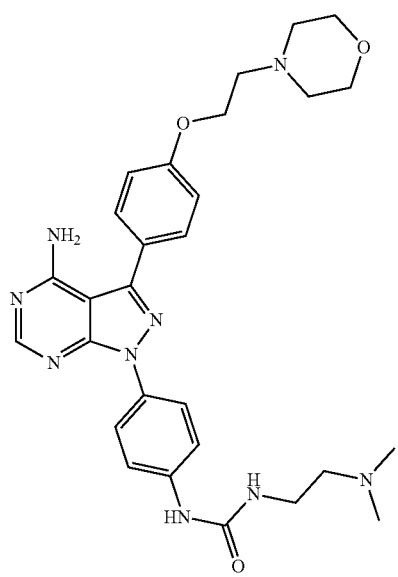 [SMILES: CN(C)CCNC(=O)Nc1ccc(-n2nc(-c3ccc(OCCN4CCOCC4)cc3)c3c(N)ncnc32)cc1]
Compound 7
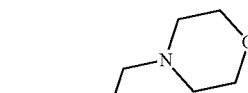

TABLE 1-continued
Compound 8
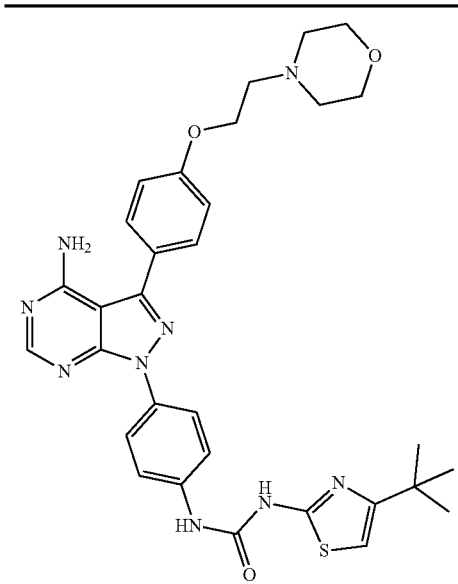
Compound 10
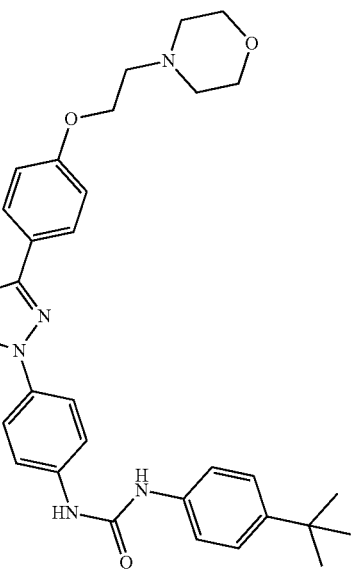
Compound 9
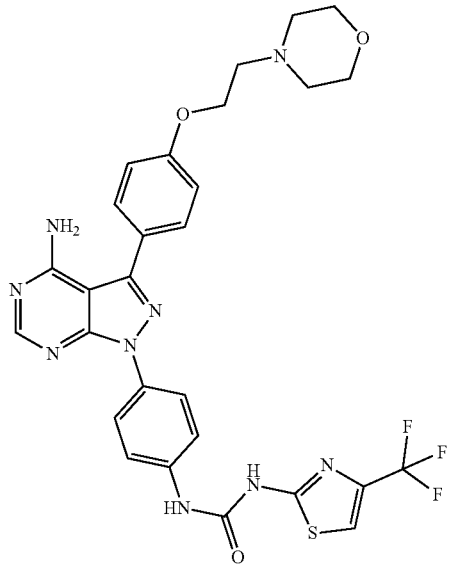 [SMILES: Nc1ncnc2c1c(-c1ccc(OCCN3CCOCC3)cc1)nn2-c1ccc(NC(=O)Nc2nc(C(F)(F)F)cs2)cc1]
Compound 11
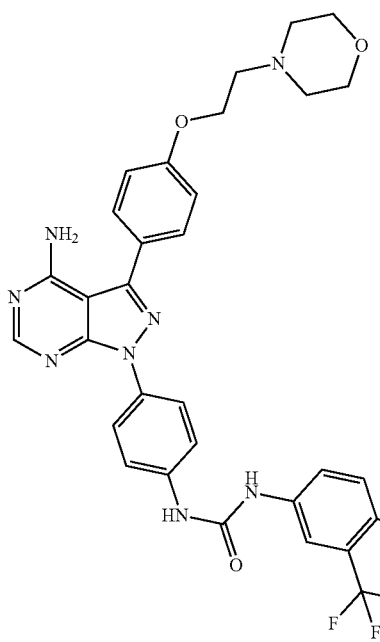

TABLE 1-continued
Compound 12
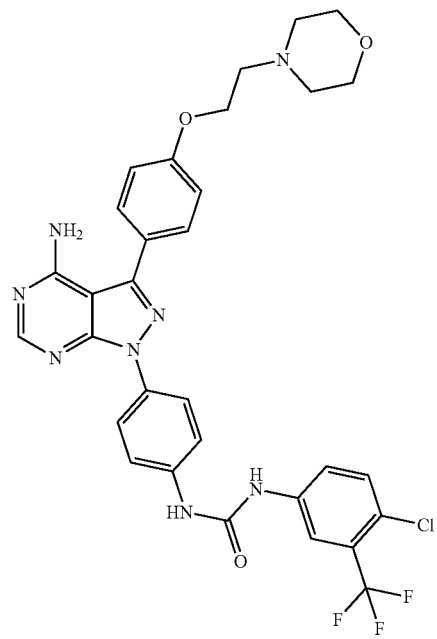 [SMILES: Nc1ncnc2c1c(-c1ccc(OCCN3CCOCC3)cc1)nn2-c1ccc(NC(=O)Nc2ccc(Cl)c(C(F)(F)F)c2)cc1]
Compound 13
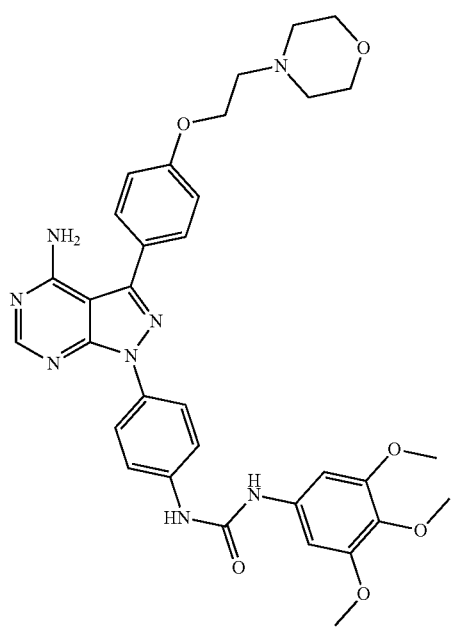 [SMILES: COc1cc(NC(=O)Nc2ccc(-n3nc(-c4ccc(OCCN5CCOCC5)cc4)c4c(N)ncnc43)cc2)cc(OC)c1OC]
TABLE 1-continued
Compound 14
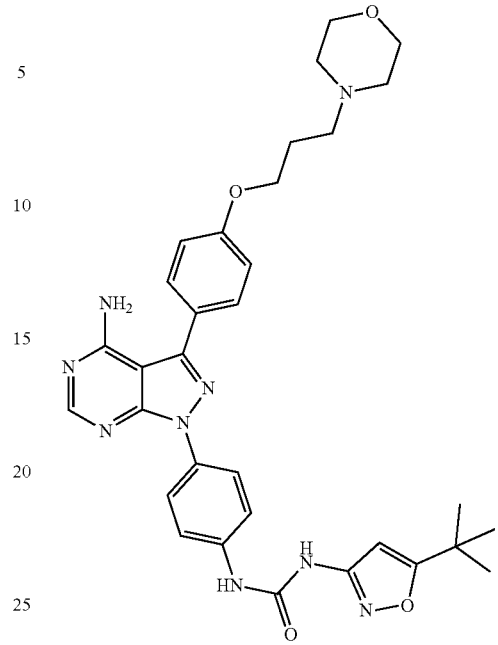
Compound 15
Compound 16
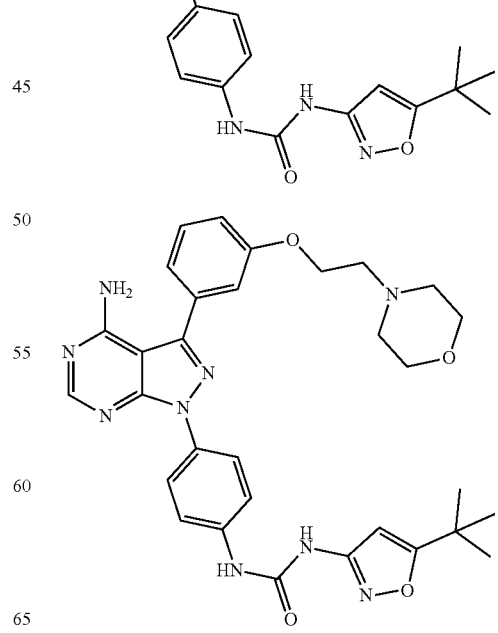

TABLE 1-continued
Compound 17
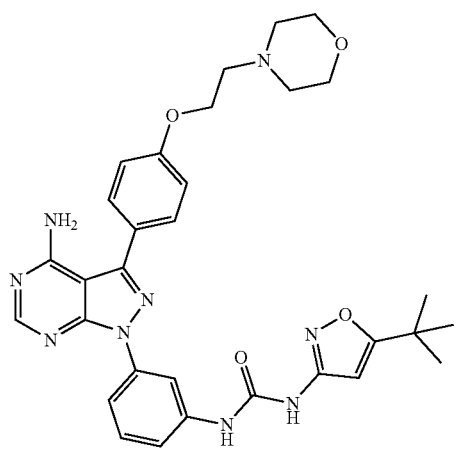 [SMILES: CC(C)(C)c1cc(NC(=O)Nc2cccc(-n3nc(-c4ccc(OCCN5CCOCC5)cc4)c4c(N)ncnc43)c2)no1]
Compound 18
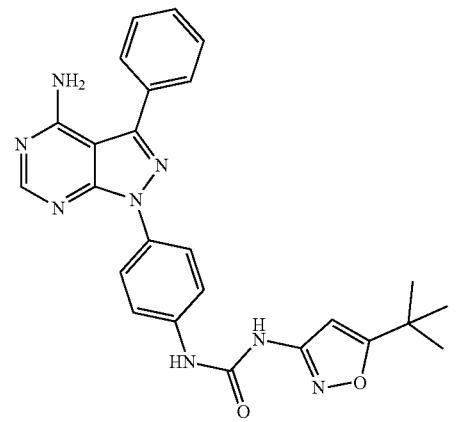 [SMILES: CC(C)(C)c1cc(NC(=O)Nc2ccc(-n3nc(-c4ccccc4)c4c(N)ncnc43)cc2)no1]
Compound 19
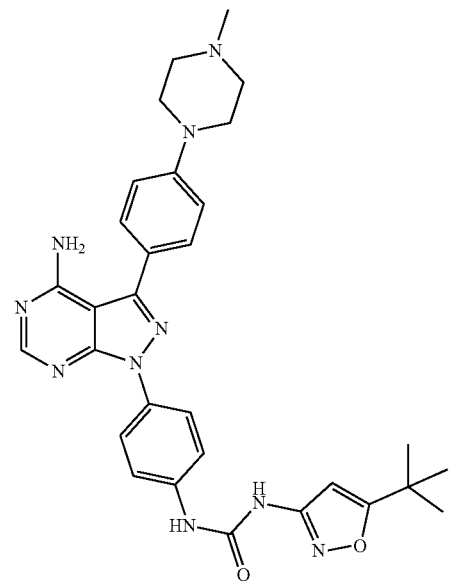 [SMILES: CN1CCN(c2ccc(-c3nn(-c4ccc(NC(=O)Nc5cc(C(C)(C)C)on5)cc4)c4ncnc(N)c34)cc2)CC1]
TABLE 1-continued
Compound 20
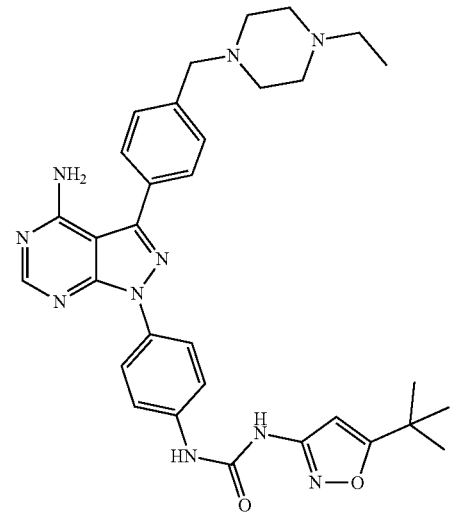 [SMILES: CCN1CCN(Cc2ccc(-c3nn(-c4ccc(NC(=O)Nc5cc(C(C)(C)C)on5)cc4)c4ncnc(N)c34)cc2)CC1]
Compound 21
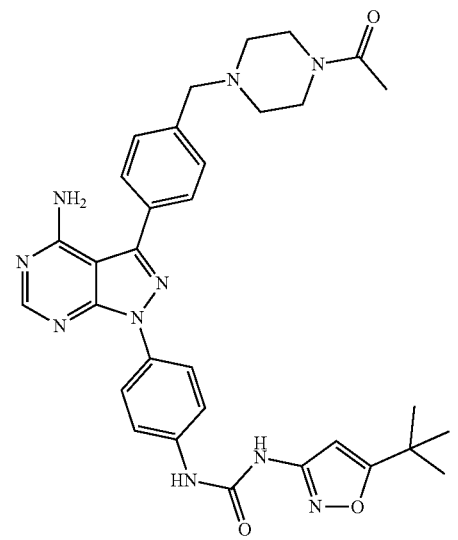 [SMILES: CC(=O)N1CCN(Cc2ccc(-c3nn(-c4ccc(NC(=O)Nc5cc(C(C)(C)C)on5)cc4)c4ncnc(N)c34)cc2)CC1]
Compound 22
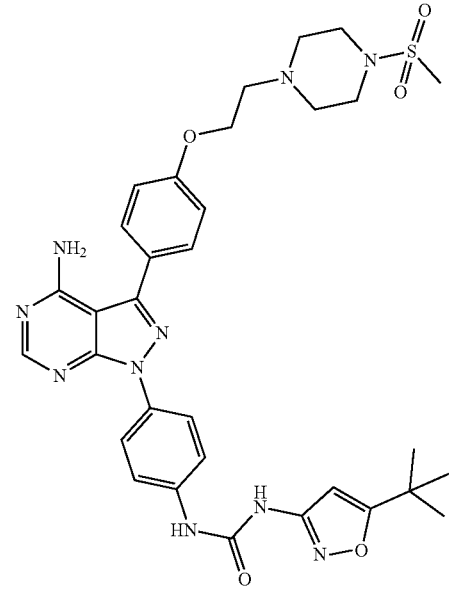 [SMILES: CC(C)(C)c1cc(NC(=O)Nc2ccc(-n3nc(-c4ccc(OCCN5CCN(S(C)(=O)=O)CC5)cc4)c4c(N)ncnc43)cc2)no1]

TABLE 1-continued
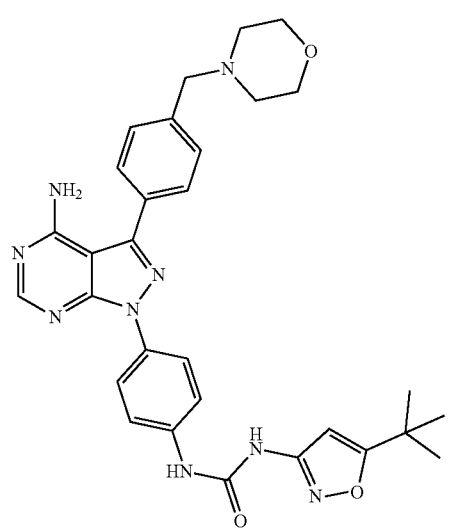 [SMILES: CC(C)(C)c1cc(NC(=O)Nc2ccc(-n3nc(-c4ccc(CN5CCOCC5)cc4)c4c(N)ncnc43)cc2)no1]
Compound 23
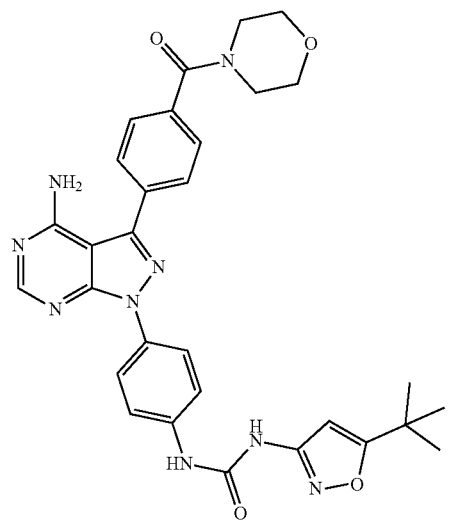 [SMILES: CC(C)(C)c1cc(NC(=O)Nc2ccc(-n3nc(-c4ccc(C(=O)N5CCOCC5)cc4)c4c(N)ncnc43)cc2)no1]
Compound 24
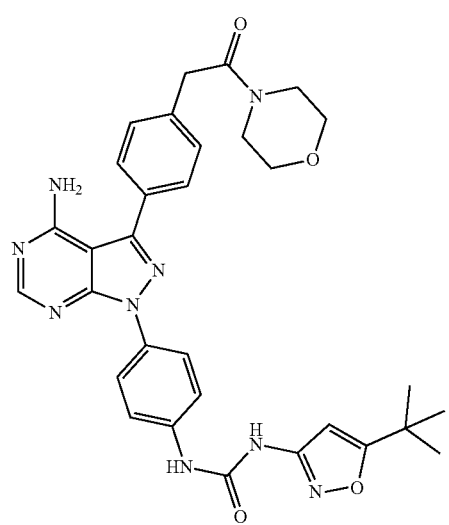 [SMILES: CC(C)(C)c1cc(NC(=O)Nc2ccc(-n3nc(-c4ccc(CC(=O)N5CCOCC5)cc4)c4c(N)ncnc43)cc2)no1]
Compound 25
TABLE 1-continued
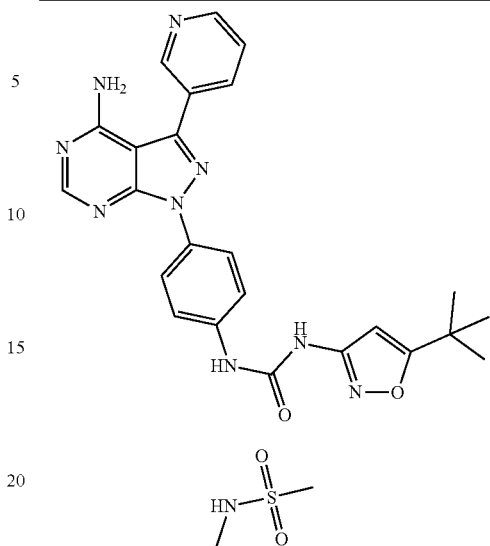
Compound 26
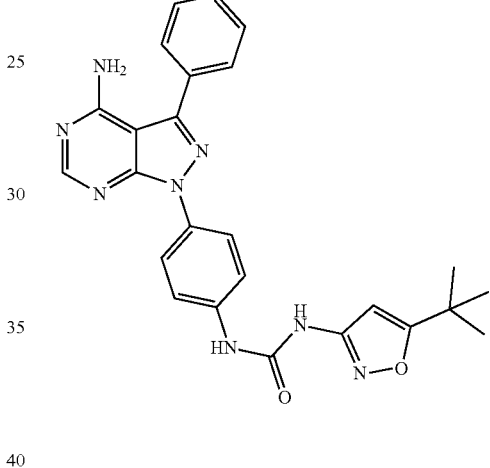
Compound 27
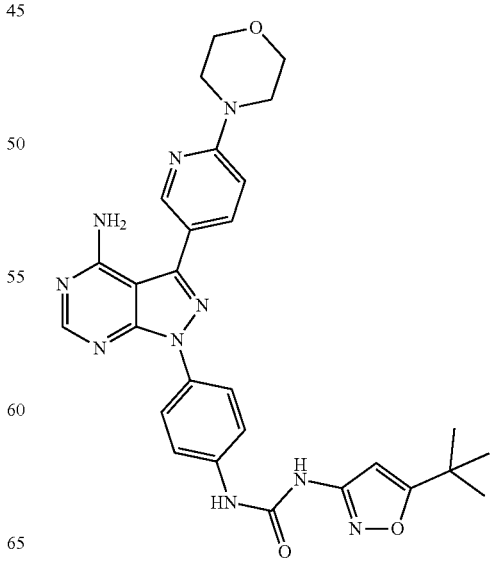
Compound 28

TABLE 1-continued
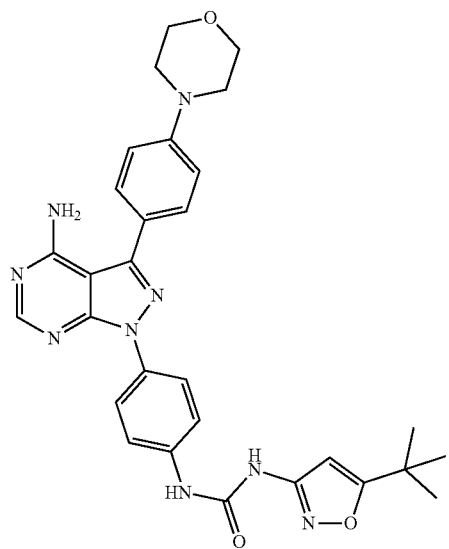 [SMILES: CC(C)(C)c1cc(NC(=O)Nc2ccc(-n3nc(-c4ccc(N5CCOCC5)cc4)c4c(N)ncnc43)cc2)no1]
Compound 29
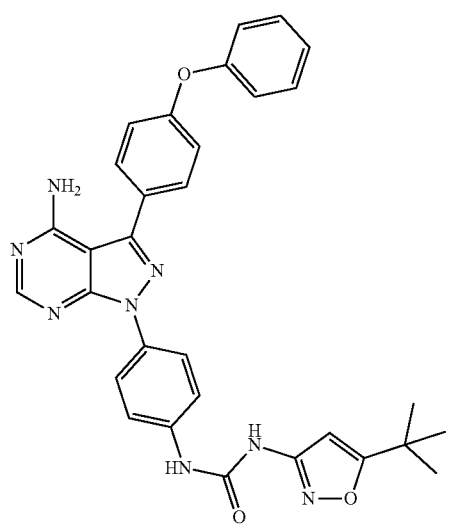 [SMILES: CC(C)(C)c1cc(NC(=O)Nc2ccc(-n3nc(-c4ccc(Oc5ccccc5)cc4)c4c(N)ncnc43)cc2)no1]
Compound 30
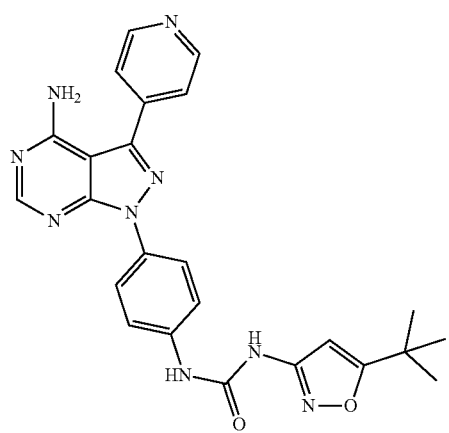 [SMILES: CC(C)(C)c1cc(NC(=O)Nc2ccc(-n3nc(-c4ccncc4)c4c(N)ncnc43)cc2)no1]
Compound 31
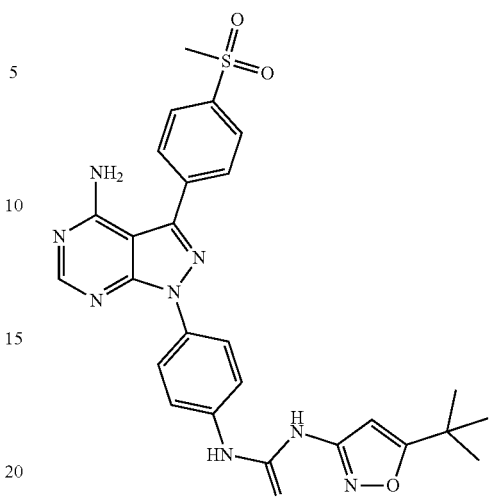
Compound 32
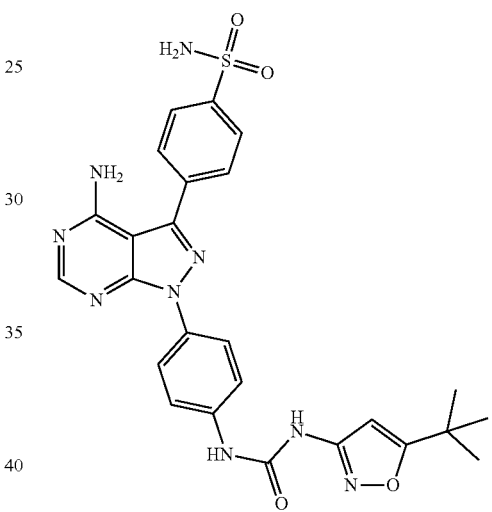
Compound 33
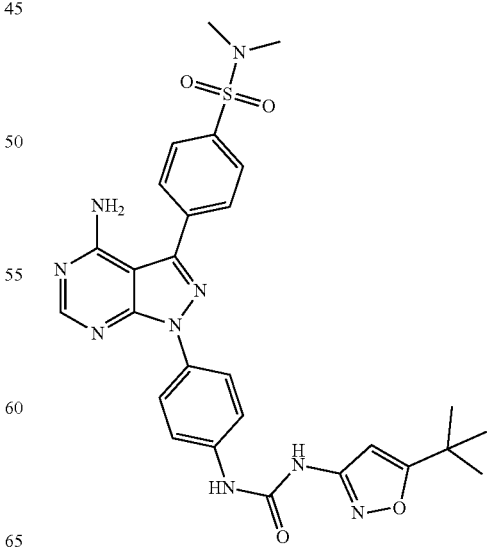
Compound 34

TABLE 1-continued
Compound 35
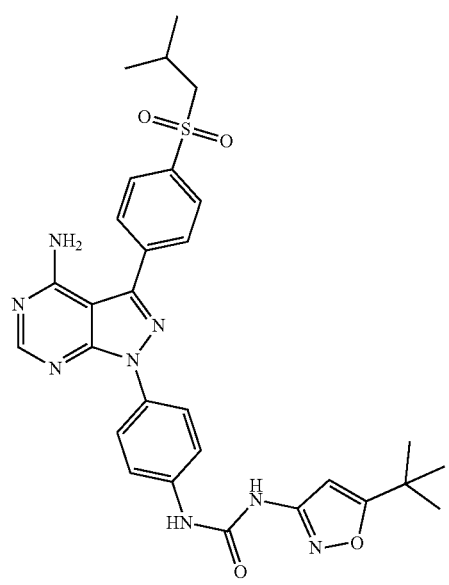 [SMILES: CC(C)CS(=O)(=O)c1ccc(-c2nn(-c3ccc(NC(=O)Nc4cc(C(C)(C)C)on4)cc3)c3ncnc(N)c23)cc1]
Compound 36
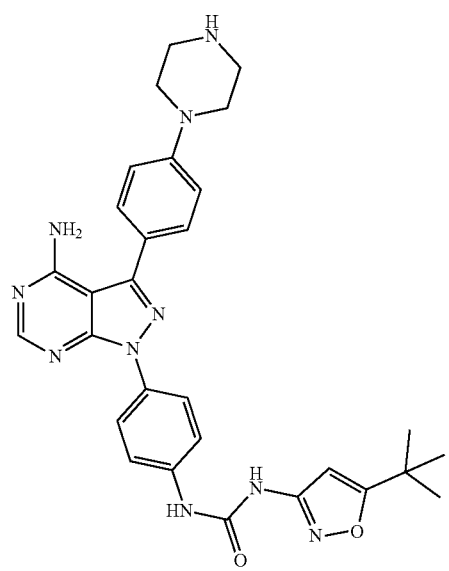 [SMILES: CC(C)(C)c1cc(NC(=O)Nc2ccc(-n3nc(-c4ccc(N5CCNCC5)cc4)c4c(N)ncnc43)cc2)no1]
TABLE 1-continued
Compound 37
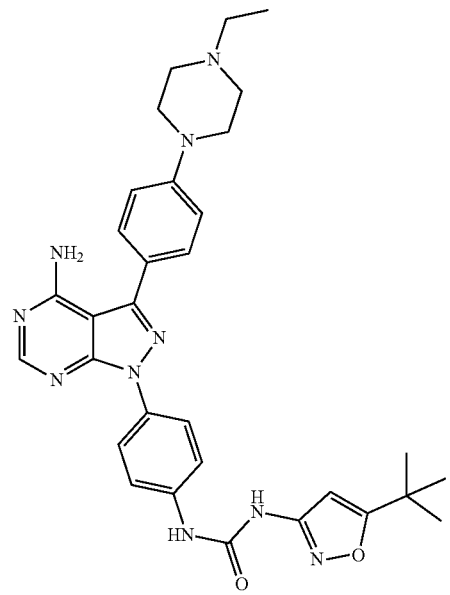 [SMILES: CCN1CCN(c2ccc(-c3nn(-c4ccc(NC(=O)Nc5cc(C(C)(C)C)on5)cc4)c4ncnc(N)c34)cc2)CC1]
Compound 38
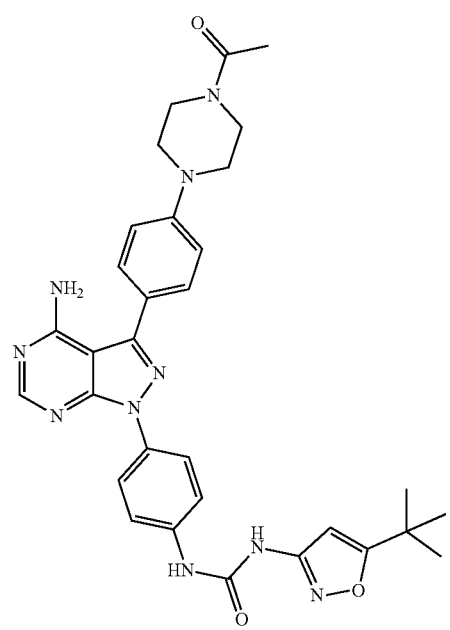 [SMILES: CC(=O)N1CCN(c2ccc(-c3nn(-c4ccc(NC(=O)Nc5cc(C(C)(C)C)on5)cc4)c4ncnc(N)c34)cc2)CC1]

TABLE 1-continued
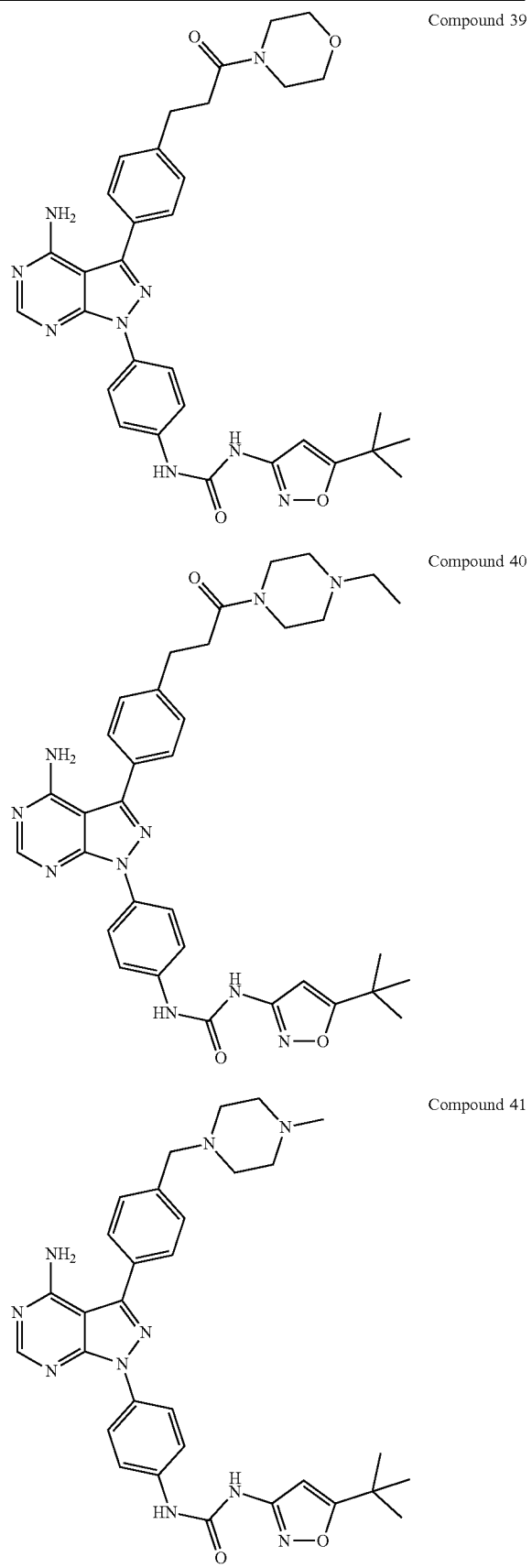
Compound 39
Compound 40
Compound 41
TABLE 1-continued
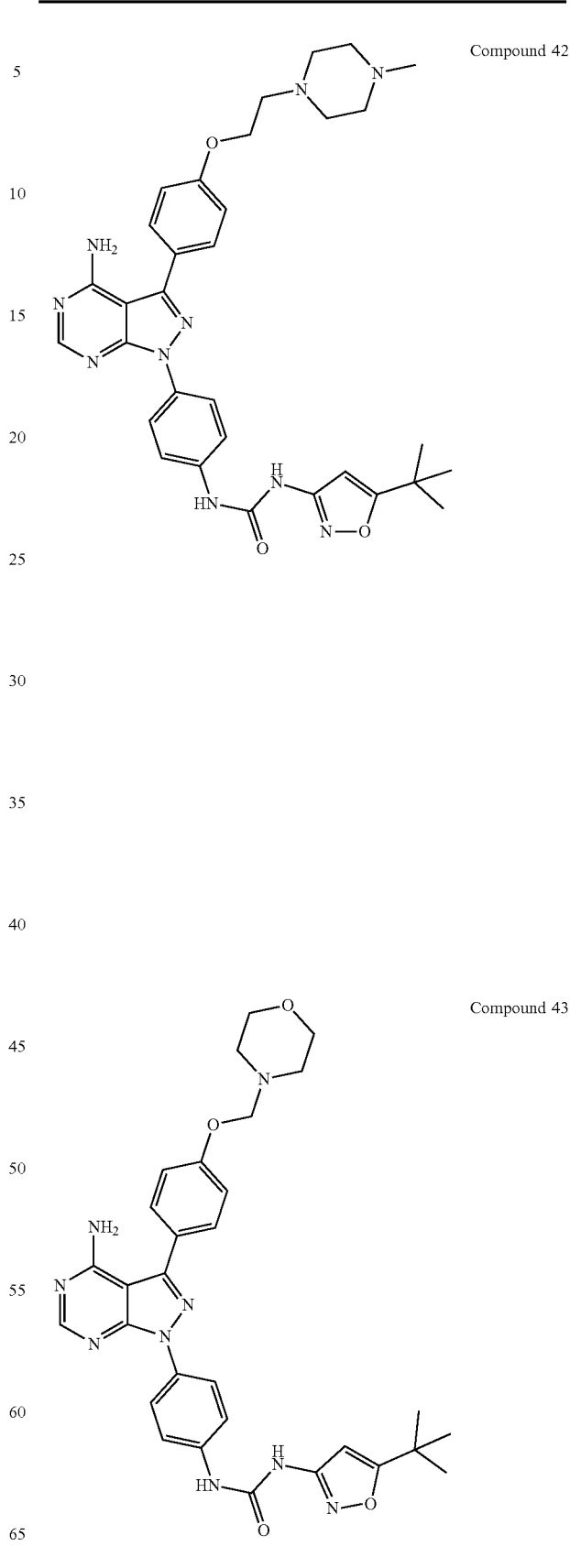
Compound 42
Compound 43

TABLE 1-continued
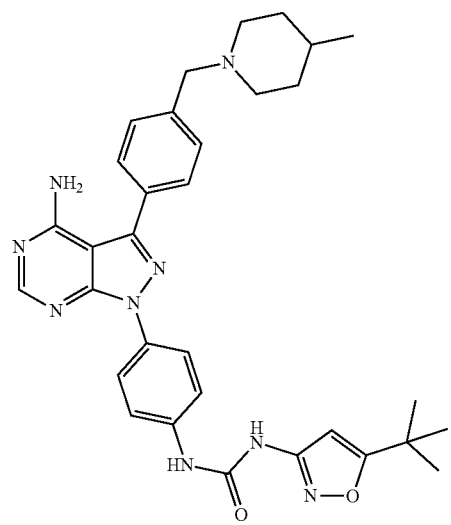 [SMILES: CC1CCN(Cc2ccc(-c3nn(-c4ccc(NC(=O)Nc5cc(C(C)(C)C)on5)cc4)c4ncnc(N)c34)cc2)CC1]
Compound 44
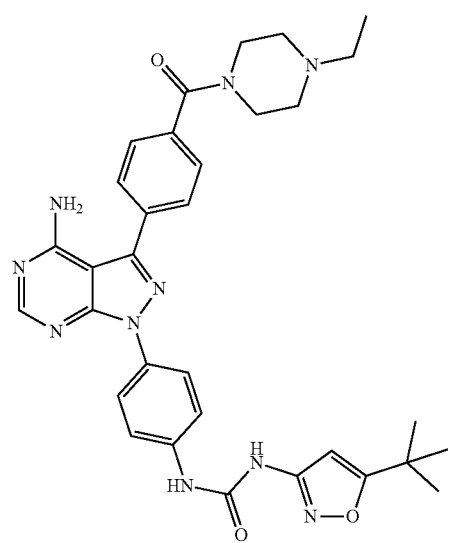 [SMILES: CCN1CCN(C(=O)c2ccc(-c3nn(-c4ccc(NC(=O)Nc5cc(C(C)(C)C)on5)cc4)c4ncnc(N)c34)cc2)CC1]
Compound 45
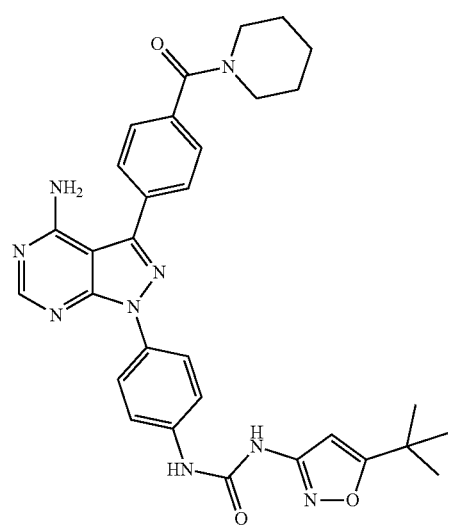 [SMILES: CC(C)(C)c1cc(NC(=O)Nc2ccc(-n3nc(-c4ccc(C(=O)N5CCCCC5)cc4)c4c(N)ncnc43)cc2)no1]
Compound 46
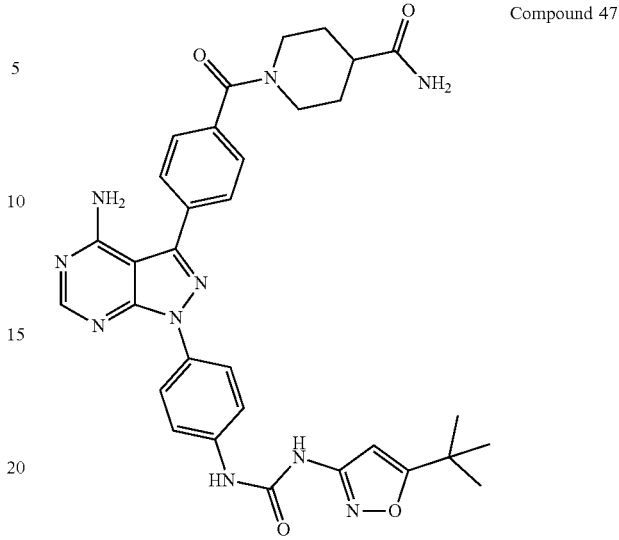
Compound 47
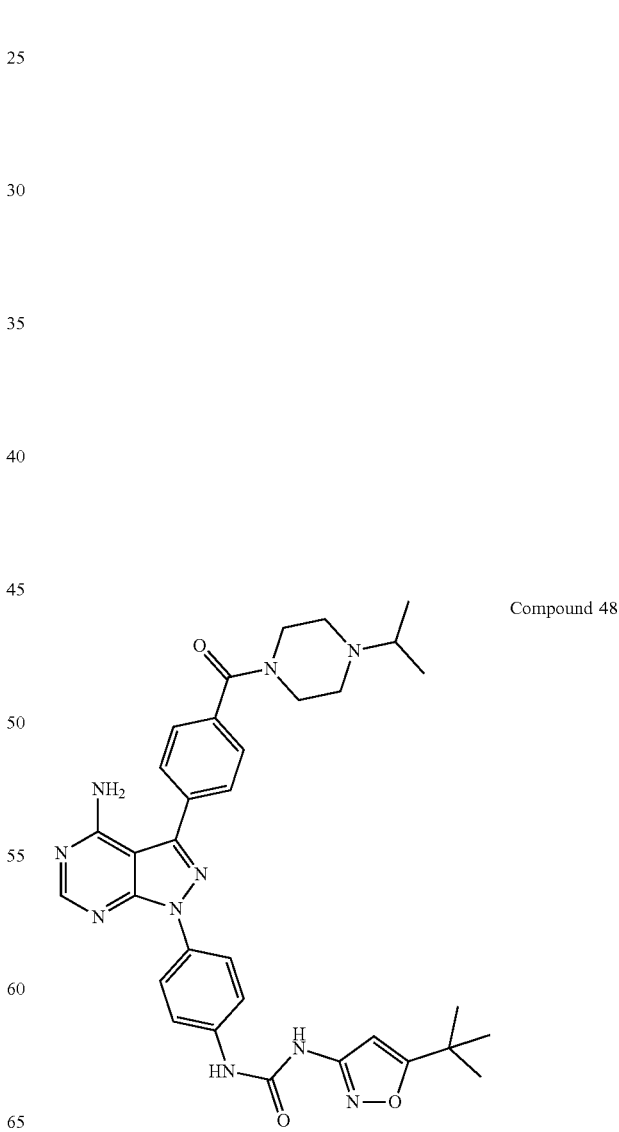
Compound 48

TABLE 1-continued
Compound 49
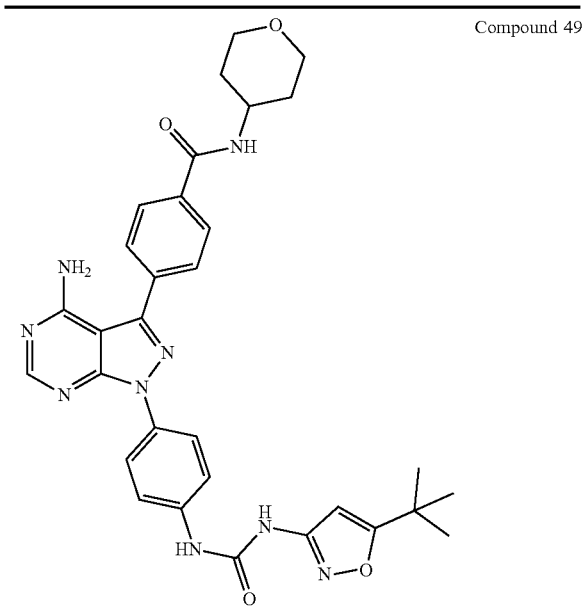
Compound 50
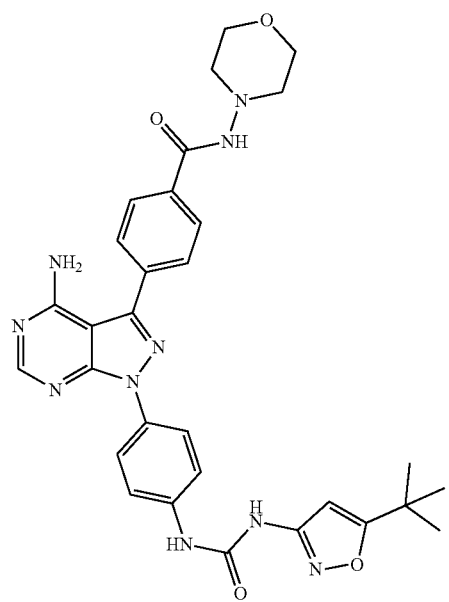 [SMILES: CC(C)(C)c1cc(NC(=O)Nc2ccc(-n3nc(-c4ccc(C(=O)NN5CCOCC5)cc4)c4c(N)ncnc43)cc2)no1]
Compound 51
Compound 52
Compound 53
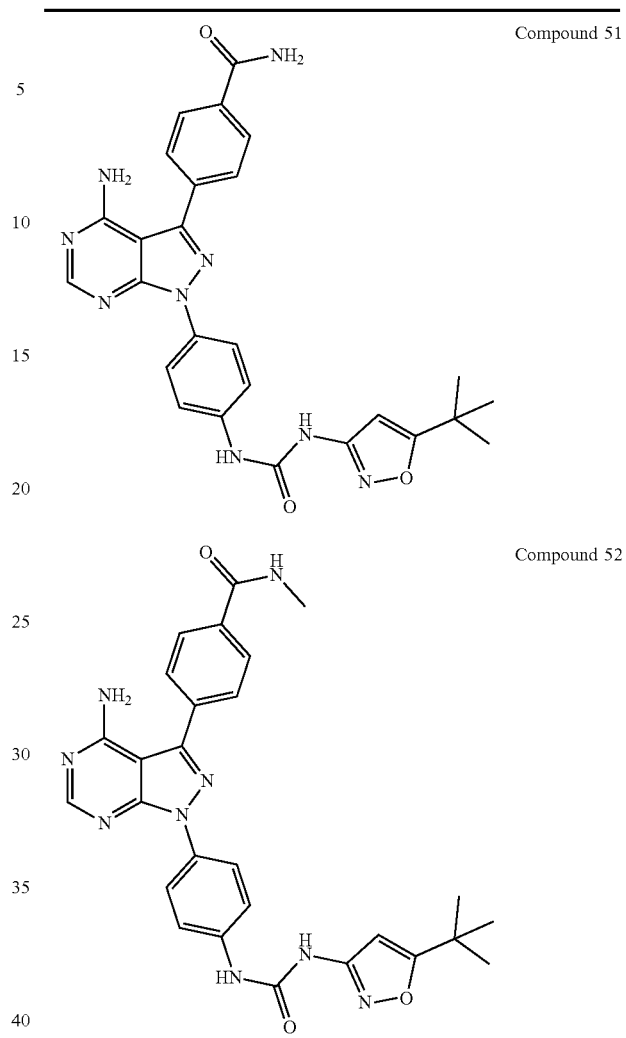
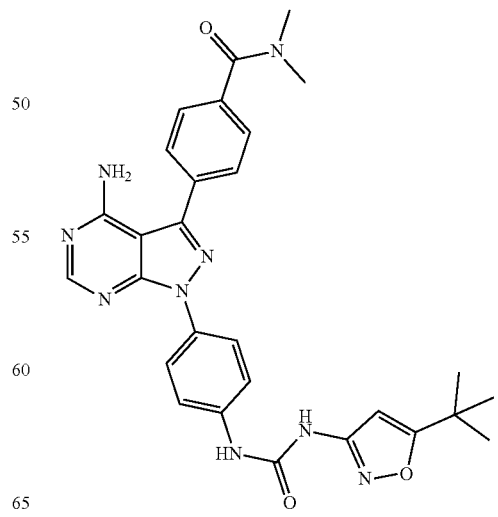

TABLE 1-continued
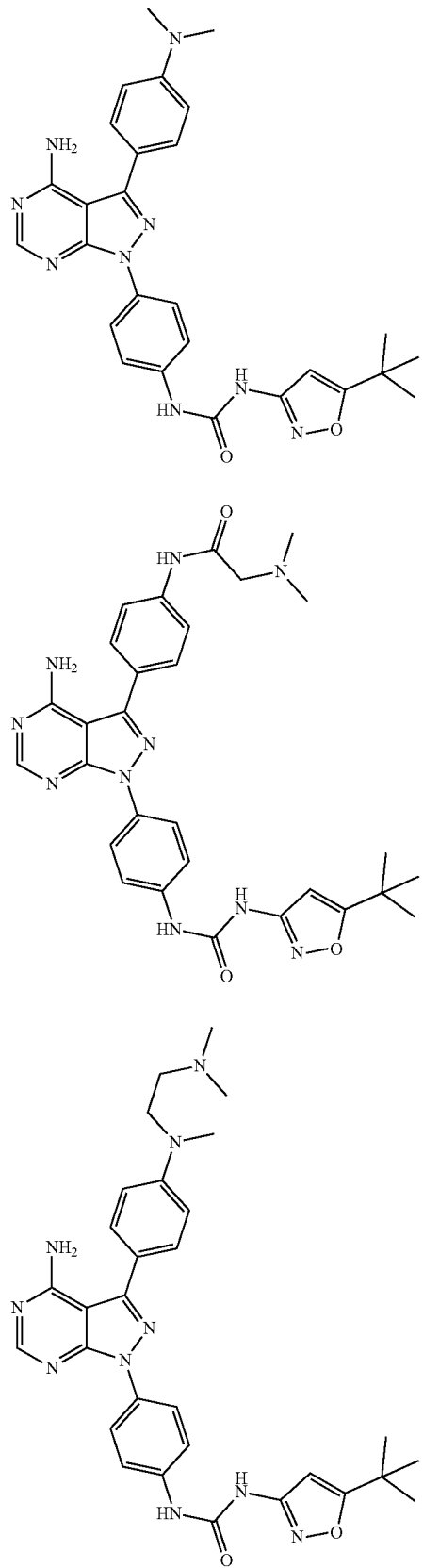
Compound 54
Compound 55
Compound 56
TABLE 1-continued
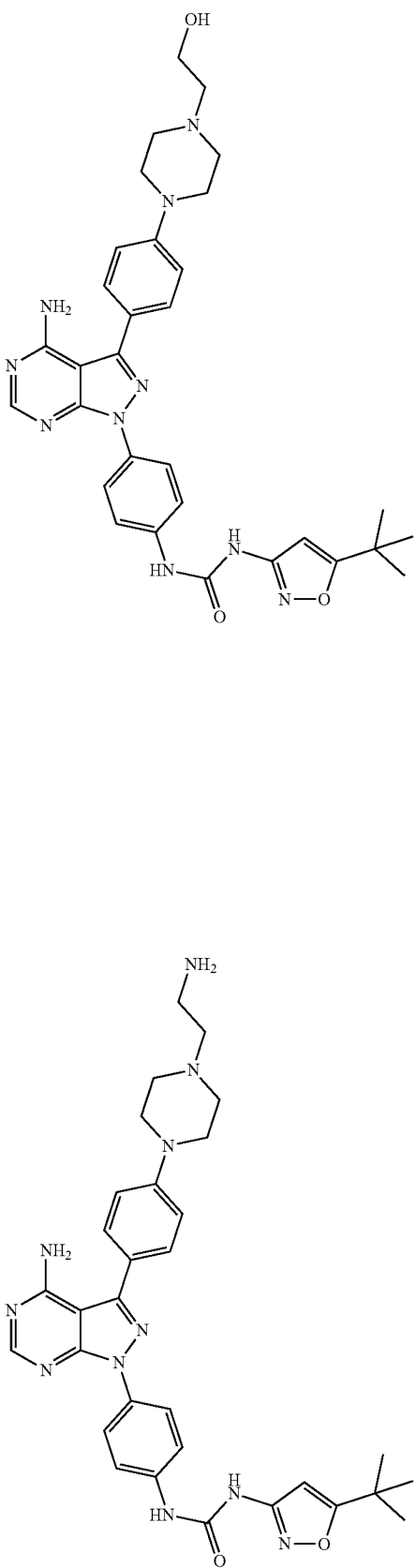
Compound 57
Compound 58

TABLE 1-continued
Compound 59
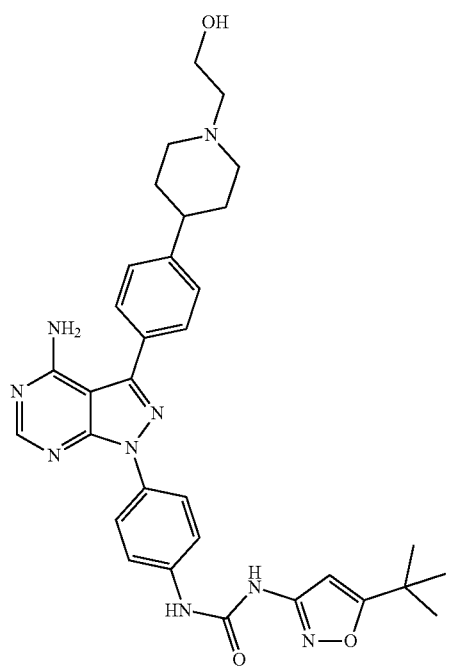 [SMILES: CC(C)(C)c1cc(NC(=O)Nc2ccc(-n3nc(-c4ccc(C5CCN(CCO)CC5)cc4)c4c(N)ncnc43)cc2)no1]
Compound 60
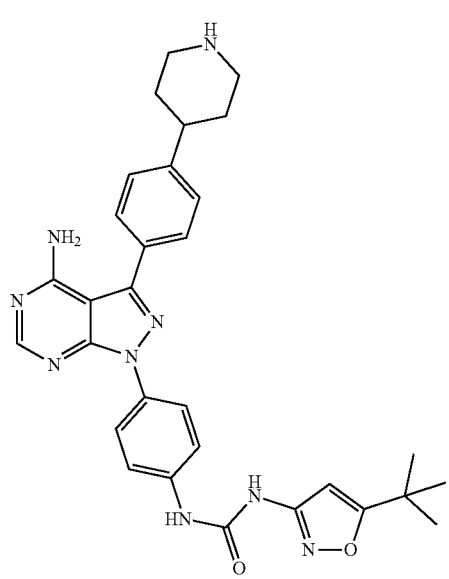 [SMILES: CC(C)(C)c1cc(NC(=O)Nc2ccc(-n3nc(-c4ccc(C5CCNCC5)cc4)c4c(N)ncnc43)cc2)no1]
TABLE 1-continued
Compound 61
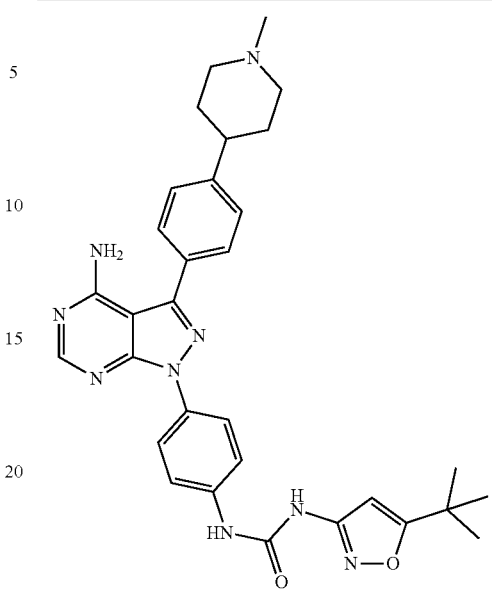
Compound 62
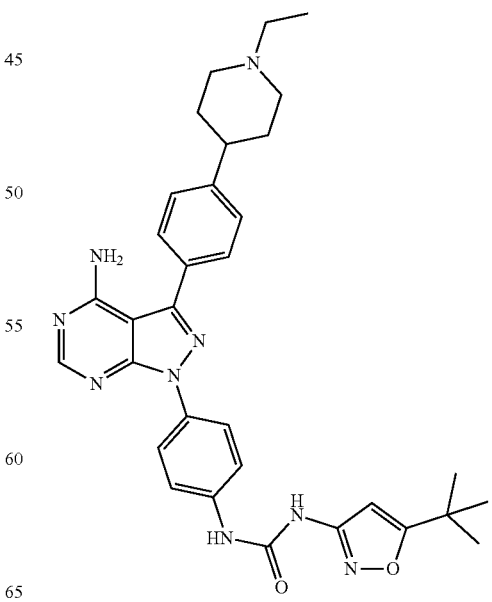

TABLE 1-continued
Compound 63
Compound 64
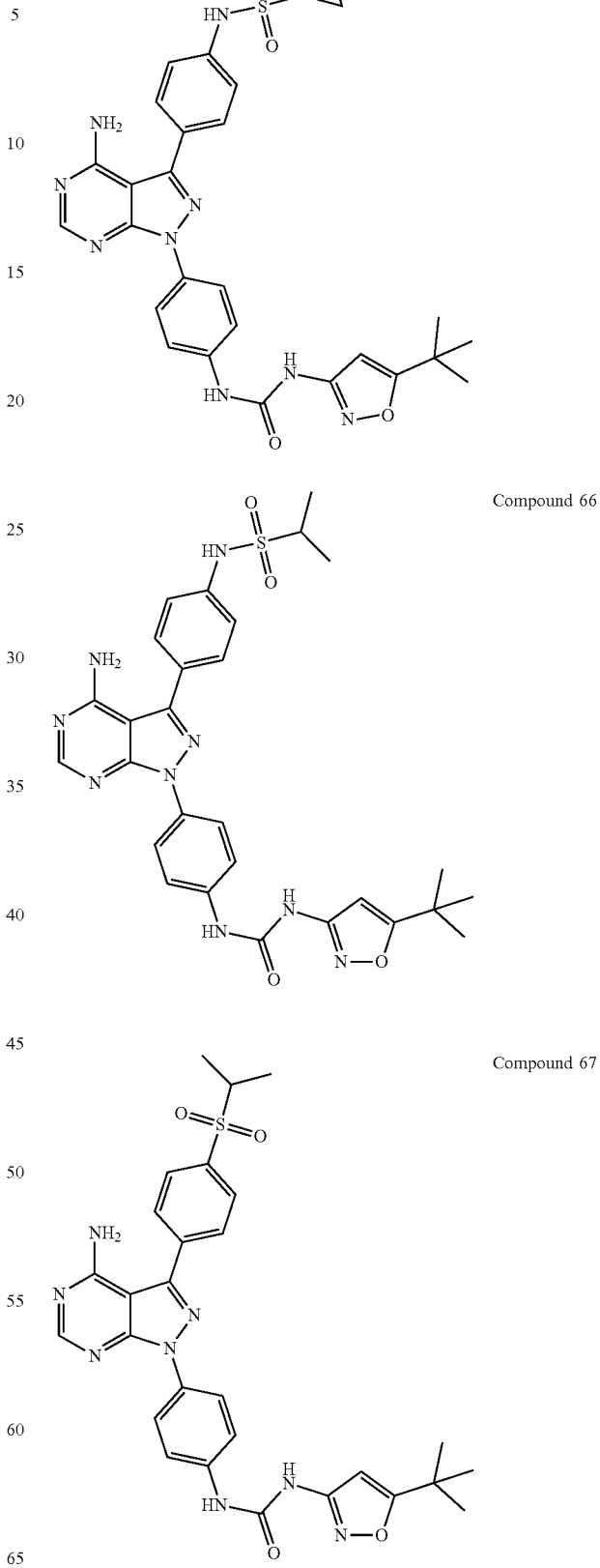
Compound 65
Compound 66
Compound 67

TABLE 1-continued

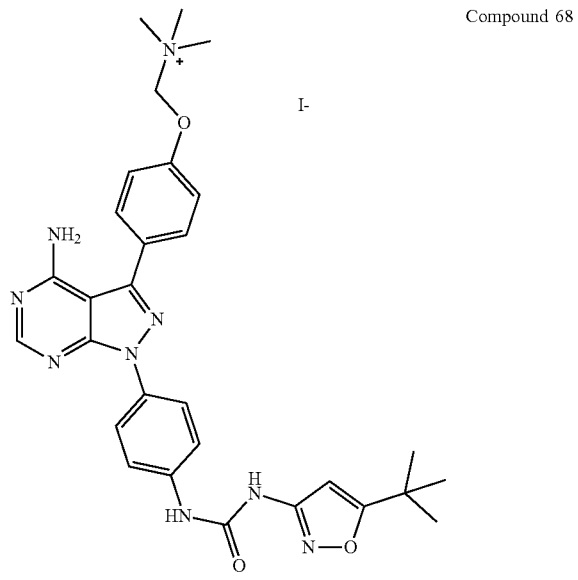

Compound 68

The chiral compounds involved in the present invention may be of any configuration or mixed racemates.

In one aspect, it is preferred herein to provide compounds selected from the group consisting of the group consisting of the following compounds, the structures of which are shown in Table 1.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Described herein are novel kinase inhibitors. The pharmaceutically acceptable salts, solvates, isomers, esters, acids, pharmaceutically active metabolites and prodrugs of these compounds are also described herein.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid-addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2] oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base-addition salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a nonsolvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy, and elemental analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition and the Use of the Present Invention

The present invention also relates to a pharmaceutical composition comprising compounds of Formula (I), or a pharmaceutically acceptable salt, solvate, isomer, ester, acid, metabolite or prodrug thereof, as an active ingredient, and a pharmaceutically acceptable carrier or excipient, and optionally other therapeutic agents.

Compounds of Formula (I), or a pharmaceutically acceptable salt, solvate, isomer, ester, acid, metabolite or prodrug thereof, as well as the pharmaceutical composition comprising the same, hereinafter referred to as "the substance of the present invention".

The substance of the present invention may be used for treating or preventing FLT3-related conditions, in particular if the conditions respond to an inhibition of a protein tyrosine kinase, especially to an inhibition of wild-type FLT3 kinase or mutant FLT3 kinase. FLT3 mutations include ITD mutations and point mutations, especially FLT3/ITD mutations. The "treatment" in the present invention may be therapeutic (e.g., symptomatic treatment) and/or prophylactic. The substance of the present invention may preferably treat or prevent FLT3-related conditions, and in particular, treating or preventing mutant FLT3/ITD-related conditions is preferred.

In particular, the substance of the present invention may be used for treating or preventing cell proliferative conditions selected from the group consisting of the group consisting of benign or malignant tumors, including but not limited to: initiation or progression of solid tumor, sarcoma, lymphoma (such as B-cell lymphoma, diffuse large B-cell lymphoma, follicular lymphoma, chronic lymphocytic lymphoma, lymphoplasmacytic lymphoma/Waldenström macroglobulinemia, splenic marginal zone lymphoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma), leukemias (such as chronic lymphocytic leukemia, B-cell prolymphocytic leukemia), plasma cell myeloma, plasmacytoma, lymphomatoid granulomatosis, melanoma, B-cell proliferative disease, brain cancer, kidney cancer, liver cancer, adrenal gland cancer, bladder cancer, breast cancer (such as breast ductal carcinoma, lobular carcinoma), stomach neoplasm (including but not limited to stomach cancer), esophagus cancer, ovarian cancer, colorectal cancer, prostate cancer, pancreas cancer, lung cancer, vagina cancer, membranous adenocarcinoma, thyroid cancer, neck cancer, CNS cancer, malignant glioma, myeloproliferative disease, glioblastoma, multiple myeloma, gastrointestinal cancer, colorectal carcinoma, head and neck neoplasms, brain tumor, epidermal hyperplasia, psoriasis, prostate hyperplasia, neoplasia, neoplasia of epithelial character, or similar diseases, or a combination thereof.

The substance of the present invention may preferably be used for treating or preventing FLT3-related conditions, particularly preferably for treating or preventing mutant FLT3/ITD-related conditions, including but not limited to: Hematological malignancies include leukemias, lymphomas (such as non-Hodgkin's lymphoma, Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), adult T-cell ALL, AML with trilineage myelodysplasia (AML/TMDS), mixed lineage leukemia (MLL), myelodysplasia syndromes (MDS), myeloproliferative disorders (MPD), multiple myeloma (MM) and myeloid sarcoma, or similar diseases, or a combination thereof.

Preferably, warm-blooded animals, especially humans, may be administrated via at least one of injection, oral, inhalation, rectal and transdermal administration. The dosage of the active ingredient depends upon features of the individual to be treated (such as age, weight, medical history, individual pharmacokinetic data), disease type and mode of administration.

The substances of the invention may optionally be used in combination with known therapeutic methods, such as administration of other therapeutic agents or radiation therapy. Such other therapeutic agents include, for example, cytostatic agents, other antiproliferative agents and the like.

Other antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, steroids, antiproliferative antibodies, 17-(allylamino)-17-demethoxygeldanamycin (17-AAG) and temozolomide (TMEMODAL).

The term "aromatase inhibitors" as used herein relates to compounds which inhibit the estrogen production by aromatase, and such compounds can suppress the conversion of androstenedione and testosterone. The term includes, but is not limited to steroids, such as exemestane and formestane, and non-steroids, such as aminoglutethimide, vorozole, fadrozole, anastrozole and letrozole, especially letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Aminoglutethimide can be administered, e.g., in the form as it is marketed, e.g. under the trademark ORIMETEN™.

The substances of the invention, when applied in combination with aromatase inhibitors, are particularly useful in treating hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516, or it can be administered, e.g., in the form as it is marketed, e.g. under the trademark FASLODEX™.

The term "topoisomerase I inhibitors" as used herein includes, but is not limited to topotecan, irinotecan, 9-nitrocamptothecin conjugate PNU-166148 (Compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the anthracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing agents including, but not limited to the taxanes paclitaxel and docetaxel, the *vinca* alkaloids, e.g., vinblastine, especially vinblastine sulfate, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity. This includes compounds disclosed in WO 02/22577, especially N-hydroxy-3-[[(2-hydroxyethyl)[2-(1H-indol-3-yl)ethyl]-amino]methyl] phenyl]-2E-2-propenamide, N-hydroxy-3-[[(2-hydroxyethyl)[2-(1H-indol-3-yl)ethyl]-amino]methyl]phenyl]-2E-2-propenamide and pharmaceutically acceptable salts thereof. It further especially includes Suberoylanilide hydroxamic acid (SAHA).

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity, e.g., celecoxib (Celebrex), rofecoxib (Vioxx) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl, c-Kit, FLT3, Insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF comprise those which inhibit VEGF receptor, especially the tyrosine kinase activity of the VEGF receptor, and compounds binding to VEGF, and are in particular those compounds, proteins and monoclonal antibodies generically and specifically disclosed in WO98/35958 (describing compounds of formula I), WO00/09495, WO00/27820, WO00/59509, WO98/11223, WO00/27819, WO01/55114, WO01/58899 and EP0769947; those as described by M. Prewett et al. in Cancer Research 59 (1999) 5209-5218, by Z. Zhu et al. in Cancer Res. 58, 1998, 3209-3214, and by J. Mordenti et al in Toxicologic Pathology, vol. 27, no. 1, pp 14-21, 1999; in WO00/37502 and WO94/10202; Angiostatin™, described by M. S. O'Reilly et al., Cell 79, 1994, 315-328.

Compounds which decrease the activity of EGF are especially compounds which inhibit the binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980.

Compounds which decrease the activity of c-Src include, but are not limited to, compounds inhibiting the c-Src protein tyrosine kinase activity as defined below and to SH2 interaction inhibitors such as those disclosed in WO97/07131 and WO97/08193.

Compounds inhibiting the c-Src protein tyrosine kinase activity include, but are not limited to, compounds belonging to the structure classes of pyrrolopyrimidines, especially pyrrolo[2,3-d]pyrimidines; purines; pyrazolopyrimidines, especially pyrazolo[3,4-d]pyrimidines; and pyridopyrimidines, especially pyrido[2,3-d]pyrimidines. Preferably, the term relates to those compounds disclosed in WO 96/10028, WO 97/28161, WO97/32879 and WO97/49706.

Compounds which decrease the activity of IGF-IR are especially those disclosed in WO02/92599.

Further specific compounds that decrease protein kinase activity and which may also be used in combination with the substances of the present invention are Imatinib (Gleevec/Glivec), PKC412, Iressa™ (ZD1839), AEE788 and a pharmaceutically acceptable salt thereof (see also WO03/13541), PTK787 and a pharmaceutically acceptable salt thereof (see also WO98/35958), ZD6474, GW2016, CH IR-200131, CEP-7055/CEP-5214, CP-547632, KRN-633 and SU5416.

Anti-angiogenic compounds having another mechanism of action than decreasing the protein kinase activity include, but are not limited to e.g. thalidomide (THALOMID), celecoxib (Celebrex), and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, e.g., as disclosed in U.S. Pat. No. 5,843,901.

The term "anti-androgens" as used herein includes, but is not limited to bicalutamide (CASODEX™), which can be formulated, e.g., as disclosed in U.S. Pat. No. 4,636,505.

The term "bengamides" relates to bengamides and derivatives thereof having antiproliferative properties.

The term "bisphosphonates" as used herein includes, but is not limited to etridonic acid, pamidronic acid, and alendronic acid. Etridonic acid can be administered, e.g., in the form as it is marketed, e.g. under the trademark DIDRONEL™. Clodronic acid can be administered, e.g., in the form as it is marketed, e.g. under the trademark BONEFOS™. Tiludronic acid can be administered, e.g., in the form as it is marketed, e.g. under the trademark SKELID™. Pamidronic acid can be administered, e.g., in the form as it is marketed, e.g. under the trademark AREDIA™. Alendronic acid can be administered, e.g., in the form as it is marketed, e.g. under the trademark FOSAMAX™. Ibandronic acid can be administered, e.g., in the form as it is marketed, e.g. under the trademark BONDRANAT™. Risedronic acid can be administered, e.g., in the form as it is marketed, e.g. under the trademark ACTONEL™. Zoledronic acid can be administered, e.g., in the form as it is marketed, e.g. under the trademark ZOMETA™.

The term "steroids" includes hydrocortisone, decadron, methylprednisolone and ponisone.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan), PRO64553 (anti-CD40) and 2C4 Antibody.

For the treatment of AML, compounds of formula (I) can be used in combination with standard leukemia therapies, especially in combination with therapies used for the treatment of AML. In particular, compounds of formula (I) can be administered in combination with e.g. farnesyltransferase inhibitors and/or other drugs used for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula (I) can be prepared and administered as described in the art such as in the documents cited above.

In the embodiments of the invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Preparation of the Compounds

Compounds of formula (I) may be synthesized using standard synthetic techniques known to those of skill in the art or using methods known in the art in combination with methods described herein. In additions, solvents, temperatures and other reaction conditions presented herein may vary according to those of skill in the art.

In certain embodiments, provided herein are methods of making and methods of using kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein and other related compounds having different substituents can be synthesized using techniques and materials known to those of skill in the art. Reactions for the preparation of compounds as disclosed herein may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

Using the synthetic methods described herein, compounds as disclosed herein are obtained in good yields and purity. The compounds prepared by the methods disclosed herein are purified by conventional means known in the art, such as, filtration, recrystallization, chromatography, distillation, and combinations thereof.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

Non-limiting examples of synthetic schemes for the preparation of compounds of Formula (I) are described in Scheme I.

Example 1

Compound 1: 1-(4-(4-amino-3-(4-(2-morpholinoethoxy)phenyl)-1H-pyrazolo[3,4-d]pyrimidin-1-yl)phenyl)-3-(5-(tert-butyl)isoxazol-3-yl)urea

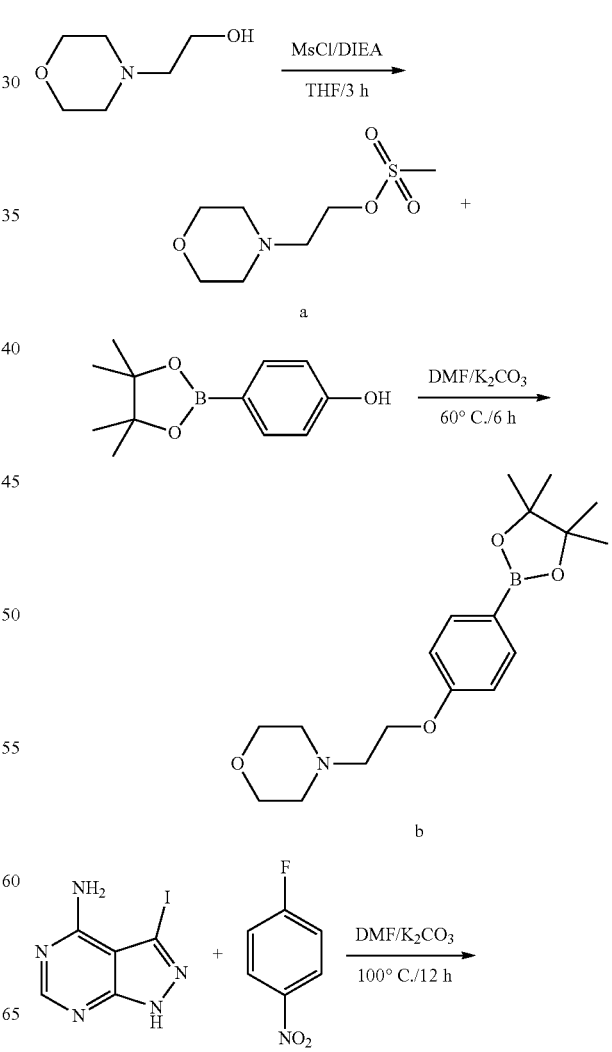

47
-continued
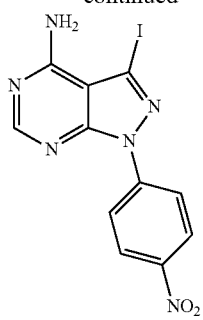
c
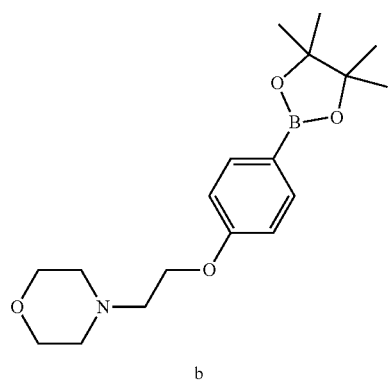
b
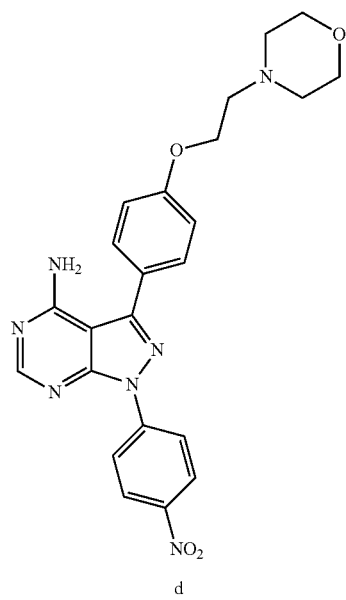
d
48
-continued
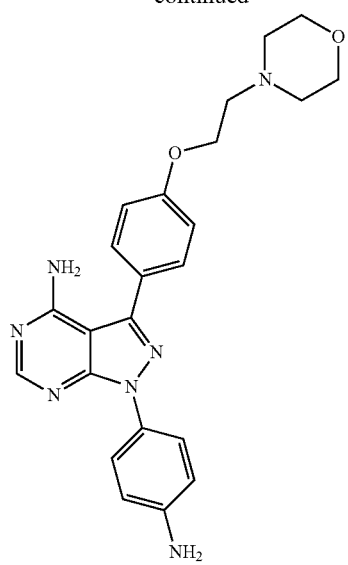
e
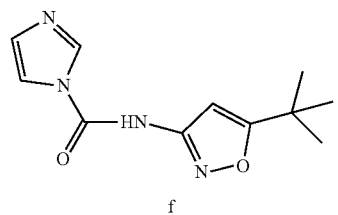
f
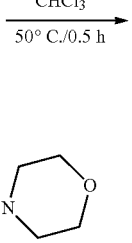
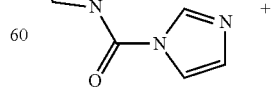
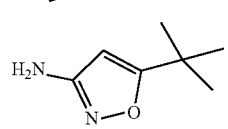

-continued

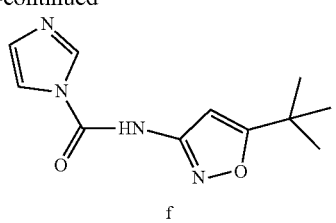

f

Step 1. Synthesis of Compound a: 2-morpholin-ethylmethylsulfone

Compounds 2-morpholinethanol (5 g, 1 eq), N,N-diisopropyl ethylamine (6.4 g, 1 eq) and tetrahydrofuran (20 mL) were mixed and added dropwise with methanesulfonyl chloride (5.3 g, 1 eq) under protection of nitrogen at 0° C. After addition, the mixture was allowed to react at room temperature for 3 h, then diluted with acetyl acetate (400 mL), washed with water and saturated saline solution and further concentrated to yield Compound a for use in subsequent steps.

Step 2. Synthesis of Compound b: 4-((2-morpholine)ethoxy)benzeneboronic Acid Pinacol Ester Compound a (5 g, 1 eq), 4-hydroxyphenylboronic acid pinacol ester (6.3 g, 1.2 eq), potassium carbonate (6.6 g, 2 eq) and N,N-dimethylformamide (50 mL) were mixed and stirred at 60° C. for 6 h, then diluted with ethyl acetate (400 mL), washed with water and saturated saline solution, and further subjected to concentration and column chromatography to yield Compound b (5.5 g) in solid state.

Step 3. Synthesis of Compound c: 3-iodo-1-(4-nitrophenyl)-1H-pyrazolo[3,4-d]pyrimidin-4-amine 3-iodo-1H-pyrazolo[3,4-d]pyrimidin-4-amine (5 g, 1 eq), 1-fluoro-4-nitro-benzene (2.8 g, 1.05 eq), potassium carbonate (7.9 g, 3 eq) and N,N-dimethylformamide (50 mL) were mixed under protection of nitrogen and stirred at 100° C. overnight, then cooled down and poured into water (200 mL), and filtered and dried to obtain Compound c (6 g) in solid state.

Step 4. Synthesis of Compound d: 3-(4-(2-morpholinoethoxy)phenyl)-1-(4-nitrophenyl)-1H-pyrazolo[3,4-d]pyrimidin-4-amine Compound c (5 g, 1 eq), Compound b (4.8 g, 1.1 eq), Pd (PPh$_3$)$_4$ (0.75 g, 0.05 eq), potassium carbonate (3.6 g, 2 eq), 1,4-dioxane/H$_2$O (60 mL, 5/1) were mixed under nitrogen and stirred at 90° C. overnight, then cooled down and poured into water (150 mL), and filtered and dried to obtain Compound d (5.2 g) in solid state.

Step 5. Synthesis of Compound e: 3-(4-(2-morpholinoethoxy)phenyl)-1-(4-aminophenyl)-1H-pyrazolo[3,4-d]pyrimidin-4-amine Compound d (5 g, 1 eq) was dissolved in 50 mL methanol and added with Pd/C (2 g, 5%). The mixture were stirred overnight under hydrogen atmosphere, then subjected to filtration, washed with dichloromethane containing 10% methanol, and further concentrated to obtain Compound e which was directly used for next step.

Step 6. Synthesis of Compound f: N-(5-(tert-butyl)isoxazol-3-yl)-1H-imidazole-1-carboxamide Carbonyldiimidazole (8.7 g, 1 eq) and 1,2-dichloroethane (50 mL) were mixed and added with 3-amino-5-tert-butyl-isoxazole (5 g, 1 eq) at 50° C. under protection of nitrogen, and stirred overnight at this temperature, then cooled down at an ice-water bath and filtered to obtain Compound f (7 g) in solid state.

Step 7. Synthesis of Compound 1: 1-(4-(4-amino-3-(4-(2-morpholinoethoxy)phenyl)-1H-pyrazolo[3,4-d]pyrimidin-1-yl)phenyl)-3-(5-(tert-butyl)isoxazol-3-yl)urea Compound f (0.1 g, 2 eq) and trichloromethane (4 mL) were mixed and added with Compound e (0.1 g, 1 eq) at 50° C., and stirred for 0.5 h at this temperature, then cooled down to 0° C. and stirred for 1 h, and further filtered to obtain Compound 1 in solid state (60 mg in total).

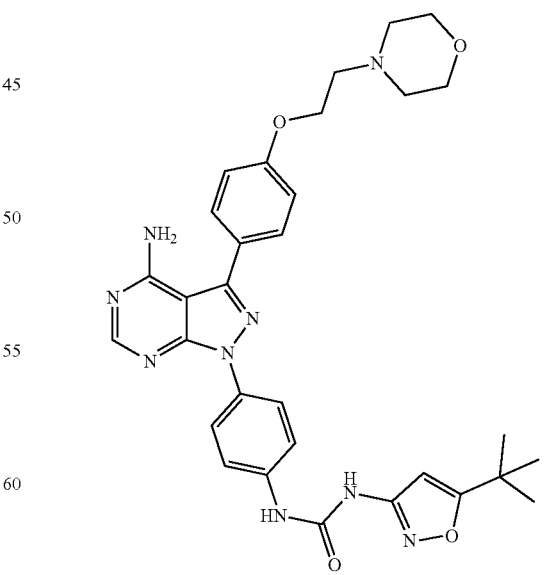

Exact Mass (calculated): 597.28; MS(ESI) m/z (M+1)$^+$: 598.2836.

Example 2

Compound 2: 1-(4-(4-amino-3-(4-(2-morpholinoethoxy)phenyl)-1H-pyrazolo[3,4-d]pyrimidin-1-yl)phenyl)-3-(5-(methyl)isoxazol-3-yl)urea

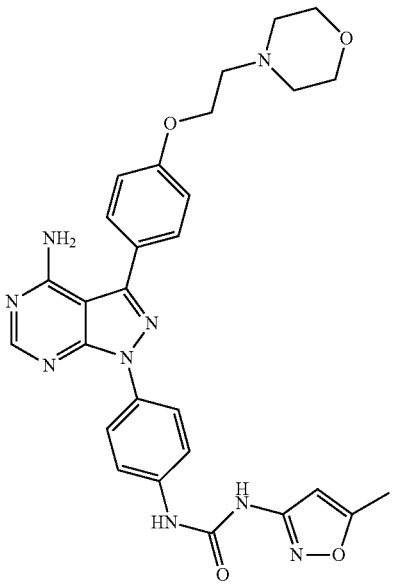 [SMILES: Cc1cc(NC(=O)Nc2ccc(-n3nc(-c4ccc(OCCN5CCOCC5)cc4)c4c(N)ncnc43)cc2)no1]

Synthesis of Compound 2 was accomplished by using procedures similar to that described in Example 1.

Exact Mass (calculated): 555.23; MS(ESI) m/z (M+1)$^+$: 556.2415.

Example 3

Compound 3: 1-(4-(4-amino-3-(4-(2-morpholinoethoxy)phenyl)-1H-pyrazolo[3,4-d]pyrimidin-1-yl)phenyl)-3-(isoxazol-3-yl)urea

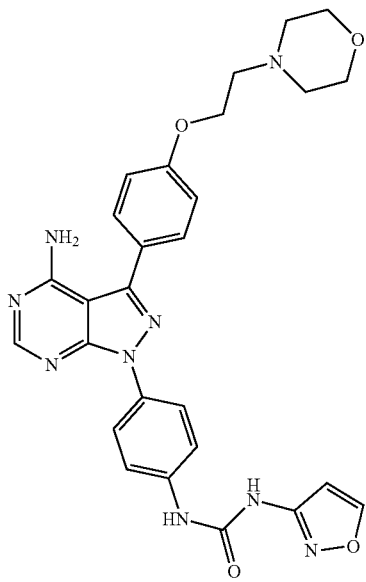 [SMILES: Nc1ncnc2c1c(-c1ccc(OCCN3CCOCC3)cc1)nn2-c1ccc(NC(=O)Nc2ccon2)cc1]

Synthesis of Compound 3 was accomplished by using procedures similar to that described in Example 1.

Exact Mass (calculated): 541.22; MS(ESI) m/z (M+1)$^+$: 542.2245.

Example 4

Compound 4: 1-(4-(4-amino-3-(4-(2-morpholinoethoxy)phenyl)-1H-pyrazolo[3,4-d]pyrimidin-1-yl)phenyl)-3-isobutylurea

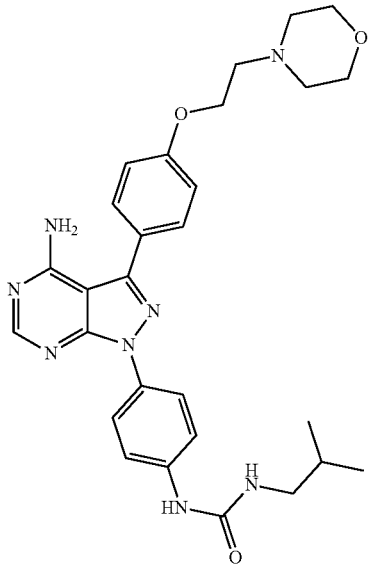 [SMILES: CC(C)CNC(=O)Nc1ccc(-n2nc(-c3ccc(OCCN4CCOCC4)cc3)c3c(N)ncnc32)cc1]

Synthesis of Compound 4 was accomplished by using procedures similar to that described in Example 1.

Exact Mass (calculated): 530.28; MS(ESI) m/z (M+1)$^+$: 531.2865.

Example 5

Compound 5: 1-(4-(4-amino-3-(4-(2-morpholinoethoxy)phenyl)-1H-pyrazolo[3,4-d]pyrimidin-1-yl)phenyl)-3-(2-(dimethylamino)ethyl)urea

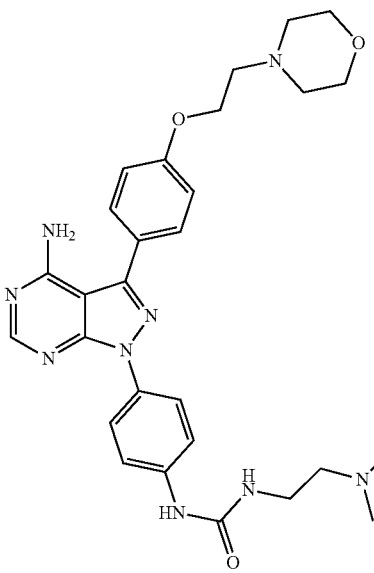

Synthesis of Compound 5 was accomplished by using procedures similar to that described in Example 1.

Exact Mass (calculated): 545.29; MS(ESI) m/z (M+1)$^+$: 546.2943.

Example 6

Compound 6: 1-(4-(4-amino-3-(4-(2-morpholinoethoxy)phenyl)-1H-pyrazolo[3,4-d]pyrimidin-1-yl)-3-methylphenyl)-3-(5-(tert-butyl)isoxazol-3-yl)urea

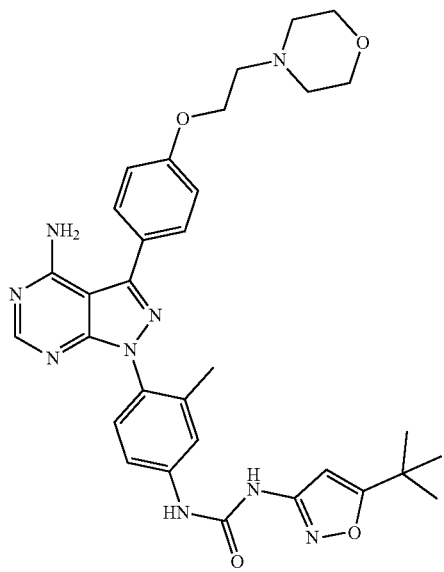 [SMILES: Cc1cc(NC(=O)Nc2cc(C(C)(C)C)on2)ccc1-n1nc(-c2ccc(OCCN3CCOCC3)cc2)c2c(N)ncnc21]

Synthesis of Compound 6 was accomplished by using procedures similar to that described in Example 1.

Exact Mass (calculated): 611.30; MS(ESI) m/z (M+1)$^+$: 612.3059.

Example 7

Compound 7: 1-(4-(4-amino-3-(4-(2-morpholinoethoxy)phenyl)-1H-pyrazolo[3,4-d]pyrimidin-1-yl)-2-methylphenyl)-3-(5-(tert-butyl)isoxazol-3-yl)urea

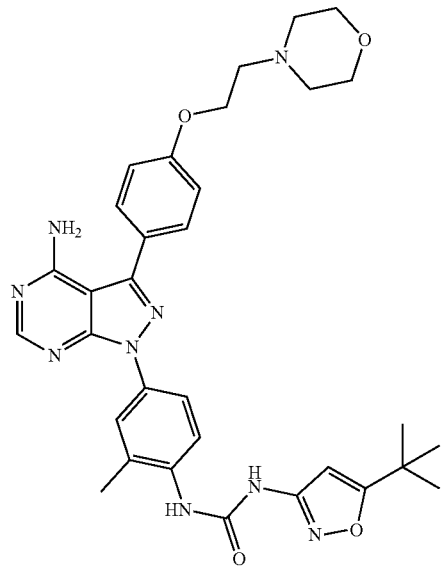 [SMILES: Cc1cc(-n2nc(-c3ccc(OCCN4CCOCC4)cc3)c3c(N)ncnc32)ccc1NC(=O)Nc1cc(C(C)(C)C)on1]

Synthesis of Compound 7 was accomplished by using procedures similar to that described in Example 1.

Exact Mass (calculated): 611.30; MS(ESI) m/z (M+1)$^+$: 612.3055.

Example 8

Compound 8: 1-(4-(4-amino-3-(4-(2-morpholinoethoxy)phenyl)-1H-pyrazolo[3,4-d]pyrimidin-1-yl)phenyl)-3-(4-(tert-butyl)thiazol-2-yl)urea

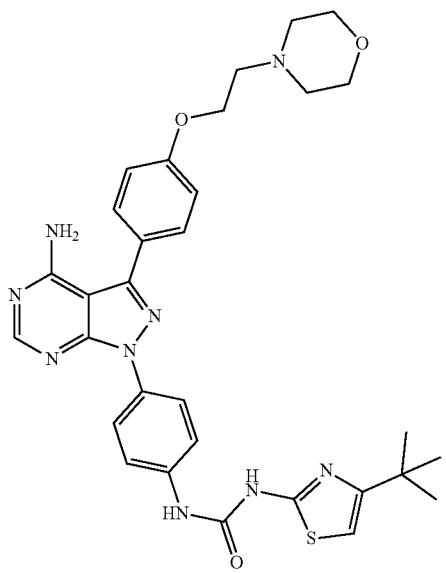 [SMILES: CC(C)(C)c1csc(NC(=O)Nc2ccc(-n3nc(-c4ccc(OCCN5CCOCC5)cc4)c4c(N)ncnc43)cc2)n1]

Synthesis of Compound 8 was accomplished by using procedures similar to that described in Example 1.

Exact Mass (calculated): 613.26; MS(ESI) m/z (M+1)$^+$: 614.2615.

Example 9

Compound 9: 1-(4-(4-amino-3-(4-(2-morpholinoethoxy)phenyl)-1H-pyrazolo[3,4-d]pyrimidin-1-yl)phenyl)-3-(4-(trifluoromethyl)thiazol-2-yl)urea

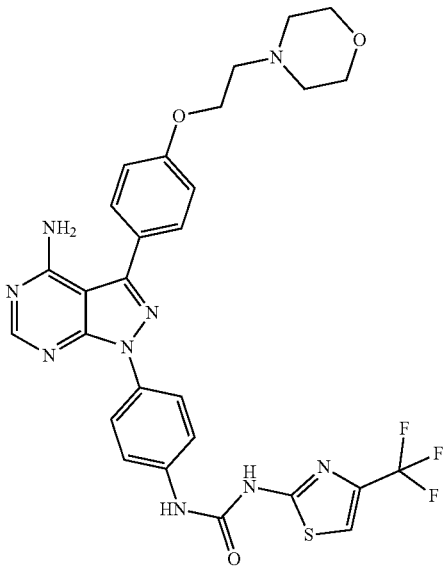 [SMILES: Nc1ncnc2c1c(-c1ccc(OCCN3CCOCC3)cc1)nn2-c1ccc(NC(=O)Nc2nc(C(F)(F)F)cs2)cc1]

Synthesis of Compound 9 was accomplished by using procedures similar to that described in Example 1.

Exact Mass (calculated): 625.18; MS(ESI) m/z (M+1)$^+$: 626.1865.

Example 10

Compound 10: 1-(4-(4-amino-3-(4-(2-morpholino-ethoxy)phenyl)-1H-pyrazolo[3,4-d]pyrimidin-1-yl)phenyl)-3-(4-(tert-butyl)phenyl)urea

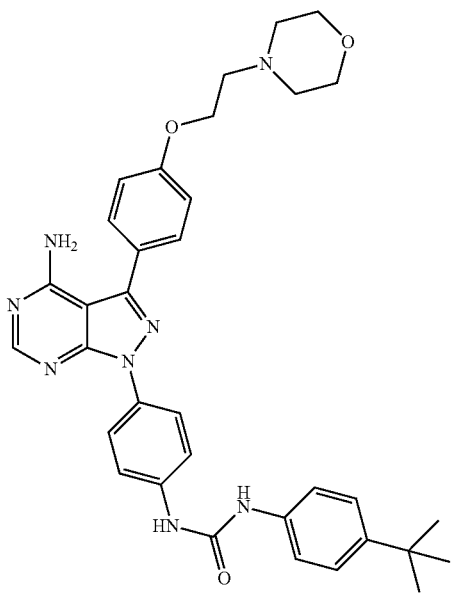 [SMILES: CC(C)(C)c1ccc(NC(=O)Nc2ccc(-n3nc(-c4ccc(OCCN5CCOCC5)cc4)c4c(N)ncnc43)cc2)cc1]

Synthesis of Compound 10 was accomplished by using procedures similar to that described in Example 1.

Exact Mass (calculated): 606.31; MS(ESI) m/z (M+1)$^+$: 607.3124.

Example 11

Compound 11: 1-(4-(4-amino-3-(4-(2-morpholino-ethoxy)phenyl)-1H-pyrazolo[3,4-d]pyrimidin-1-yl)phenyl)-3-(4-methyl-3-(trifluoromethyl)phenyl)urea

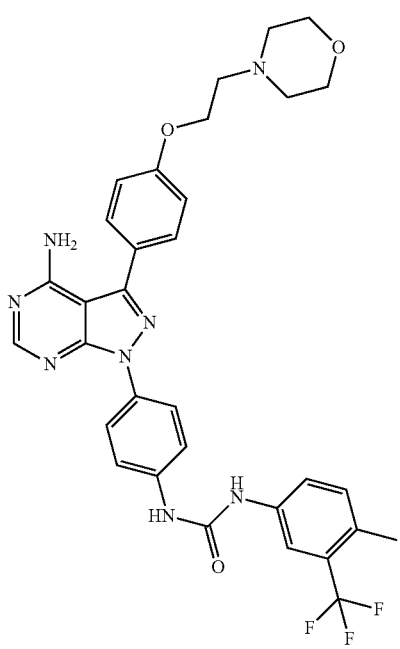 [SMILES: Cc1ccc(NC(=O)Nc2ccc(-n3nc(-c4ccc(OCCN5CCOCC5)cc4)c4c(N)ncnc43)cc2)cc1C(F)(F)F]

Synthesis of Compound 11 was accomplished by using procedures similar to that described in Example 1.

Exact Mass (calculated): 632.25; MS(ESI) m/z (M+1)$^+$: 633.2536.

Example 12

Compound 12: 1-(4-(4-amino-3-(4-(2-morpholino-ethoxy)phenyl)-1H-pyrazolo[3,4-d]pyrimidin-1-yl)phenyl)-3-(4-chloro-3-(trifluoromethyl)phenyl)urea

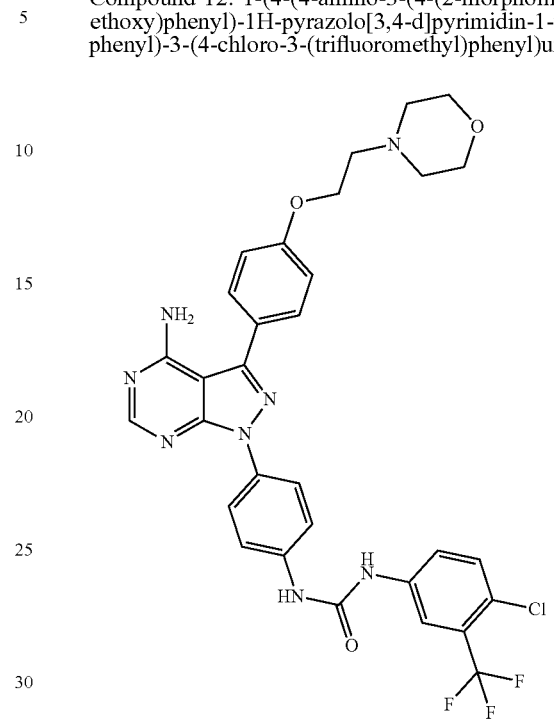

Synthesis of Compound 12 was accomplished by using procedures similar to that described in Example 1.

Exact Mass (calculated): 652.19; MS(ESI) m/z (M+1)$^+$: 653.1928.

Example 13

Compound 13: 1-(4-(4-amino-3-(4-(2-morpholino-ethoxy)phenyl)-1H-pyrazolo[3,4-d]pyrimidin-1-yl)phenyl)-3-(3,4,5-trimethoxylphenyl)urea

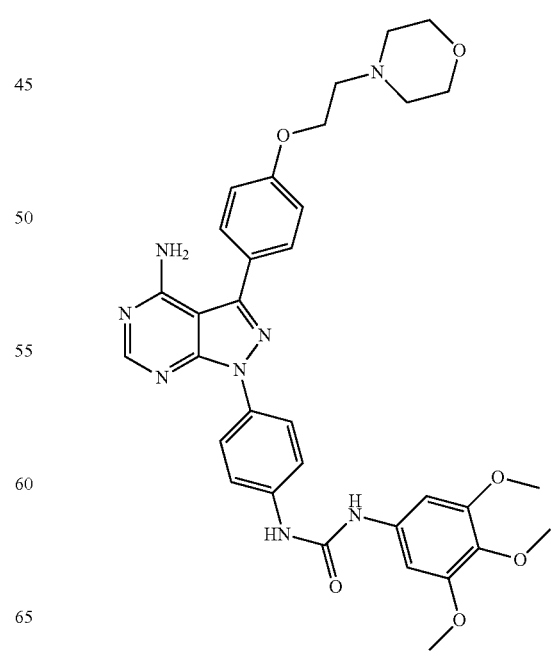

Synthesis of Compound 13 was accomplished by using procedures similar to that described in Example 1.

Exact Mass (calculated): 640.28; MS(ESI) m/z (M+1)+: 641.2860.

Example 14

Compound 14: 1-(4-(4-amino-3-(4-(3-morpholinopropoxy)phenyl)-1H-pyrazolo[3,4-d]pyrimidin-1-yl)phenyl)-3-(5-(tert-butyl)isoxazol-3-yl)urea

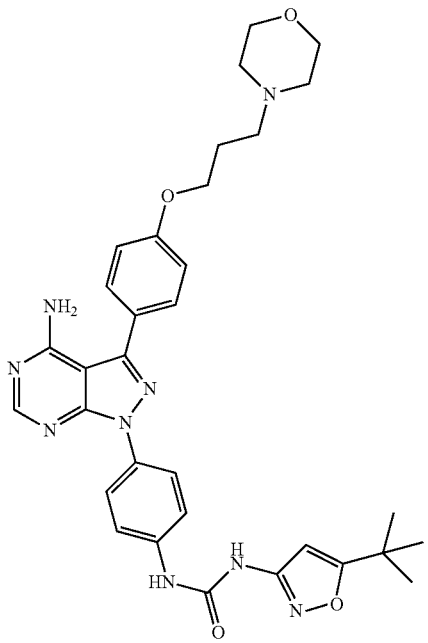 [SMILES: CC(C)(C)c1cc(NC(=O)Nc2ccc(-n3nc(-c4ccc(OCCCN5CCOCC5)cc4)c4c(N)ncnc43)cc2)no1]

Synthesis of Compound 14 was accomplished by using procedures similar to that described in Example 1.

Exact Mass (calculated): 611.30; MS(ESI) m/z (M+1)+: 612.3064.

Example 15

Compound 15: 1-(4-(4-amino-3-(4-(2-piperidin-1-yl)ethoxy)phenyl)-1H-pyrazolo[3,4-d]pyrimidin-1-yl)phenyl)-3-(5-(tert-butyl)isoxazol-3-yl)urea

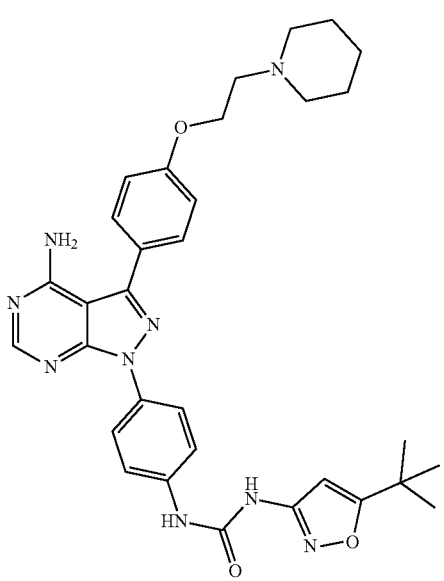

Synthesis of Compound 15 was accomplished by using procedures similar to that described in Example 1.

Exact Mass (calculated): 595.30; MS(ESI) m/z (M+1)+: 596.3075.

Example 16

Compound 16: 1-(4-(4-amino-3-(3-(2-morpholinoethoxy)phenyl)-1H-pyrazolo[3,4-d]pyrimidin-1-yl)phenyl)-3-(5-(tert-butyl)isoxazol-3-yl)urea

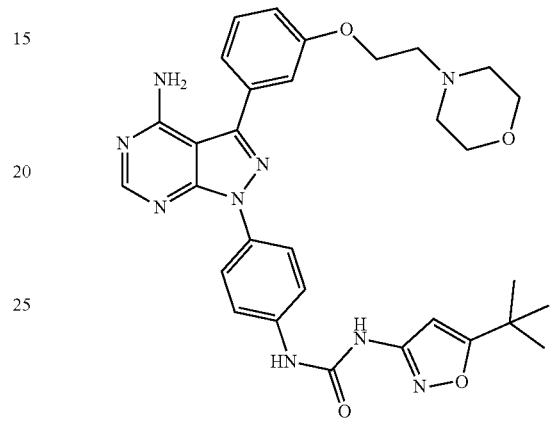

Synthesis of Compound 16 was accomplished by using procedures similar to that described in Example 1.

Exact Mass (calculated): 597.28; MS(ESI) m/z (M+1)+: 598.2862.

Example 17

Compound 17: 1-(3-(4-amino-3-(4-(2-morpholinoethoxy)phenyl)-1H-pyrazolo[3,4-d]pyrimidin-1-yl)phenyl)-3-(5-(tert-butyl)isoxazol-3-yl)urea

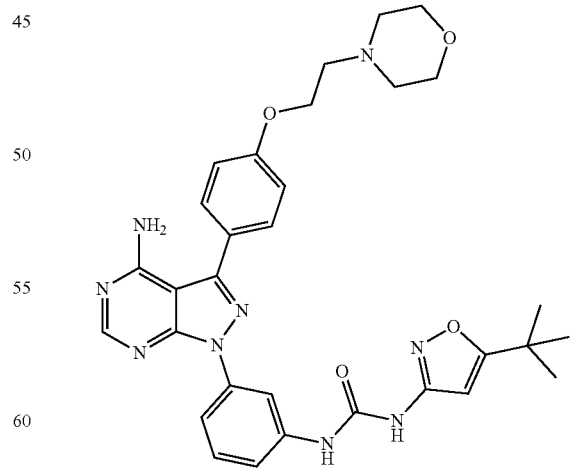

Synthesis of Compound 17 was accomplished by using procedures similar to that described in Example 1.

Exact Mass (calculated): 597.28; MS(ESI) m/z (M+1)+: 598.2858.

Example 18

Compound 18: 1-(4-(4-amino-3-phenyl-1H-pyrazolo[3,4-d]pyrimidin-1-yl)phenyl)-3-(5-(tert-butyl)isoxazol-3-yl)urea

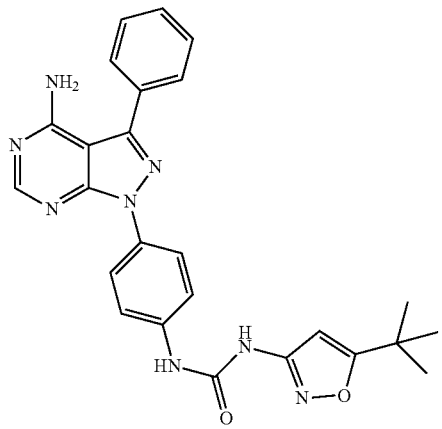 [SMILES: CC(C)(C)c1cc(NC(=O)Nc2ccc(-n3nc(-c4ccccc4)c4c(N)ncnc43)cc2)no1]

Synthesis of Compound 18 was accomplished by using procedures similar to that described in Example 1.

Exact Mass (calculated): 468.20; MS(ESI) m/z (M+1)$^+$: 469.2136.

Example 19

Compound 19: 1-(4-(4-amino-3-(4-(4-methylpiperazin-1-yl)phenyl)-1H-pyrazolo[3,4-d]pyrimidin-1-yl)phenyl)-3-(5-(tert-butyl)isoxazol-3-yl)urea

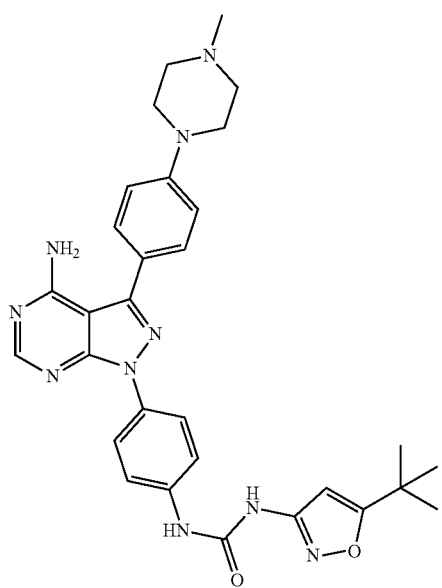 [SMILES: CN1CCN(c2ccc(-c3nn(-c4ccc(NC(=O)Nc5cc(C(C)(C)C)on5)cc4)c4ncnc(N)c34)cc2)CC1]

Synthesis of Compound 19 was accomplished by using procedures similar to that described in Example 1.

Exact Mass (calculated): 566.29; MS(ESI) m/z (M+1)$^+$: 567.2944.

Example 20

Compound 20: 1-(4-(4-amino-3-(4-((4-ethylpiperazin-1-yl)methyl)phenyl)-1H-pyrazolo[3,4-d]pyrimidin-1-yl)phenyl)-3-(5-(tert-butyl)isoxazol-3-yl)urea

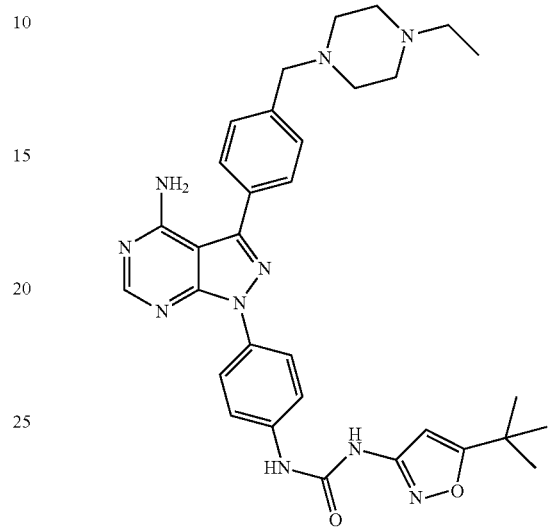

Synthesis of Compound 20 was accomplished by using procedures similar to that described in Example 1.

Exact Mass (calculated): 594.32; MS(ESI) m/z (M+1)$^+$: 595.3266.

Example 21

Compound 21: 1-(4-(3-(4-((4-acetylpiperazin-1-yl)methyl)phenyl)-4amino-1H-pyrazolo[3,4-d]pyrimidin-1-yl)phenyl)-3-(5-(tert-butyl)isoxazol-3-yl)urea

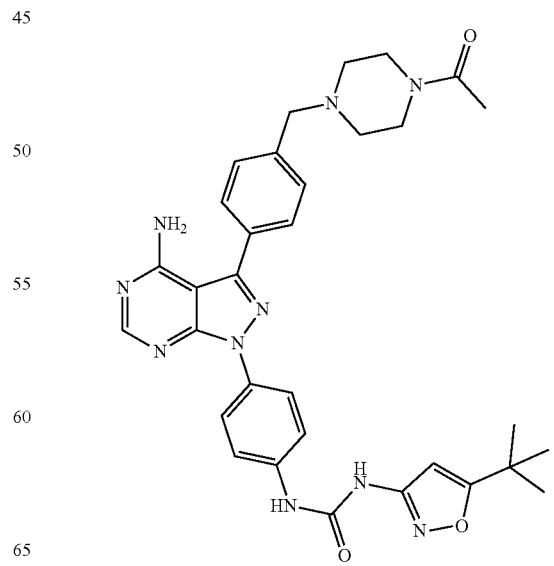

Synthesis of Compound 21 was accomplished by using procedures similar to that described in Example 1.

Exact Mass (calculated): 608.30; MS(ESI) m/z (M+1)$^+$: 609.3078.

Example 22

Compound 22: 1-(4-(4-amino-3-(4-(2-(4-(methane-sulfonyl)piperazin-1-yl)ethoxy)phenyl)-1H-pyrazolo[3,4-d]pyrimidin-1-yl)phenyl)-3-(5-(tert-butyl)isoxazol-3-yl)urea

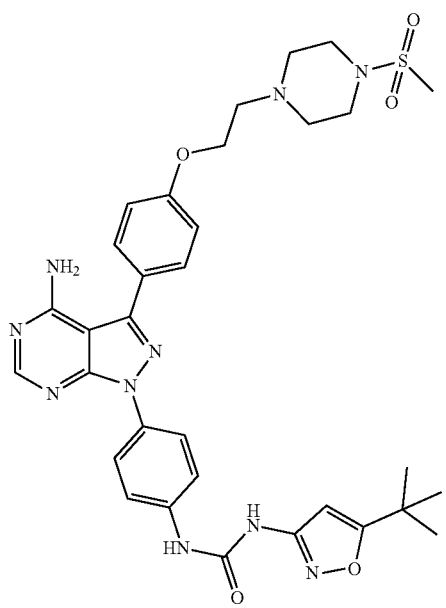 [SMILES: CC(C)(C)c1cc(NC(=O)Nc2ccc(-n3nc(-c4ccc(OCCN5CCN(S(C)(=O)=O)CC5)cc4)c4c(N)ncnc43)cc2)no1]

Synthesis of Compound 22 was accomplished by using procedures similar to that described in Example 1.

Exact Mass (calculated): 674.27; MS(ESI) m/z (M+1)$^+$: 675.2754.

Example 23

Compound 23: 1-(4-(4-amino-3-(4-(morpholinomethyl)phenyl)-1H-pyrazolo[3,4-d]pyrimidin-1-yl)phenyl)-3-(5-(tert-butyl)isoxazol-3-yl)urea

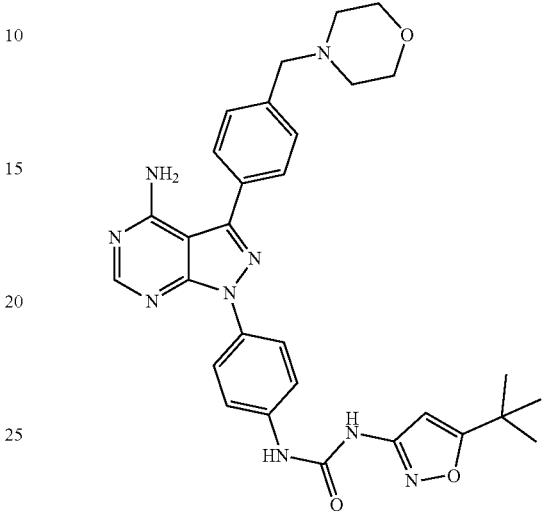

Synthesis of Compound 23 was accomplished by using procedures similar to that described in Example 1.

Exact Mass (calculated): 567.27; MS(ESI) m/z (M+1)$^+$: 568.2748.

Example 24

Compound 24: 1-(4-(4-amino-3-(4-(morpholine-4-carbonyl)phenyl)-1H-pyrazolo[3,4-d]pyrimidin-1-yl)phenyl)-3-(5-(tert-butyl)isoxazol-3-yl)urea

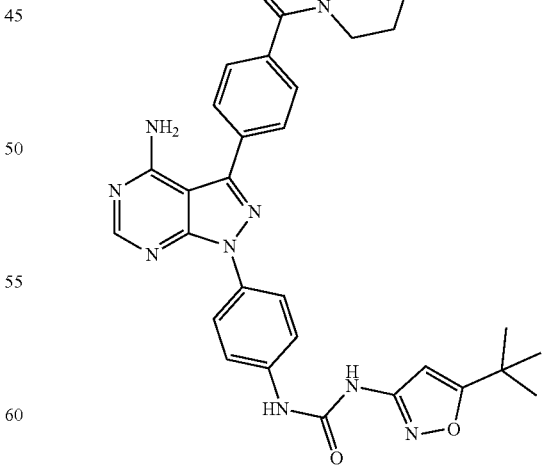

Synthesis of Compound 24 was accomplished by using procedures similar to that described in Example 1.

Exact Mass (calculated): 581.25; MS(ESI) m/z (M+1)$^+$: 582.2563.

Example 25

Compound 25: 1-(4-(4-amino-3-(4-(2-morpholino-2-oxoethyl)phenyl)-1H-pyrazolo[3,4-d]pyrimidin-1-yl)phenyl)-3-(5-(tert-butyl)isoxazol-3-yl)urea

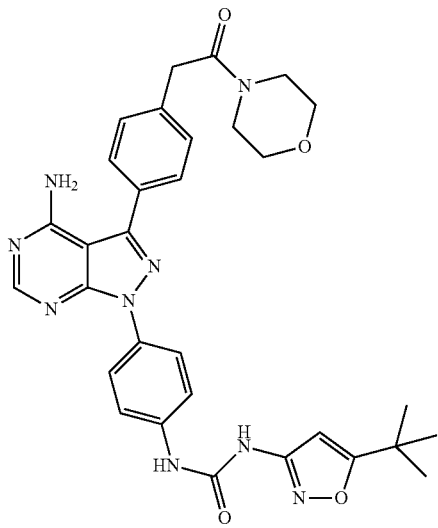 [SMILES: CC(C)(C)c1cc(NC(=O)Nc2ccc(-n3nc(-c4ccc(CC(=O)N5CCOCC5)cc4)c4c(N)ncnc43)cc2)no1]

Synthesis of Compound 25 was accomplished by using procedures similar to that described in Example 1.

Exact Mass (calculated): 595.27; MS(ESI) m/z (M+1)$^+$: 596.2715.

Example 26

Compound 26: 1-(4-(4-amino-3-(pyridin-3-yl)-1H-pyrazolo[3,4-d]pyrimidin-1-yl)phenyl)-3-(5-(tert-butyl)isoxazol-3-yl)urea

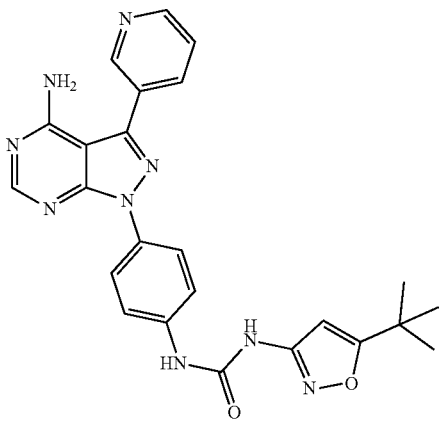 [SMILES: CC(C)(C)c1cc(NC(=O)Nc2ccc(-n3nc(-c4cccnc4)c4c(N)ncnc43)cc2)no1]

Synthesis of Compound 26 was accomplished by using procedures similar to that described in Example 1.

Exact Mass (calculated): 469.20; MS(ESI) m/z (M+1)$^+$: 467.2061.

Example 27

Compound 27: N-(4-(4-amino-1-(4-(3-(5-(tert-butyl)isoxazol-3-yl)ureido)phenyl)-1H-pyrazolo[3,4-c]pyrimidin-3-yl)phenyl)methanesulfonamide

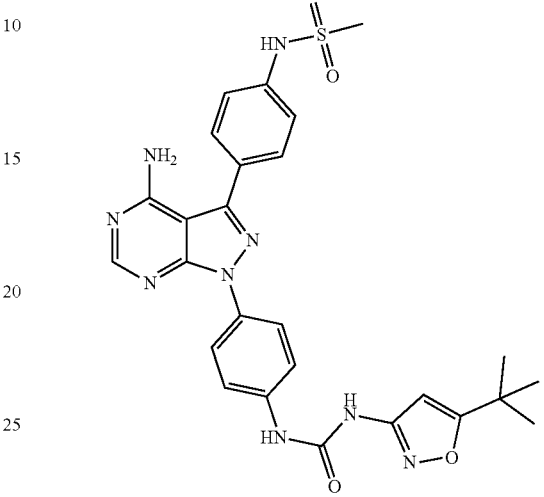

Synthesis of Compound 27 was accomplished by using procedures similar to that described in Example 1.

Exact Mass (calculated): 561.19; MS(ESI) m/z (M+1)$^+$: 562.1976.

Example 28

Compound 28: 1-(4-(4-amino-3-(6-morpholinopyridin-3-yl)-1H-pyrazolo[3,4-d]pyrimidin-1-yl)phenyl)-3-(5-(tert-butyl)isoxazol-3-yl)urea

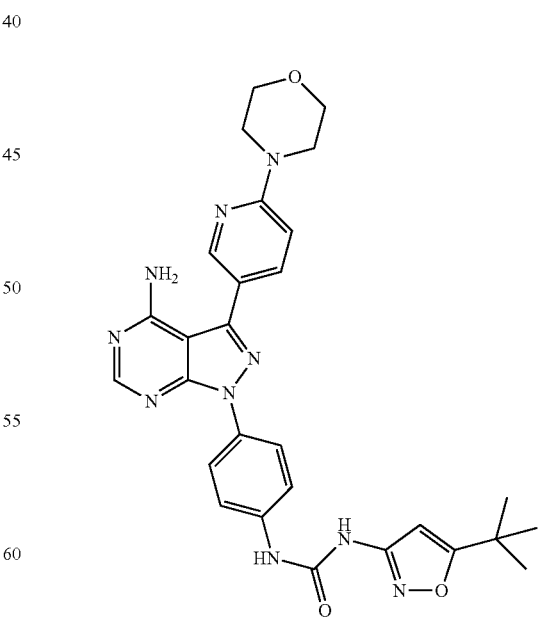

Synthesis of Compound 28 was accomplished by using procedures similar to that described in Example 1.

Exact Mass (calculated): 554.25; MS(ESI) m/z (M+1)$^+$: 555.2578.

Example 29

Compound 29: 1-(4-(4-amino-3-(4-morpholinophenyl)-1H-pyrazolo[3,4-d]pyrimidin-1-yl)phenyl)-3-(5-(tert-butyl)isoxazol-3-yl)urea

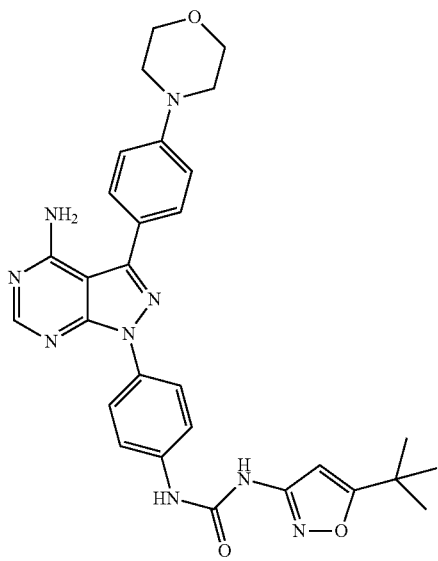 [SMILES: CC(C)(C)c1cc(NC(=O)Nc2ccc(-n3nc(-c4ccc(N5CCOCC5)cc4)c4c(N)ncnc43)cc2)no1]

Synthesis of Compound 29 was accomplished by using procedures similar to that described in Example 1.

Exact Mass (calculated): 553.25; MS(ESI) m/z (M+1)$^+$: 554.2561.

Example 30

Compound 30: 1-(4-(4-amino-3-(4-phenoxylphenyl)-1H-pyrazolo[3,4-d]pyrimidin-1-yl)phenyl)-3-(5-(tert-butyl)isoxazol-3-yl)urea

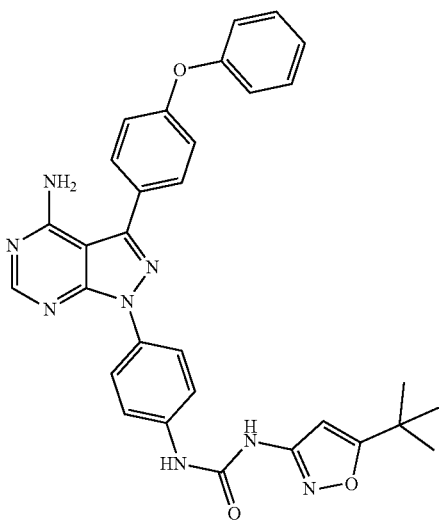 [SMILES: CC(C)(C)c1cc(NC(=O)Nc2ccc(-n3nc(-c4ccc(Oc5ccccc5)cc4)c4c(N)ncnc43)cc2)no1]

Synthesis of Compound 30 was accomplished by using procedures similar to that described in Example 1.

Exact Mass (calculated): 561.23; MS(ESI) m/z (M+1)$^+$: 562.2379.

Example 31

Compound 31: 1-(4-(4-amino-3-(pyridin-4-yl)-1H-pyrazolo[3,4-d]pyrimidin-1-yl)phenyl)-3-(5-(tert-butyl)isoxazol-3-yl)urea

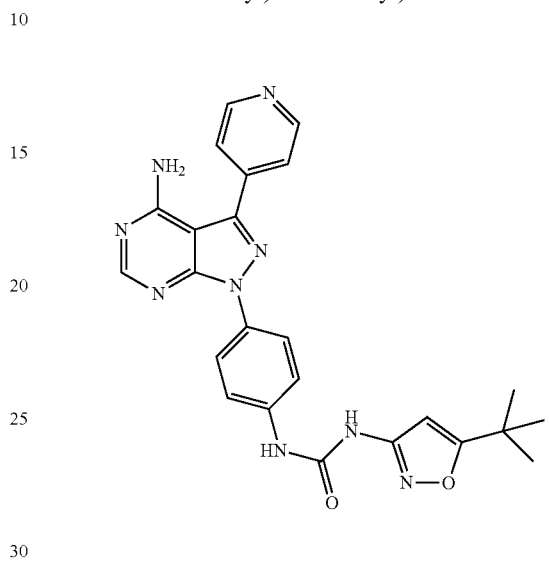

Synthesis of Compound 31 was accomplished by using procedures similar to that described in Example 1.

Exact Mass (calculated): 469.20; MS(ESI) m/z (M+1)$^+$: 470.2026.

Example 32

Compound 32: 1-(4-(4-amino-3-(4-(methanesulfonyl)phenyl)-1H-pyrazolo[3,4-d]pyrimidin-1-yl)phenyl)-3-(5-(tert-butyl)isoxazol-3-yl)urea

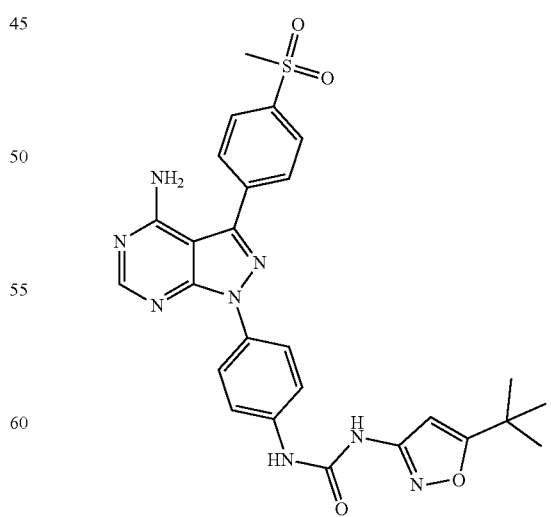

Synthesis of Compound 32 was accomplished by using procedures similar to that described in Example 1.

Exact Mass (calculated): 546.18; MS(ESI) m/z (M+1)⁺: 547.1538.

Example 33

Compound 33: 4-(4-amino-1-(4-(3-(5-(tert-butyl)isoxazol-3-yl)urea)phenyl)-1H-pyrazolo[3,4-d]pyrimidin-3-yl)benzenesulfonamide

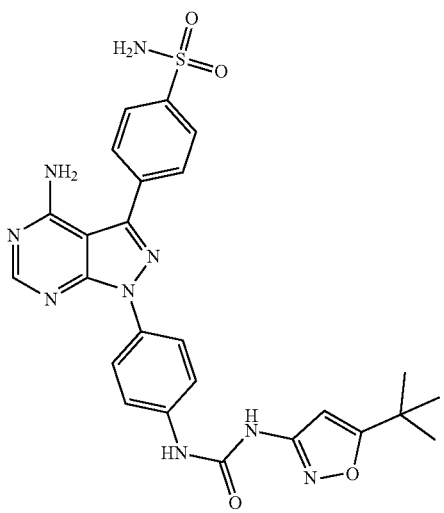 [SMILES: CC(C)(C)c1cc(NC(=O)Nc2ccc(-n3nc(-c4ccc(S(N)(=O)=O)cc4)c4c(N)ncnc43)cc2)no1]

Synthesis of Compound 33 was accomplished by using procedures similar to that described in Example 1.

Exact Mass (calculated): 547.18; MS(ESI) m/z (M+1)⁺: 548.1856.

Example 34

Compound 34: 4-(4-amino-1-(4-(3-(5-(tert-butyl)isoxazol-3-yl)urea)phenyl)-1H-pyrazolo[3,4-c]pyrimidin-3-yl)-N,N-dimethylbenzenesulfonamide

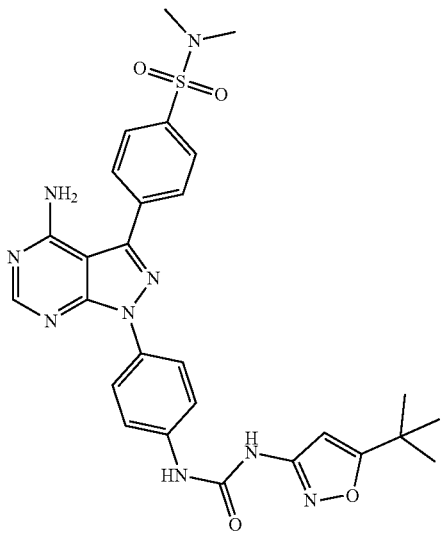 [SMILES: CN(C)S(=O)(=O)c1ccc(-c2nn(-c3ccc(NC(=O)Nc4cc(C(C)(C)C)on4)cc3)c3ncnc(N)c23)cc1]

Synthesis of Compound 34 was accomplished by using procedures similar to that described in Example 1.

Exact Mass (calculated): 575.21; MS(ESI) m/z (M+1)⁺: 576.2176.

Example 35

Compound 35: 1-(4-(4-amino-3-(4-(isobutylsulfonyl)phenyl)-1H-pyrazolo[3,4-c]pyrimidin-1-yl)phenyl)-3-(5-(tert-butyl)isoxazol-3-yl)urea Synthesis of Compound 35 was accomplished by using procedures similar to that described in Example 1.

Exact Mass (calculated): 588.23; MS(ESI) m/z (M+1)⁺: 589.2355.

Example 36

Compound 36: 1-(4-(4-amino-3-(4-(piperazin-1-yl)phenyl)-1H-pyrazolo[3,4-d]pyrimidin-1-yl)phenyl)-3-(5-(tert-butyl)isoxazol-3-yl)urea Synthesis of Compound 36 was accomplished by using procedures similar to that described in Example 1.

Exact Mass (calculated): 552.27; MS(ESI) m/z (M+1)+: 553.2782.

Example 37

Compound 37: 1-(4-(3-(4-(4-ethylpiperazin-1-yl)phenyl)-4-amino-1H-pyrazolo[3,4-d]pyrimidin-1-yl)phenyl)-3-(5-(tert-butyl)isoxazol-3-yl)urea

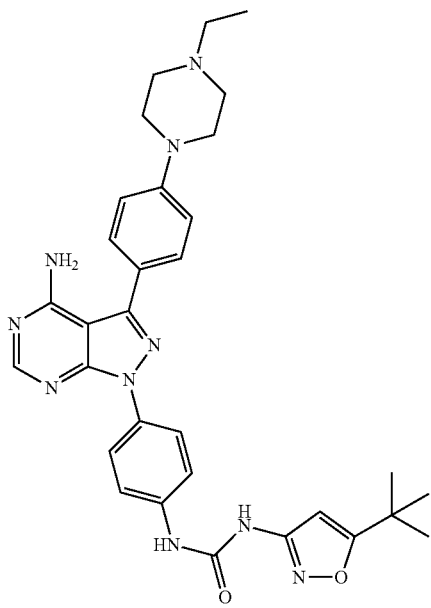 [SMILES: CCN1CCN(c2ccc(-c3nn(-c4ccc(NC(=O)Nc5cc(C(C)(C)C)on5)cc4)c4ncnc(N)c34)cc2)CC1]

Synthesis of Compound 37 was accomplished by using procedures similar to that described in Example 1.
Exact Mass (calculated): 580.30; MS(ESI) m/z (M+1)+: 581.3067.

Example 38

Compound 38: 1-(4-(3-(4-(4-acetylpiperazin-1-yl)phenyl)-4-amino-1H-pyrazolo[3,4-d]pyrimidin-1-yl)phenyl)-3-(5-(tert-butyl)isoxazol-3-yl)urea

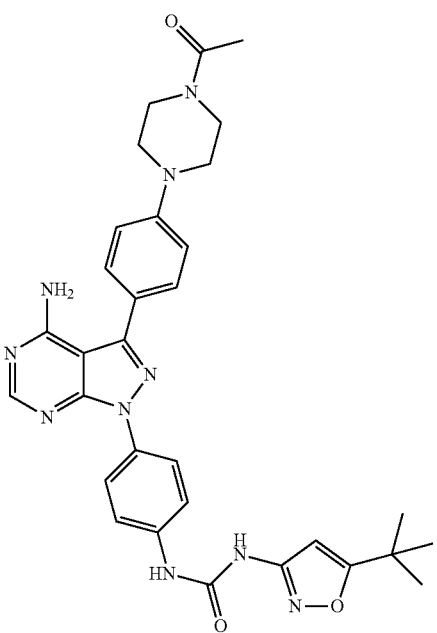 [SMILES: CC(=O)N1CCN(c2ccc(-c3nn(-c4ccc(NC(=O)Nc5cc(C(C)(C)C)on5)cc4)c4ncnc(N)c34)cc2)CC1]

Synthesis of Compound 38 was accomplished by using procedures similar to that described in Example 1.
Exact Mass (calculated): 594.28; MS(ESI) m/z (M+1)+: 595.2877.

Example 39

Compound 39: 1-(4-(4-amino-3-(4-(3-morpholino-3-oxo-propyl)phenyl)-1H-pyrazolo[3,4-d]pyrimidin-1-yl)phenyl)-3-(5-(tert-butyl)isoxazol-3-yl)urea

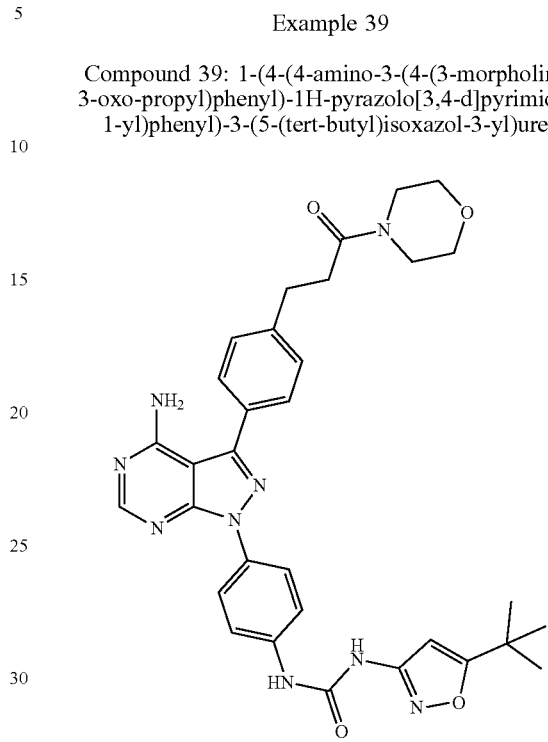

Synthesis of Compound 39 was accomplished by using procedures similar to that described in Example 1.
Exact Mass (calculated): 609.28; MS(ESI) m/z (M+1)+: 610.2875.

Example 40

Compound 40: 1-(4-(4-amino-3-(4-(3-(4-ethylpiperazin-1-yl)-3-oxo-propyl)phenyl)-1H-pyrazolo[3,4-d]pyrimidin-1-yl)phenyl)-3-(5-(tert-butyl)isoxazol-3-yl)urea

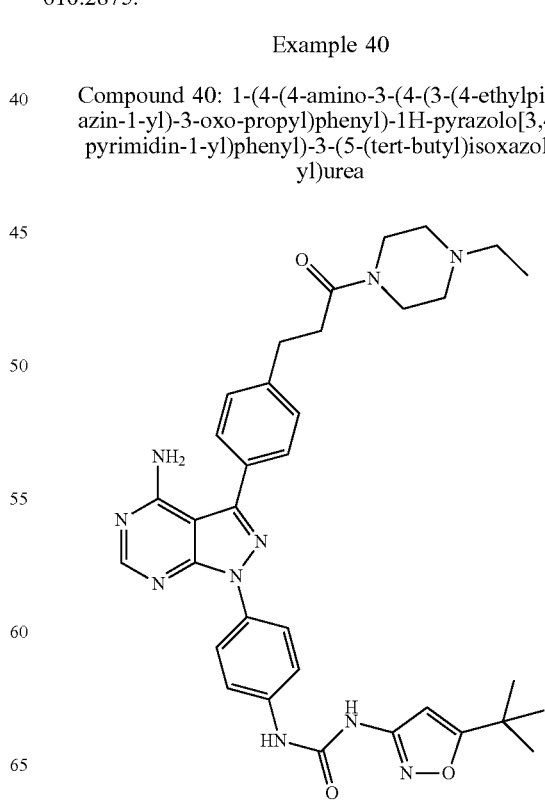

Synthesis of Compound 40 was accomplished by using procedures similar to that described in Example 1.

Exact Mass (calculated): 636.33; MS(ESI) m/z (M+1)$^+$: 637.3389.

Example 41

Compound 41: 1-(4-(4-amino-3-(4-((4-methylpiperazin-1-yl)methyl)phenyl)-1H-pyrazolo[3,4-d]pyrimidin-1-yl)phenyl)-3-(5-(tert-butyl)isoxazol-3-yl)urea

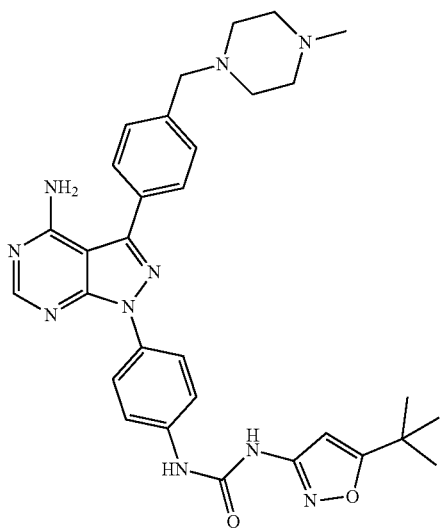 [SMILES: CN1CCN(Cc2ccc(-c3nn(-c4ccc(NC(=O)Nc5cc(C(C)(C)C)on5)cc4)c4ncnc(N)c34)cc2)CC1]

Synthesis of Compound 41 was accomplished by using procedures similar to that described in Example 1.

Exact Mass (calculated): 580.30; MS(ESI) m/z (M+1)$^+$: 581.3056.

Example 42

Compound 42: 1-(4-(4-amino-3-(4-(2-(4-methylpiperazin-1-yl)ethoxy)phenyl)-1H-pyrazolo[3,4-d]pyrimidin-1-yl)phenyl)-3-(5-(tert-butyl)isoxazol-3-yl)urea

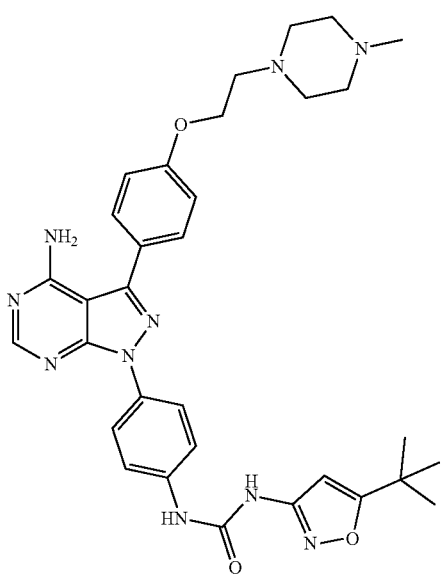 [SMILES: CN1CCN(CCOc2ccc(-c3nn(-c4ccc(NC(=O)Nc5cc(C(C)(C)C)on5)cc4)c4ncnc(N)c34)cc2)CC1]

Synthesis of Compound 42 was accomplished by using procedures similar to that described in Example 1.

Exact Mass (calculated): 610.31; MS(ESI) m/z (M+1)$^+$: 611.3191.

Example 43

Compound 43: 1-(4-(4-amino-3-(4-(2-morpholinomethoxyl)phenyl)-1H-pyrazolo[3,4-d]pyrimidin-1-yl)phenyl)-3-(5-(tert-butyl)isoxazol-3-yl)urea

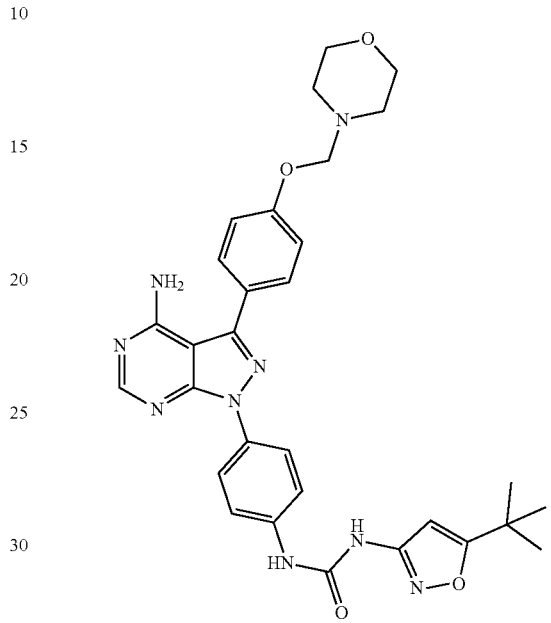

Synthesis of Compound 43 was accomplished by using procedures similar to that described in Example 1.

Exact Mass (calculated): 583.27; MS(ESI) m/z (M+1)$^+$: 584.2748.

Example 44

Compound 44: 1-(4-(4-amino-3-(4-((4-methylpiperidin-1-yl)methyl)phenyl)-1H-pyrazolo[3,4-d]pyrimidin-1-yl)phenyl)-3-(5-(tert-butyl)isoxazol-3-yl)urea

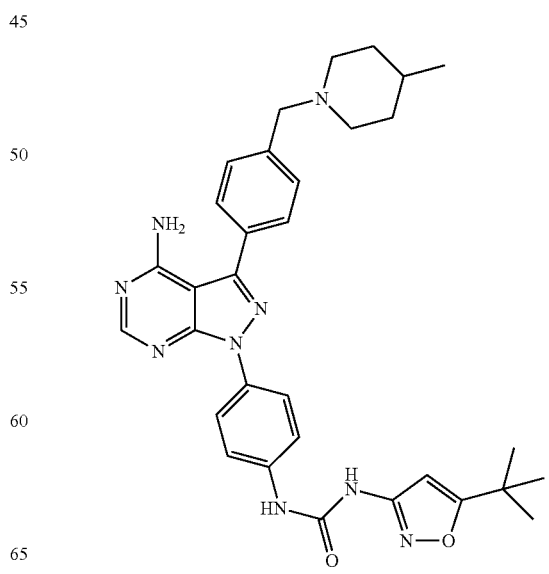

Synthesis of Compound 44 was accomplished by using procedures similar to that described in Example 1.

Exact Mass (calculated): 579.31; MS(ESI) m/z (M+1)+: 580.3172.

Example 45

Compound 45: 1-(4-(4-amino-3-(4-(4-ethylpiperazin-1-carbonyl)phenyl)-1H-pyrazolo[3,4-d]pyrimidin-1-yl)phenyl)-3-(5-(tert-butyl)isoxazol-3-yl)urea

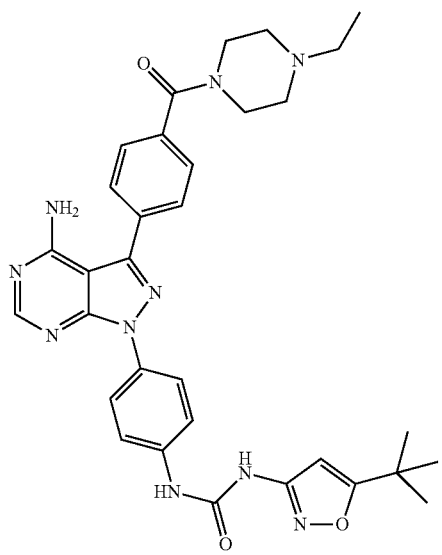 [SMILES: CCN1CCN(C(=O)c2ccc(-c3nn(-c4ccc(NC(=O)Nc5cc(C(C)(C)C)on5)cc4)c4ncnc(N)c34)cc2)CC1]

Synthesis of Compound 45 was accomplished by using procedures similar to that described in Example 1.

Exact Mass (calculated): 608.30; MS(ESI) m/z (M+1)+: 609.3044.

Example 46

Compound 46: 1-(4-(4-amino-3-(4-(piperidin-1-carbonyl)phenyl)-1H-pyrazolo[3,4-d]pyrimidin-1-yl)phenyl)-3-(5-(tert-butyl)isoxazol-3-yl)urea

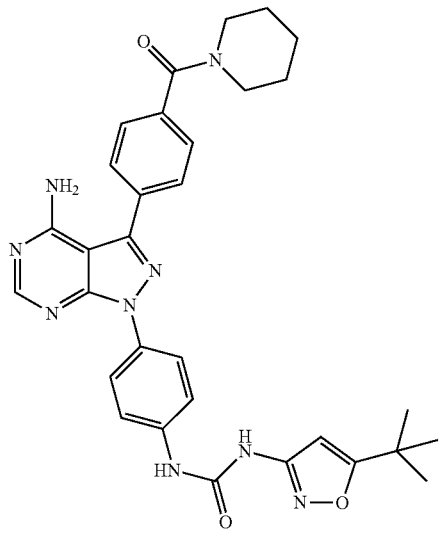 [SMILES: CC(C)(C)c1cc(NC(=O)Nc2ccc(-n3nc(-c4ccc(C(=O)N5CCCCC5)cc4)c4c(N)ncnc43)cc2)no1]

Synthesis of Compound 46 was accomplished by using procedures similar to that described in Example 1.

Exact Mass (calculated): 579.27; MS(ESI) m/z (M+1)+: 580.2749.

Example 47

Compound 47: 1-(4-(4-amino-1-(4-(3-(5-(tert-butyl)isoxazol-3-yl)ureido)phenyl)-1H-pyrazolo[3,4-c]pyrimidin-3-yl)benzyl)piperidin-4-carboxamide

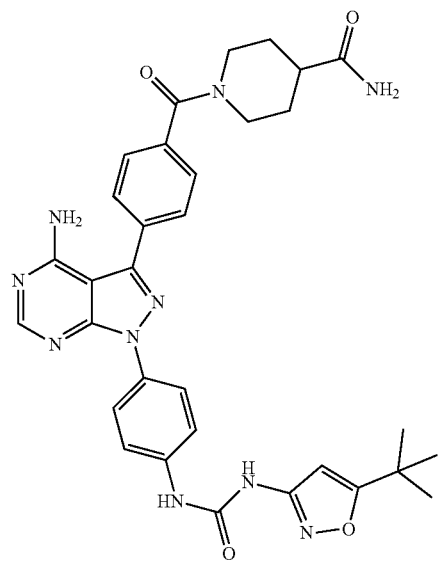 [SMILES: CC(C)(C)c1cc(NC(=O)Nc2ccc(-n3nc(-c4ccc(C(=O)N5CCC(C(N)=O)CC5)cc4)c4c(N)ncnc43)cc2)no1]

Synthesis of Compound 47 was accomplished by using procedures similar to that described in Example 1.

Exact Mass (calculated): 622.28; MS(ESI) m/z (M+1)+: 623.2867.

Example 48

Compound 48: 1-(4-(4-amino-3-(4-(4-isopropylpiperazin-1-carbonyl)phenyl)-1H-pyrazolo[3,4-d]pyrimidin-1-yl)phenyl)-3-(5-(tert-butyl)isoxazol-3-yl)urea

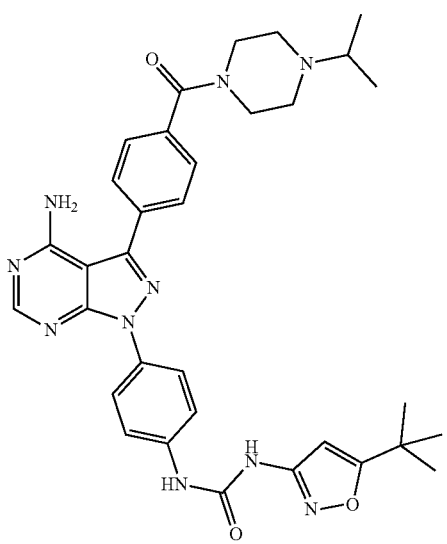 [SMILES: CC(C)N1CCN(C(=O)c2ccc(-c3nn(-c4ccc(NC(=O)Nc5cc(C(C)(C)C)on5)cc4)c4ncnc(N)c34)cc2)CC1]

Synthesis of Compound 48 was accomplished by using procedures similar to that described in Example 1.

Exact Mass (calculated): 622.31; MS(ESI) m/z (M+1)$^+$: 623.3172.

Example 49

Compound 49: 4-(4-amino-1-(4-(3-(5-(tert-butyl)isoxazol-3-yl)ureido)phenyl)-1H-pyrazolo[3,4-d]pyrimidin-3-yl)-N-(tetrahydro-2H-pyran-4-yl)benzamide

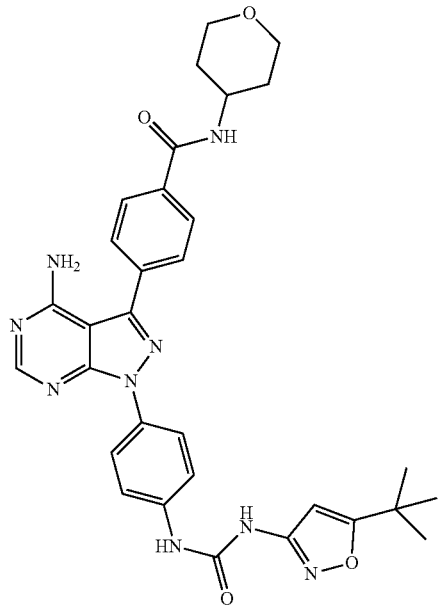 [SMILES: CC(C)(C)c1cc(NC(=O)Nc2ccc(-n3nc(-c4ccc(C(=O)NC5CCOCC5)cc4)c4c(N)ncnc43)cc2)no1]

Synthesis of Compound 49 was accomplished by using procedures similar to that described in Example 1.

Exact Mass (calculated): 595.27; MS(ESI) m/z (M+1)$^+$: 596.2748.

Example 50

Compound 50: 4-(4-amino-1-(4-(3-(5-(tert-butyl)isoxazol-3-yl)ureido)phenyl)-1H-pyrazolo[3,4-c]pyrimidin-3-yl)-N-morpholinbenzamide

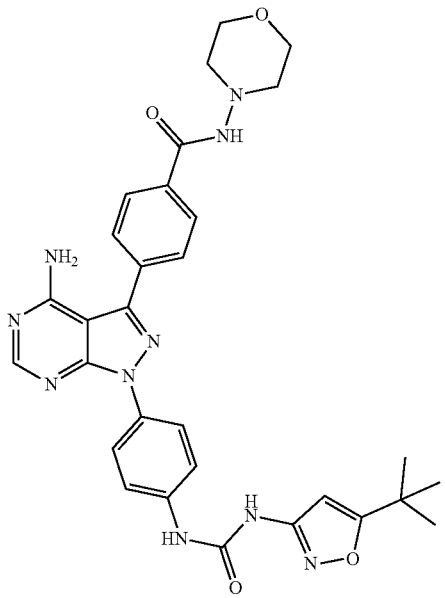

Synthesis of Compound 50 was accomplished by using procedures similar to that described in Example 1.

Exact Mass (calculated): 596.26; MS(ESI) m/z (M+1)$^+$: 597.2638.

Example 51

Compound 51: 4-(4-amino-1-(4-(3-(5-(tert-butyl)isoxazol-3-yl)ureido)phenyl)-1H-pyrazolo[3,4-c]pyrimidin-3-yl)benzamide

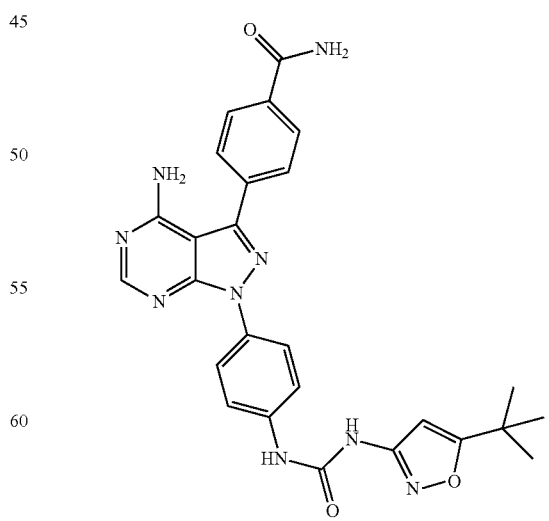

Synthesis of Compound 51 was accomplished by using procedures similar to that described in Example 1.

Exact Mass (calculated): 511.21; MS(ESI) m/z (M+1)+: 512.2178.

Example 52

Compound 52: 4-(4-amino-1-(4-(3-(5-(tert-butyl)isoxazol-3-yl)ureido)phenyl)-1H-pyrazolo[3,4-d]pyrimidin-3-yl)-N-methylbenzamide

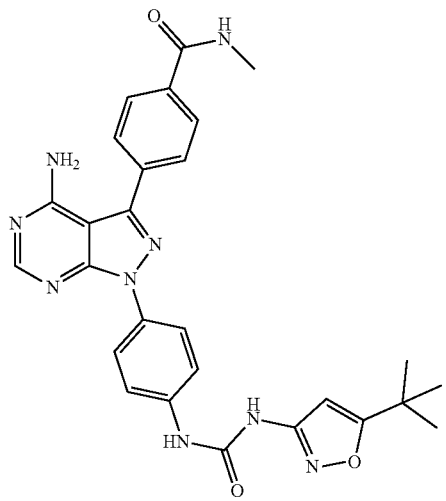 [SMILES: CNC(=O)c1ccc(-c2nn(-c3ccc(NC(=O)Nc4cc(C(C)(C)C)on4)cc3)c3ncnc(N)c23)cc1]

Synthesis of Compound 52 was accomplished by using procedures similar to that described in Example 1.
Exact Mass (calculated): 525.22; MS(ESI) m/z (M+1)+: 526.2294.

Example 53

Compound 53: 4-(4-amino-1-(4-(3-(5-(tert-butyl)isoxazol-3-yl)ureido)phenyl)-1H-pyrazolo[3,4-c]pyrimidin-3-yl)-N-dimethylbenzamide

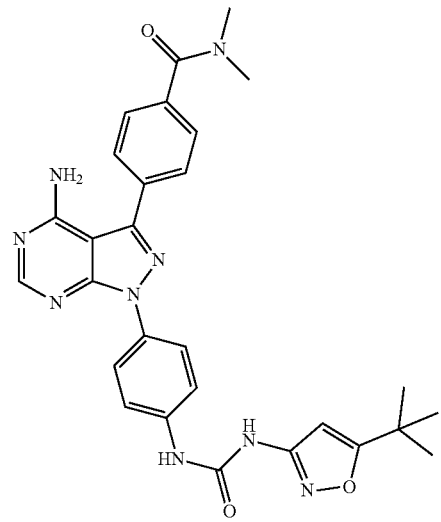 [SMILES: CN(C)C(=O)c1ccc(-c2nn(-c3ccc(NC(=O)Nc4cc(C(C)(C)C)on4)cc3)c3ncnc(N)c23)cc1]

Synthesis of Compound 53 was accomplished by using procedures similar to that described in Example 1.

Exact Mass (calculated): 539.24; MS(ESI) m/z (M+1)+: 540.2466.

Example 54

Compound 54: 1-(4-(4-amino-3-(4-(dimethylamino)phenyl)-1H-pyrazolo[3,4-d]pyrimidin-1-yl)phenyl)-3-(5-(tert-butyl)isoxazol-3-yl)urea

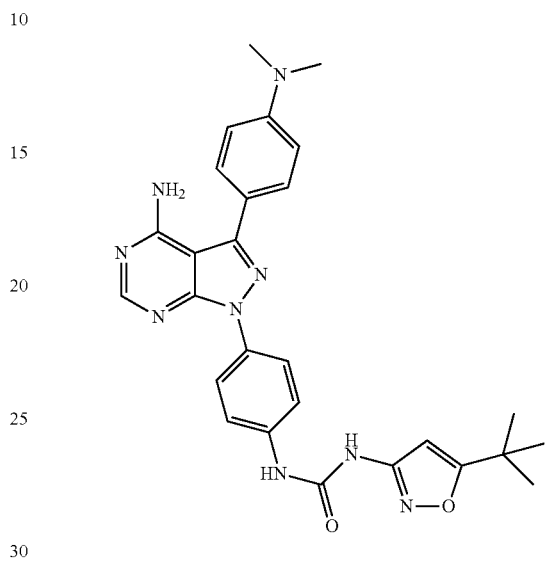

Synthesis of Compound 54 was accomplished by using procedures similar to that described in Example 1.
Exact Mass (calculated): 511.24; MS(ESI) m/z (M+1)+: 512.2485.

Example 55

Compound 55: N-(4-(4-amino-1-(4-(3-(5-(tert-butyl)isoxazol-3-yl)ureido)phenyl)-1H-pyrazolo[3,4-c]pyrimidin-3-yl)phenyl)-2-(dimethylamino) Acetamide

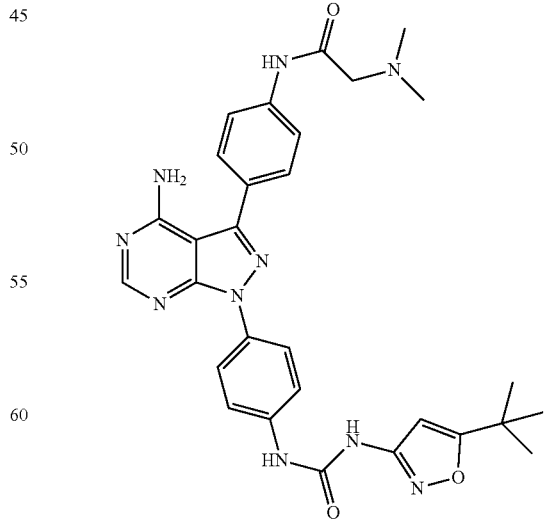

Synthesis of Compound 55 was accomplished by using procedures similar to that described in Example 1.

Exact Mass (calculated): 568.27; MS(ESI) m/z (M+1)⁺: 569.2754.

Example 56

Compound 56: 1-(4-(4-amino-3-(4-((2-(dimethylamino)ethyl)methylamino)phenyl)-1H-pyrazolo[3,4-d]pyrimidin-1-yl)phenyl)-3-(5-(tert-butyl)isoxazol-3-yl)urea

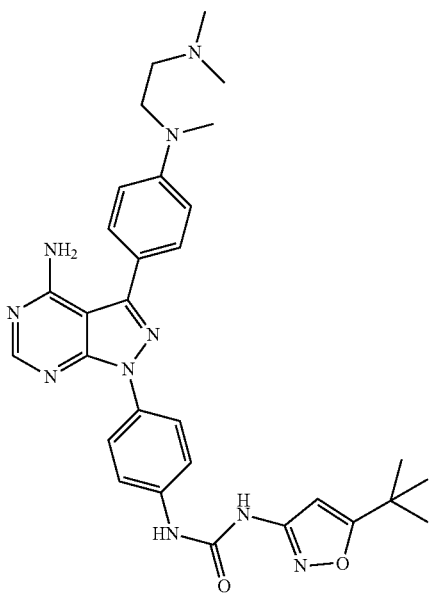 [SMILES: CN(C)CCN(C)c1ccc(-c2nn(-c3ccc(NC(=O)Nc4cc(C(C)(C)C)on4)cc3)c3ncnc(N)c23)cc1]

Synthesis of Compound 56 was accomplished by using procedures similar to that described in Example 1.

Exact Mass (calculated): 568.30; MS(ESI) m/z (M+1)⁺: 569.3062.

Example 57

Compound 57: 1-(4-(4-amino-3-(4-(4-(2-hydroxyethyl)piperazin-1-yl)phenyl)-1H-pyrazolo[3,4-d]pyrimidin-1-yl)phenyl)-3-(5-(tert-butyl)isoxazol-3-yl)urea

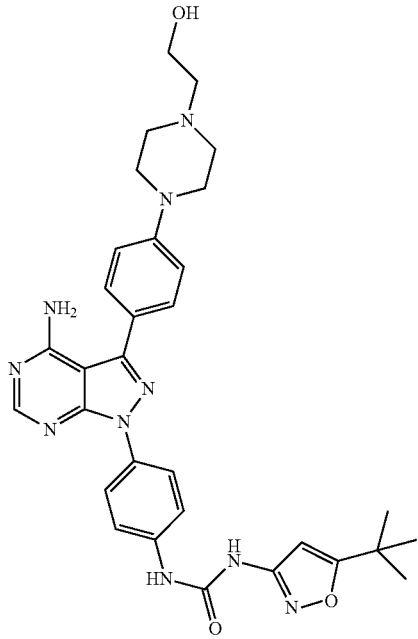

Synthesis of Compound 57 was accomplished by using procedures similar to that described in Example 1.

Exact Mass (calculated): 596.30; MS(ESI) m/z (M+1)⁺: 597.3032.

Example 58

Compound 58: 1-(4-(4-amino-3-(4-(4-(2-aminoethyl)piperazin-1-yl)phenyl)-1H-pyrazolo[3,4-d]pyrimidin-1-yl)phenyl)-3-(5-(tert-butyl)isoxazol-3-yl)urea

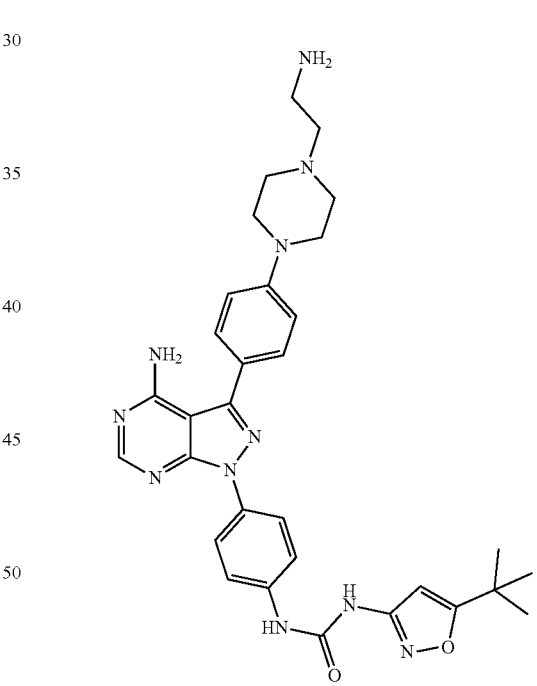

Synthesis of Compound 58 was accomplished by using procedures similar to that described in Example 1.

Exact Mass (calculated): 595.31; MS(ESI) m/z (M+1)⁺: 596.3148.

Example 59

Compound 59: 1-(4-(4-amino-3-(4-(1-(2-dydroxy-ethyl)piperidin-4-yl)phenyl)-1H-pyrazolo[3,4-d]pyrimidin-1-yl)phenyl)-3-(5-(tert-butyl)isoxazol-3-yl)urea

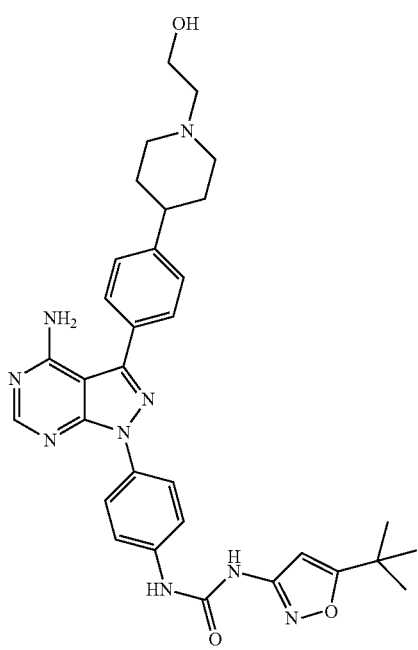 [SMILES: CC(C)(C)c1cc(NC(=O)Nc2ccc(-n3nc(-c4ccc(C5CCN(CCO)CC5)cc4)c4c(N)ncnc43)cc2)no1]

Synthesis of Compound 59 was accomplished by using procedures similar to that described in Example 1.
Exact Mass (calculated): 595.30; MS(ESI) m/z (M+1)$^+$: 596.3059.

Example 60

Compound 60: 1-(4-(4-amino-3-(4-(piperidin-4-yl)phenyl)-1H-pyrazolo[3,4-d]pyrimidin-1-yl)phenyl)-3-(5-(tert-butyl)isoxazol-3-yl)urea

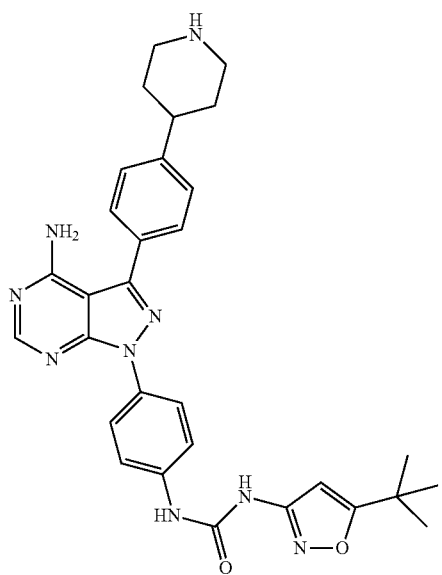 [SMILES: CC(C)(C)c1cc(NC(=O)Nc2ccc(-n3nc(-c4ccc(C5CCNCC5)cc4)c4c(N)ncnc43)cc2)no1]

Synthesis of Compound 60 was accomplished by using procedures similar to that described in Example 1.

Exact Mass (calculated): 551.28; MS(ESI) m/z (M+1)$^+$: 552.2830.

Example 61

Compound 61: 1-(4-(4-amino-3-(4-(1-methylpiperidin-4-yl)phenyl)-1H-pyrazolo[3,4-d]pyrimidin-1-yl)phenyl)-3-(5-(tert-butyl)isoxazol-3-yl)urea

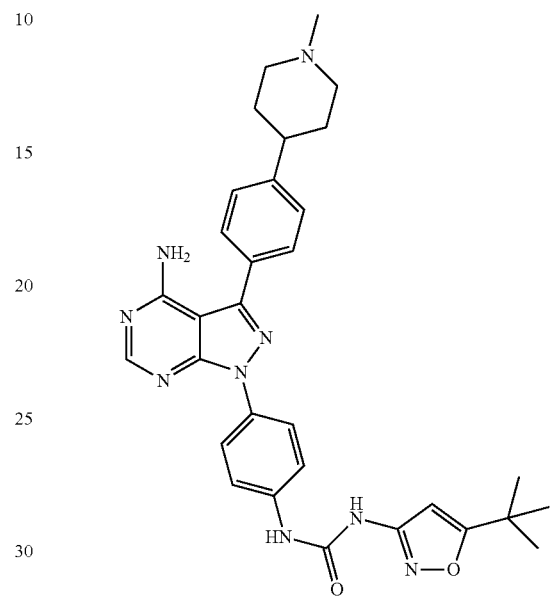

Synthesis of Compound 61 was accomplished by using procedures similar to that described in Example 1.
Exact Mass (calculated): 565.29; MS(ESI) m/z (M+1)$^+$: 566.2946.

Example 62

Compound 62: 1-(4-(4-amino-3-(4-(1-ethylpiperidin-4-yl)phenyl)-1H-pyrazolo[3,4-d]pyrimidin-1-yl)phenyl)-3-(5-(tert-butyl)isoxazol-3-yl)urea

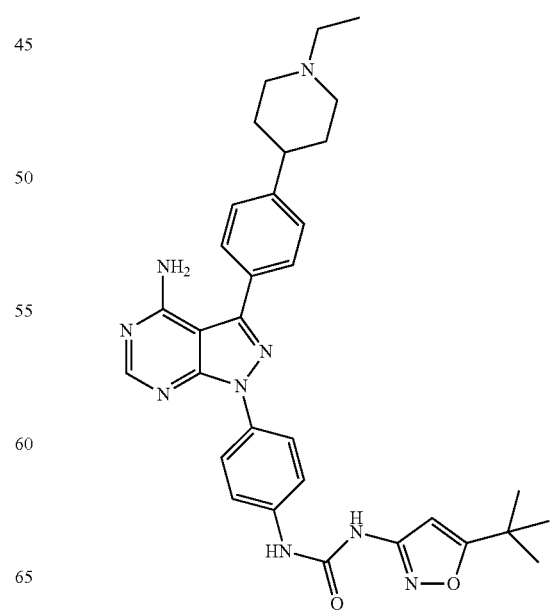

Synthesis of Compound 62 was accomplished by using procedures similar to that described in Example 1.

Exact Mass (calculated): 579.31; MS(ESI) m/z (M+1)$^+$: 580.3166.

Example 63

Compound 63: 1-(4-(4-amino-3-(4-(2-(dimethyl-amino)ethoxy)phenyl)-1H-pyrazolo[3,4-d]pyrimi-din-1-yl)phenyl)-3-(5-(tert-butyl)isoxazol-3-yl)urea

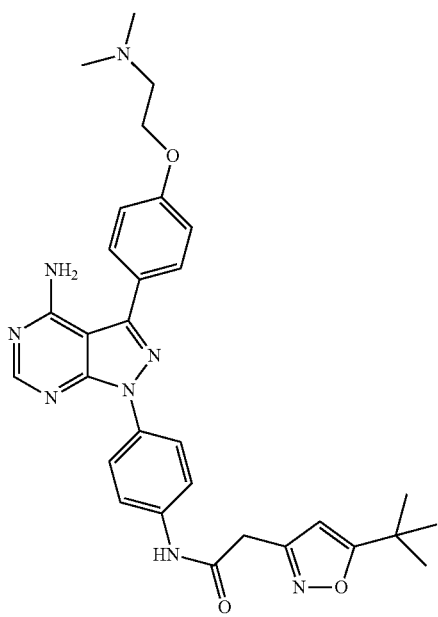 [SMILES: CN(C)CCOc1ccc(-c2nn(-c3ccc(NC(=O)Cc4cc(C(C)(C)C)on4)cc3)c3ncnc(N)c23)cc1]

Synthesis of Compound 63 was accomplished by using procedures similar to that described in Example 1.

Exact Mass (calculated): 555.27; MS(ESI) m/z (M+1)$^+$: 556.2786.

Example 64

Compound 64: 1-(4-(4-amino-3-(4-(2-(diethyl-amino)ethoxy)phenyl)-1H-pyrazolo[3,4-d]pyrimi-din-1-yl)phenyl)-3-(5-(tert-butyl)isoxazol-3-yl)urea

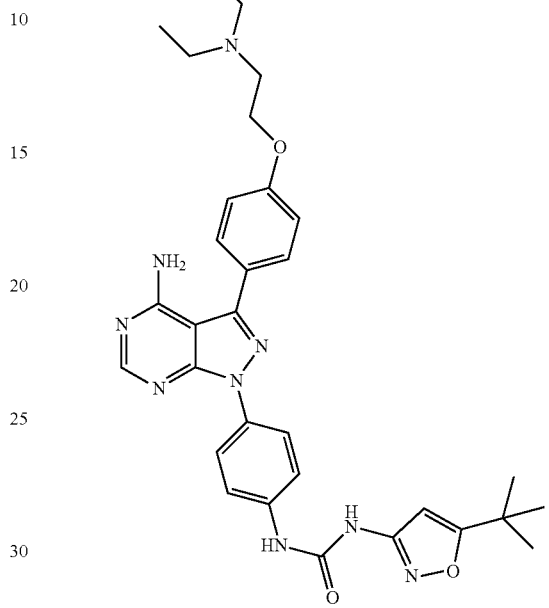

Synthesis of Compound 64 was accomplished by using procedures similar to that described in Example 1.

Exact Mass (calculated): 583.30; MS(ESI) m/z (M+1)$^+$: 584.3076.

Example 65

Compound 65: N-(4-(4-amino-1-(4-(3-(5-(tert-butyl)isoxazol-3-yl)ureido)phenyl)-1H-pyrazolo[3,4-c]pyrimidin-3-yl)phenyl)cyclopropane Sulfonamide

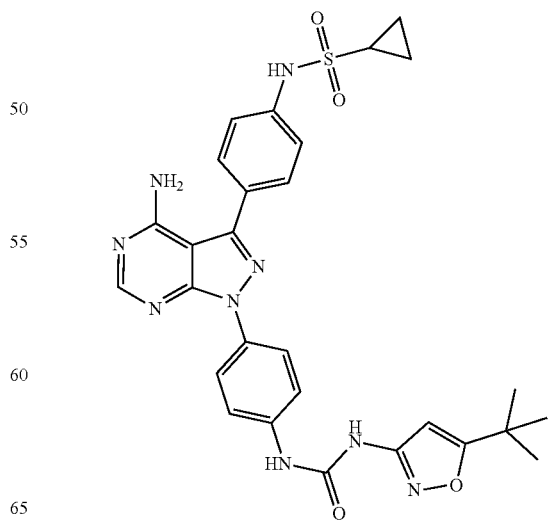

Synthesis of Compound 65 was accomplished by using procedures similar to that described in Example 1.

Exact Mass (calculated): 587.21; MS(ESI) m/z (M+1)$^+$: 588.2178.

Example 66

Compound 66: N-(4-(4-amino-1-(4-(3-(5-(tert-butyl) isoxazol-3-yl)ureido)phenyl)-1H-pyrazolo[3,4-c] pyrimidin-3-yl)phenyl)isopropyl Sulfonamide

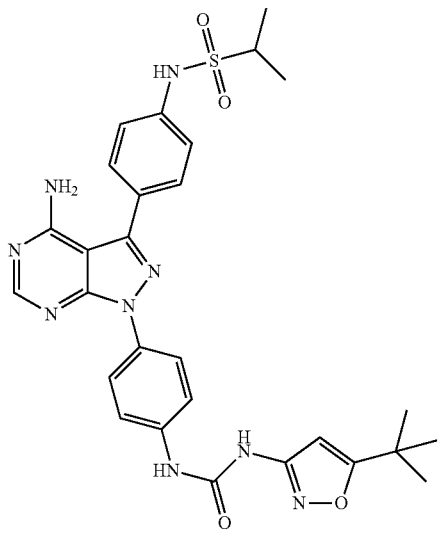 [SMILES: CC(C)S(=O)(=O)Nc1ccc(-c2nn(-c3ccc(NC(=O)Nc4cc(C(C)(C)C)on4)cc3)c3ncnc(N)c23)cc1]

Synthesis of Compound 66 was accomplished by using procedures similar to that described in Example 1.

Exact Mass (calculated): 589.22; MS(ESI) m/z (M+1)$^+$: 590.2238.

Example 67

Compound 67: 1-(4-(4-amino-3-(4-(isopropylsulfonyl)phenyl)-1H-pyrazolo[3,4-d]pyrimidin-1-yl)phenyl)-3-(5-(tert-butyl)isoxazol-3-yl)urea

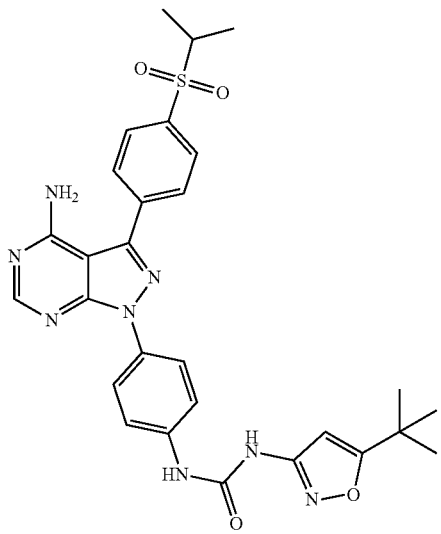 [SMILES: CC(C)S(=O)(=O)c1ccc(-c2nn(-c3ccc(NC(=O)Nc4cc(C(C)(C)C)on4)cc3)c3ncnc(N)c23)cc1]

Synthesis of Compound 67 was accomplished by using procedures similar to that described in Example 1.

Exact Mass (calculated): 574.21; MS(ESI) m/z (M+1)$^+$: 575.2193.

Example 68

Compound 68: (4-(4-amino-1-(4-(3-(5-(tert-butyl) isoxazol-3-yl)ureido)phenyl)-1H-pyrazolo[3,4-c] pyrimidin-3-yl)phenoxyl)-N,N,N-trimethylmethanaminium Iodide

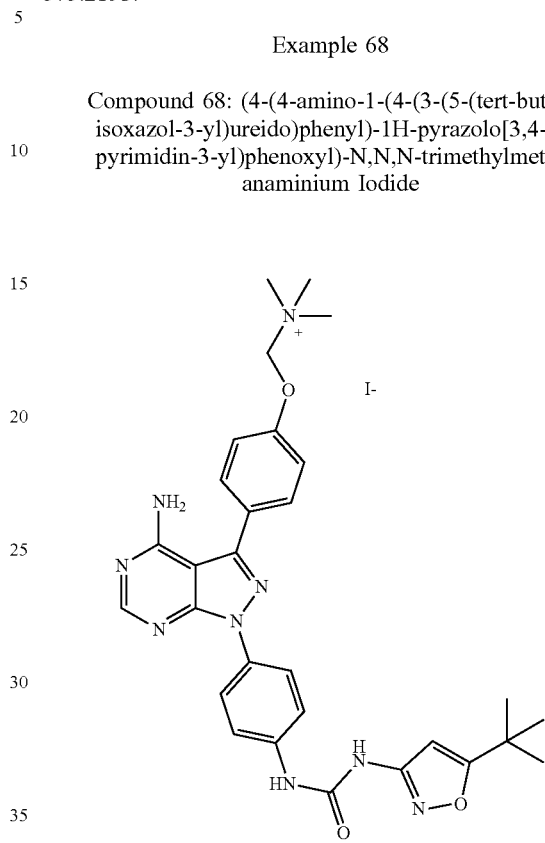

Synthesis of Compound 68 was accomplished by using procedures similar to that described in Example 1.

Exact Mass (calculated): 556.28; MS(ESI) m/z (M+1)$^+$: 557.2864.

Example 69: Effects on Proliferation of Cancer Cells

Compounds of the invention were evaluated for their inhibitory effects on proliferation of cancer cells as well as the selectivity thereof by testing their effects on growth of cancer cells (Table 2).

In this example the following cells were selected: human acute myeloid leukemia cells MV-4-11 (expressing FLT3 [ITD] mutant gene), human acute myeloid leukemia cells MOLM-13 (expressing FLT3[ITD] mutant gene and wild-type FLT3 gene), human acute myeloid leukemia cells MOLM-14 (expressing FLT3[ITD] mutant gene and wild-type FLT3 gene), human acute myeloid leukemia cells OCI-AML3 (expressing FLT3[A680V] mutant gene), human acute myeloid leukemia cells U937 (expressing wild-type FLT3 gene), and mouse pro-B cells BaF3, and the above cells were purchased from ATCC.

Mouse BaF3-FLT3[ITD] (stably expressing FLT3[ITD] mutant activated kinase), mouse tel-BaF3-FLT3-D835Y (stably expressing FLT3[D835Y]mutant activated kinase), mouse tel-BaF3-BMX (stably expressing BMX kinase), mouse tel-FLT3-BaF3 (stably expressing FLT3 kinase), mouse BaF3-FLT3-ITD-D835Y (stably expressing FLT3 [ITD+D835Y]mutant activated kinase), mouse BaF3-FLT3-

ITD-F691L (stably expressing FLT3[ITD+F691L]mutant activated kinase), mouse tel-cKIT-BaF3 (stably expressing cKIT kinase), mouse BaF3-tel-cKit-N882K (stably expressing cKIT-N882K mutant activated kinase), mouse BaF3-tel-cKit-D816V (stably expressing cKIT-D816V mutant activated kinase), mouse BaF3-tel-cKit-T670I (stably expressing cKIT-T670I mutant activated kinase), mouse TPR-MET-BaF3 (stably expressing MET kinase), mouse tel-BaF3-EGFR (stably expressing EGFR kinase), mouse BaF3-FL-EGFR-L858R (stably expressing EGFR[L858R] mutant activated kinase), mouse tel-BaF3-BLK (stably expressing BLK kinase), mouse tel-JAK1-BaF3 (stably expressing JAK1 kinase) and the like were also used (see Table 2 for details). The above cell lines were all constructed by our laboratory according to the following method: the kinase region sequences of human FLT3/ITD, FLT3 D835Y, BMX, FLT3, FLT3[ITD+D835Y], FLT3[ITD+F691L], cKIT, cKIT [N882K], cKIT [D816V], cKIT [T670I], MET, EGFR, EGFR [L858R], BLK, JAK1, FLT3[K663Q], FLT3 [D835V], FLT3[D835H], PDGFRa, PEGFRb, VEGFR2, JAK2, JAK3, ABL were amplified by PCR, and inserted into MSCV-Puro vectors with N-terminal TEL or TPR fragments (purchased from Clontech), respectively. The vectors were stably transfected into mouse BaF3 cells (purchased from ATCC) by means of retrovirus, and the growth factor IL-3 were removed, eventually obtaining cell lines that are transferred protein eventually obtaining cell lines that are transferred protein (FLT3/ITD, FLT3 D835Y, BMX, FLT3, FLT3 [ITD D835Y], FLT3[ITD+F691L], cKIT, cKIT [N882K], cKIT [D816V], cKIT [T670I], MET, EGFR, EGFR [L858R], BLK, JAK1, FLT3[K663Q], FLT3[D835V], FLT3 [D835H], PDGFRa, PEGFRb, VEGFR2, JAK2, JAK3, ABL)-dependent.

In the example the above cells were added with Compounds 1-30, 36-37 and 57 in different concentrations (0.000508 μM, 0.00152 μM, 0.00457 μM, 0.0137 μM, 0.0411 μM, 0.123 μM, 0.370 μM, 1.11 μM, 3.33 μM, 10 μM in DMSO) respectively and incubated for 72 hours. Then the number of viable cells was determined by quantification of ATP in living cells using Cell Titer-Glo® (Promega, the USA) Luminescent Cell Viability Assay kit and thereby $GI_{50}$ was calculated. Experimental results were shown in Table 2.

TABLE 2

Effects of different compounds on growth of various cancer cells ($GI_{50}$, μM)

| Cells | Compound 1 | Compound 2 | Compound 3 | Compound 4 | Compound 5 | Compound 6 |
|---|---|---|---|---|---|---|
| MV-4-11 | <0.3 nM | 0.069 | 0.26 | 2.8 | 0.082 | <0.0003 |
| MOLM-13 | <0.3 nM | | | | | <0.3 nM |
| MOLM-14 | <0.3 nM | 0.1 | 0.44 | 2.5 | 0.13 | <0.0003 |
| BaF3-TEL-FLT3 | <0.3 nM | 0.36 | 0.84 | 5.4 | 0.32 | <0.0003 |
| BaF3-FLT3 [ITD] | <0.3 nM | 0.056 | 0.24 | 1.1 | 0.1 | 0.002 |
| BaF3-TEL-FLT3 [D835Y] | 0.012 | 3.5 | 4.2 | >10 | 1.3 | 0.02 |
| BaF3-FLT3 [ITD + D835Y] | 0.002 | 3.5 | 4.2 | >10 | 1.3 | 0.055 |
| BaF3-FLT3 [ITD + F691L] | 0.002 | | | | | 0.013 |
| BaF3-TEL-FLT3 [K663Q] | 3.5 | 6.2 | 8 | >10 | 3.7 | 2.6 |
| BaF3-TEL-FLT3 [D835V] | 0.003 | 3.5 | 4.7 | >10 | 1.7 | 0.004 |
| BaF3-TEL-FLT3 [D835H] | <0.0003 | | | | | <0.0003 |
| BaF3-TEL-PDGFRa | <0.0003 | | | | | 0.003 |
| BaF3-TEL-PEGFRb | <0.0003 | | | | | 0.004 |
| BaF3 | | >10 | ~10 | >10 | 3.8 | 5.5 |
| U937 | 4.2 | 4.7 | 3.8 | >10 | 9.2 | 1.3 |
| OCI-AML3 | 6.3 | | | | | |
| BaF3-TEL-BMX | 1.1 | | | | | 1.9 |
| BaF3-TEL-cKIT | 0.001 | 3.9 | >10 | >10 | 3.5 | 0.14 |
| BaF3-TEL-cKit [N882K] | | 7.6 | 6.7 | >10 | 3.3 | 0.033 |
| BaF3-TEL-cKit [D816V] | 3.5 | 9.5 | 3.8 | >10 | 8.3 | 1.6 |
| BaF3-TEL-cKit [T670I] | | | | | | 0.007 |
| TPR-MET-BaF3 | 9.8 | | | | | |
| BaF3-TEL-EGFR | >10 | | | | | |
| BaF3-FL-EGFR [L858R] | | | | | | |
| BaF3-TEL-BLK | 3.6 | | | | | |

TABLE 2-continued

Effects of different compounds on growth of various cancer cells
($GI_{50}$, μM)

| | |
|---|---|
| BaF3-TEL-JAK1 | 3.8 |
| BaF3-TEL-JAK2 | |
| BaF3-TEL-JAK3 | 8.3 |
| BaF3-TEL-ABL | |
| BaF3-TEL-VEGFR2 | 0.002 |

| Cells | Compound 7 | Compound 8 | Compound 9 | Compound 10 | Compound 11 | Compound 12 |
|---|---|---|---|---|---|---|
| MV-4-11 | 0.12 | 0.038 | 0.26 | 0.063 | 0.002 | 0.003 |
| MOLM-13 | | | | | | |
| MOLM-14 | 0.1 | 0.081 | 0.28 | 0.081 | 0.002 | 0.003 |
| BaF3-TEL-FLT3 | 0.009 | 0.14 | 0.73 | 0.19 | 0.007 | 0.012 |
| BaF3-FLT3 [ITD] | 0.046 | 0.021 | 0.17 | 0.024 | 0.002 | 0.003 |
| BaF3-TEL-FLT3 [D835Y] | 0.24 | 3.7 | >10 | 4.4 | 1.5 | 1.6 |
| BaF3-FLT3 [ITD + D835Y] | 1.9 | 3.7 | >10 | 4.4 | 1.5 | 1.6 |
| BaF3-FLT3 [ITD + F691L] | 1.4 | | | | | |
| BaF3-TEL-FLT3 [K663Q] | 3.4 | 3.5 | >10 | >10 | >10 | 5.4 |
| BaF3-TEL-FLT3 [D835V] | 0.12 | 2.6 | >10 | 4.5 | 0.069 | 0.21 |
| BaF3-TEL-FLT3 [D835H] | 0.05 | | | | | |
| BaF3-TEL-PDGFRa | 0.002 | | | | | |
| BaF3-TEL-PEGFRb | 0.012 | | | | | |
| BaF3 | >10 | 6.2 | >10 | >10 | 6.5 | 3.0 |
| U937 | 3.3 | 4.1 | >10 | 8.5 | 4.2 | 2.4 |
| OCI-AML3 | | | | | | |
| BaF3-TEL-BMX | 1.8 | | | | | |
| BaF3-TEL-cKIT | 0.095 | 2.9 | >10 | 0.99 | 0.077 | 0.14 |
| BaF3-TEL-cKit [N882K] | 0.042 | 2.7 | >10 | 1.1 | 2.7 | 0.096 |
| BaF3-TEL-cKit [D816V] | 3.9 | 3.6 | >10 | 4.4 | 7.8 | 4 |
| BaF3-TEL-cKit [T670I] | 0.019 | | | | | |

| Cells | Compound 13 | Compound 14 | Compound 15 | Compound 16 | Compound 17 | Compound 18 |
|---|---|---|---|---|---|---|
| MV-4-11 | 0.042 | 0.001 | 0.001 | 0.001 | 0.56 | 0.001 |
| MOLM-13 | | | | | | |
| MOLM-14 | 0.082 | 0.001 | <0.0003 | 0.001 | 0.78 | 0.002 |
| BaF3-TEL-FLT3 | 0.23 | <0.0003 | <0.0003 | <0.0003 | 0.44 | 0.002 |
| BaF3-FLT3 [ITD] | 0.013 | 0.001 | <0.0003 | 0.002 | 0.87 | <0.0003 |
| BaF3-TEL-FLT3 [D835Y] | 9.7 | 0.035 | 0.007 | 0.041 | 8.5 | 0.055 |
| BaF3-FLT3 [ITD + D835Y] | 9.7 | 0.13 | 0.12 | 0.28 | 3.9 | 0.36 |
| BaF3-FLT3 [ITD + F691L] | | 0.077 | 0.023 | 0.082 | 4.6 | 0.11 |
| BaF3-TEL-FLT3 [K663Q] | 8 | 3.1 | 3.7 | 6.4 | 8.3 | >10 |
| BaF3-TEL-FLT3 [D835V] | 2.3 | 0.022 | 0.01 | 0.024 | 5.4 | 0.053 |
| BaF3-TEL-FLT3 [D835H] | | 0.004 | 0.005 | 0.006 | 3.0 | 0.008 |

TABLE 2-continued

Effects of different compounds on growth of various cancer cells
($GI_{50}$, μM)

| Cells | | | | | |
|---|---|---|---|---|---|
| BaF3-TEL-PDGFRa | | 0.002 | <0.0003 | 0.002 | 0.008 | 0.002 |
| BaF3-TEL-PEGFRb | | 0.004 | 0.002 | 0.004 | 0.31 | 0.008 |
| BaF3 | >10 | 6.4 | 7.2 | ~10 | 6.9 | >10 |
| U937 | 2.9 | 1.7 | 8.1 | 8.6 | 6.6 | >10 |
| OCI-AML3 | | | | | | |
| BaF3-TEL-BMX | | 1.2 | 3.3 | 3.8 | 3.8 | >10 |
| BaF3-TEL-cKIT | 1.2 | 0.05 | 0.004 | 0.061 | 3.2 | 0.33 |
| BaF3-TEL-cKit [N882K] | 1.5 | 0.036 | 0.009 | 0.04 | 1.8 | 0.041 |
| BaF3-TEL-cKit [D816V] | 5.3 | 1.7 | 1.5 | 2.3 | 8.2 | 7.0 |
| BaF3-TEL-cKit [T670I] | | 0.009 | 0.006 | 0.004 | 2.7 | 0.026 |

| Cells | Compound 19 | Compound 20 | Compound 21 | Compound 22 | Compound 24 |
|---|---|---|---|---|---|
| MV-4-11 | <0.0003 | <0.0003 | <0.0003 | <0.0003 | 0.002 |
| MOLM-13 | | | | | |
| MOLM-14 | 0.0009 | <0.0003 | <0.0003 | <0.0003 | 0.002 |
| BaF3-TEL-FLT3 | 0.001 | 0.002 | 0.001 | 0.001 | 0.001 |
| BaF3-FLT3 [ITD] | 0.0006 | 0.0009 | <0.0003 | <0.0003 | <0.0003 |
| BaF3-TEL-FLT3 [D835Y] | 0.57 | 0.24 | 0.009 | 0.02 | 0.12 |
| BaF3-FLT3 [ITD + D835Y] | 0.57 | 0.24 | 0.059 | 0.1 | 0.26 |
| BaF3-FLT3 [ITD + F691L] | | | 0.12 | 0.039 | 1.2 |
| BaF3-TEL-FLT3 [K663Q] | 1.8 | 1.6 | 3.6 | 3.8 | >10 |
| BaF3-TEL-FLT3 [D835V] | 0.023 | 0.008 | 0.004 | 0.017 | 0.095 |
| BaF3-TEL-FLT3 [D835H] | | | <0.0003 | 0.004 | <0.0003 |
| BaF3-TEL-PDGFRa | | | 0.002 | 0.002 | 0.006 |
| BaF3-TEL-PEGFRb | | | 0.01 | 0.012 | 0.012 |
| BaF3 | 3.3 | 2.5 | ~10 | 6.5 | >10 |
| U937 | 4.0 | 1.7 | 2.3 | 8.5 | >10 |
| OCI-AML3 | | | | | |
| BaF3-TEL-BMX | | | 5.3 | 2.0 | 7.0 |
| BaF3-TEL-cKIT | 0.04 | 0.04 | 0.031 | 0.04 | 0.12 |
| BaF3-TEL-cKit [N882K] | 0.018 | 0.009 | 0.010 | 0.015 | 0.016 |
| BaF3-TEL-cKit [D816V] | 2.9 | 1.9 | 1.8 | 2.2 | 6.8 |
| BaF3-TEL-cKit [T670I] | | | 0.004 | 0.013 | 0.024 |

| Cells | Compound 25 | Compound 26 | Compound 27 | Compound 29 | Compound 30 |
|---|---|---|---|---|---|
| MV-4-11 | 0.0005 | <0.0003 | 0.0006 | 0.0005 | 0.021 |
| MOLM-13 | | | | | 0.032 |
| MOLM-14 | 0.0004 | 0.001 | 0.001 | 0.0004 | 0.032 |
| BaF3-TEL-FLT3 | 0.003 | 0.001 | 0.002 | 0.002 | |
| BaF3-FLT3 [ITD] | 0.002 | 0.0007 | 0.001 | 0.0007 | 0.001 |
| BaF3-TEL-FLT3 [D835Y] | 0.25 | 0.61 | 0.6 | 0.44 | 0.014 |
| BaF3-FLT3 [ITD + D835Y] | 0.25 | 0.61 | 0.6 | 0.44 | 3.7 |
| BaF3-FLT3 [ITD + F691L] | | | | | |
| BaF3-TEL-FLT3 [K663Q] | ~10 | >10 | >10 | 6.5 | |
| BaF3-TEL-FLT3 [D835V] | 0.009 | 0.02 | 0.022 | 0.022 | 0.033 |
| BaF3-TEL-FLT3 [D835H] | | | | | 0.19 |
| BaF3-TEL-PDGFRa | | | | | |
| BaF3-TEL-PEGFRb | | | | | 0.29 |
| BaF3 | >10 | >10 | >10 | >10 | |
| U937 | 9.9 | >10 | >10 | 3.7 | |
| OCI-AML3 | | | | | 1.9 |
| BaF3-TEL-BMX | | | | | 1.1 |
| BaF3-TEL-cKIT | 0.041 | 0.038 | 0.12 | 0.041 | |
| BaF3-TEL-cKit [N882K] | 0.018 | 0.029 | 0.051 | 0.053 | |
| BaF3-TEL-cKit [D816V] | 3.6 | 7.6 | >10 | 3.2 | >10 |

| Cells | Compound 23 | Compound 28 | Compound 36 | Compound 37 | Compound 57 |
|---|---|---|---|---|---|
| MOLM-14 | <0.0003 | 0.002 | <0.0003 | 0.0009 | 0.001 |
| MV-4-11 | <0.0003 | 0.001 | <0.0003 | <0.0003 | <0.0003 |

TABLE 2-continued

Effects of different compounds on growth of various cancer cells (GI$_{50}$, μM)

| | | | | | |
|---|---|---|---|---|---|
| BaF3-FLT3 [ITD] | | 0.002 | <0.0003 | <0.0003 | <0.0003 |
| BaF3-TEL-FLT3 [D835Y] | 0.001 | 0.003 | 0.003 | 0.002 | 0.005 |
| BaF3-TEL-FLT3 [K663Q] | 5.4 | >10 | 1.4 | 0.93 | 1.2 |
| BaF3-TEL-FLT3 | <0.0003 | 0.004 | 0.001 | <0.0003 | |
| BaF3 | 5.9 | 6.9 | 2.8 | 1.9 | 2.5 |
| BaF3-TEL-cKIT | 0.012 | 0.041 | 0.027 | 0.015 | 0.012 |
| U937 | 4.1 | >10 | 2.8 | 1.8 | |

In addition, in order to mimic the situation in which the subject developed drug resistance, three cell lines (MOLM-13, MOLM-14 and MV-4-11) were used to carry out in vitro experiments with addition of different concentrations of FLT3 ligand (FL) so as to test Compound 1 of this invention.

In experiments with addition of FLT3 ligand (FL) (as shown in Table 3 below), it can be obviously seen that after addition of 1 ng/ml, 5 ng/ml, 10 ng/ml of FLT3 ligand (FL) into human acute myeloid leukemia cells MOLM-13 and MOLM-14 cells having FLT3-ITD mutant gene and wild-type FLT3 gene, with the addition amount of FLT3 ligand (FL) increasing in MOLM-13 and MOLM-14 cells, there is no significant change in IC50 of Compound 1. As to human acute myeloid leukemia cells MV-4-11 that carry only FLT3 mutant gene, the IC50 of Compound 1 obtained in a case with addition of 10 ng/ml FLT3 ligand (FL) and the IC50 obtained in a case without addition of FLT3 ligand (FL) was similar, indicating that Compound 1 has little influence on proliferation of human acute myeloid leukemia cells under over-expression of the ligand FL, which causes drug resistance.

The results in Table 3 indicate that the effect of Compound 1 is substantially not affected by the presence of FL ligand. Based on such results, it can be speculated that even when acute myeloid leukemia cells that carry FLT3 mutant gene developed drug resistance due to increase in FL ligand secretion, Compound 1 can also exert a significant inhibitory effect. It suggests that Compound 1 can be applied to the treatment of FLT3 mutant gene-carrying acute myelocytic leukemia and overcoming high expression of FL ligand-mediated drug resistance thereof.

TABLE 3

| | IC50 (nM) of Compound 1 |
|---|---|
| MOLM-14 | 0.36 |
| MOLM-14 + FL (1 ng/mL) | 0.87 |
| MOLM-14 + FL (5 ng/mL) | 1.0 |
| MOLM-14 + FL (10 ng/mL) | 1.0 |
| MOLM-13 | 0.27 |
| MOLM-13 + FL (1 ng/mL) | 1.1 |
| MOLM-13 + FL (5 ng/mL) | 1.3 |
| MOLM-13 + FL (10 ng/mL) | 1.1 |
| MV-4-11 | 0.4 |
| MV-4-11 + FL (10 ng/mL) | 0.38 |

Example 70: Effects of Compound 1 on Upstream and Downstream Signaling Pathways of FLT3 in Cells In human acute myeloid leukemia cells MV-4-11 (expressing FLT3 [ITD] mutant gene), human acute myeloid leukemia cells MOLM-13 (expressing FLT3[ITD] mutant gene and wild-type FLT3 gene) and human acute myeloid leukemia cells MOLM-14 (expressing FLT3[ITD] mutant gene and wild-type FLT3 gene), Compound 1 and a FLT3 kinase inhibitor, AC220, which was used as the control (purchased from Hao Yuan Chemexpress, Shanghai), were evaluated for their effects in cells on phosphorylation of FLT3 and FLT3/ITD protein kinase and phosphorylation of the closely-related STAT5 protein which is downstream of FLT3 signaling pathways, as well as their effects on phosphorylation of other related protein kinases such as ERK and AKT, by assaying a number of cellular biochemical and functional endpoints. In addition, the effects of Compound 1 and AC220 on C-Myc degradation and phosphorylation of the transcription factor NF-κB subunit p65 was also examined, using glyceraldehyde-3-phosphate dehydrogenase (GAPDH) as the internal standard protein.

Compound 1 in different concentrations (0 μM, 0.001 μM, 0.003 μM, 0.01 μM, 0.03 μM, 0.1 μM, 0.3 μM in DMSO) and 0.1 μM (in DMSO) of AC220, the FLT3 kinase inhibitor, was used to treat acute myeloid leukemia cells MV-4-11, MOLM-13 and MOLM-14 (carrying FLT3 and/or FLT3/ITD gene) for 4 hours, respectively, and then the samples were collected. The compounds as tested were shown to influence the phosphorylation of proteins such as STAT5, ERK, NF-κB p65, AKT as well as c-Myc degradation in cells, as shown in FIG. 1.

The experimental results shown in FIG. 1 reflected that, Compound 1 strongly inhibited phosphorylation of the protein kinase FLT3 in acute myeloid leukemia MV-4-11, MOLM-13 and MOLM-14 cell lines. In addition, Compound 1 also exhibited significant inhibition on phosphorylation of STAT5 which is a protein downstream of FLT3/ITD, and had significant effects on the degradation of C-Myc which is a protein closely related to FLT3 protein kinase. As a control, the other FLT3 kinase inhibitor, AC220, also inhibited phosphorylation of the protein kinase FLT3 and STAT5 which is closely related to FLT3/ITD as well as the degradation of c-Myc in acute myeloid leukemia MV-4-11, MOLM-13 and MOLM-14 cell lines, the inhibitory effects being comparable to that of Compound 1 at 0.001 μM.

Example 70 reflected that Compound 1 was able to strongly inhibit the phosphorylation of the protein kinase FLT3, influence the phosphorylation of STAT5 which is downstream of FLT3 signaling pathways in cells. Based on such results, it can be inferred that Compound 1 can inhibit the protein kinase FLT3 as well as the relevant proteins, and further inhibit the proliferation of acute myeloid leukemia cells that carry FLT3 and/or FLT3/ITD genes.

Example 71: Effects of Compound 1 on Cell Apoptosis in Cells

In acute myeloid leukemia MOLM-13, MOLM-14, MV-4-11 cell lines, the effects of Compound 1 and AC220 as a control on protein cleavage of the DNA repairase poly(ADP-ribose) polymerase (PARP) and Caspase (cysteinyl aspartate-specific proteinase) 3 that were closely related to cell apoptosis were examined in cells in order to confirm whether the death of the cells after the administration was caused by apoptosis or necrosis.

MOLM-13, MOLM-14, MV-4-11 cell lines were treated with different concentrations of (0 µM, 0.003 µM, 0.01 µM, 0.03 µM, 0.1 µM in DMSO) Compound 1, 0.1 µM (in DMSO) of the FLT3 kinase inhibitor AC220, and the cells were collected after 12 hours, 24 hours and 48 hours. Western Blot was used to detect the effects of different concentrations of compounds on protein cleavage of the DNA repairase poly(ADP-ribose) polymerase (PARP) and Caspase (cysteinyl aspartate-specific proteinase) 3, wherein glyceraldehyde-3-phosphate dehydrogenase (GAPDH) was used as the internal standard protein.

Figure 2:
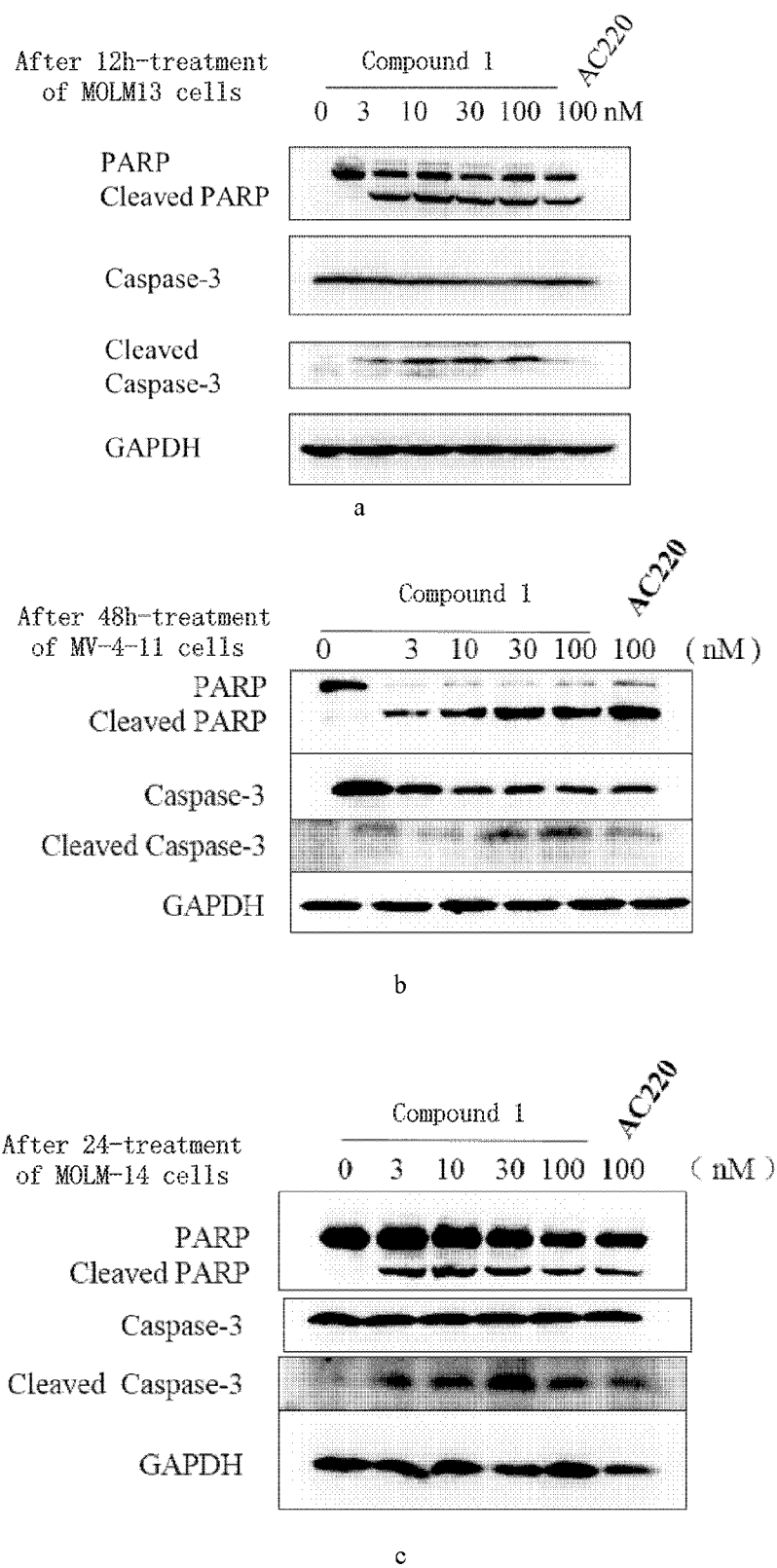

Experimental results were shown in FIG. 2: for acute myeloid leukemia cell lines MOLM-13, when Compound 1 was used at 0.003 µM, significant cleavage of the DNA repairase poly(ADP-ribose) polymerase (PARP) as well as significant cleavage of Caspase (cysteinyl aspartate-specific proteinase) 3 was observed after treatment of 12 hours. A similar result was observed for MOLM-14 cell lines 48 hours after administering Compound 1. A similar result was observed for MV-4-11 cell lines 24 hours after administering Compound 1, and cleavage of the DNA repairase poly(ADP-ribose) polymerase (PARP) was even more significant.

The above results reflected that Compound 1 was able to cause apoptosis of acute myeloid leukemia cells that carry FLT3 gene and/or FLT3/ITD mutant gene.

Example 72: Effects of Compound 1 on Cell Cycles in Cells

In acute myeloid leukemia MOLM-13, MOLM-14 and MV-4-11 cell lines, the effects of Compound 1 on cell cycle distribution of these cell lines were examined in order to study the growth cycle during which the cells were blocked by administration. Different concentrations of Compound 1 (0 µM, 0.01 µM, 0.03 µM, 0.1 µM in DMSO) and 0.1 µM of the FLT3 kinase inhibitor AC220 were used to act on MOLM-13, MOLM-14, and MV-4-11 cells, the cells were collected after 12 or 24 hours, washed twice with 1×PBS buffer, fixed with 75% ethanol at −20° C. for 24 hours, and washed again with 1×PBS buffer twice. 0.5 mL 1×PBS buffer and 0.5 mL of PI dyeing liquor (purchased from BD Bioscience, USA) were added to the cells, and the cells were placed in the dark at 37° C. for dyeing 15 minutes and the cell cycle distribution was detected by flow cytometry (BD FACS Calibur) (see FIG. 3).

Figure 3:
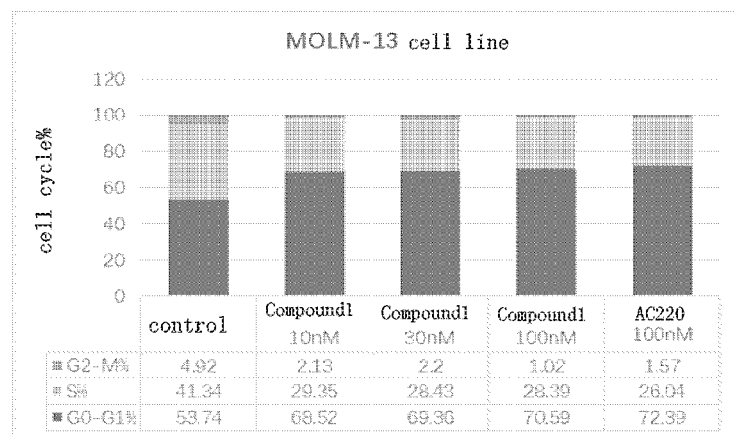
FIGS. 3a, 3b and 3c illustrate the effects of Compound 1 on the cell cycle of cell lines MOLM-13, MOLM-14 and MV-4-11, respectively.
Figure 3:
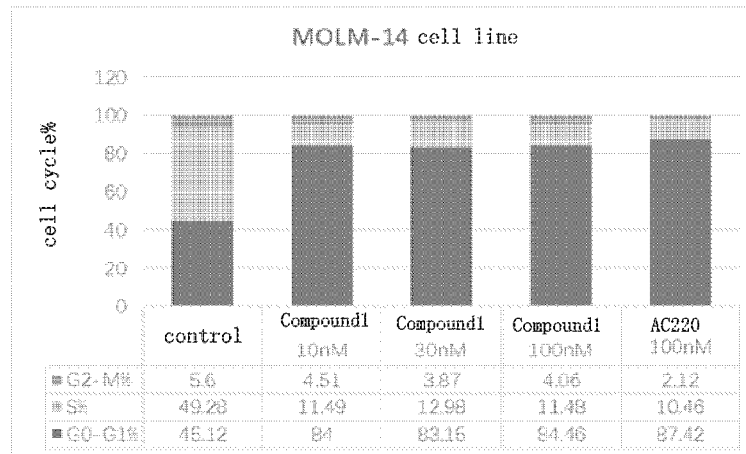
Figure 3:
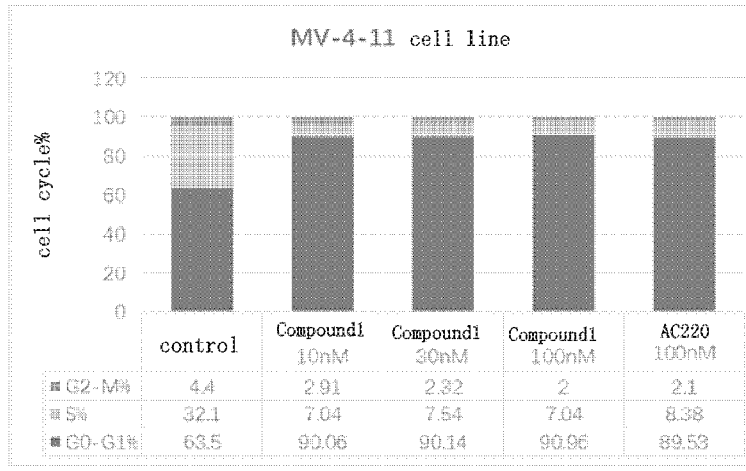

Experimental results were shown in FIG. 3: in acute myeloid leukemia MOLM-13, MOLM-14 and MV-4-11 cell lines that carry FLT3/ITD mutant gene, Compound 1 arrested the cell cycle at phase G0-G1, which was similar to the effects of AC220.

Example 72 proved that Compound 1 was able to arrest the cell cycle of acute myeloid leukemia MOLM-13, MOLM-14 and MV-4-11 cell lines that carry FLT3/ITD mutant gene at phase G0-G1, and thus showed a significant influence on cell cycle distribution (FIG. 3).

Example 73: Treating Acute Myeloid Leukemia with Compound 1

In order to detect the inhibitory effect of Compound 1 on tumors in vivo, a nude mouse model harboring subcutaneous tumor was introduced. 25 mice (5-week-old) (Balb/c-nu female mice, purchased from Shanghai Snake Experimental Animal Co., Ltd.) were inoculated subcutaneously with MOLM-14 cells in $1 \times 10^7$ cells/mouse, the changes in body weight and tumor volume were recorded daily (tumor volume=tumor length×tumor $width^2/2$). 10 days later, the mice, of which tumor volumes reached 200-400 $mm^3$, were randomly divided into four groups with 6 or 7 mice in each group, and were treated as follows: the first group was administered daily by oral gavage with vehicle, i.e., methylcellulose-based aqueous suspension (purchased from Sinopharm Group Chemical Reagent Co., Ltd.); the second group was administered daily by oral gavage with 3.75 mg/kg of Compound 1 in a methylcellulose-based aqueous suspension formulation; the third group was administered daily by oral gavage with 7.5 mg/kg of Compound 1 in a methylcellulose-based aqueous suspension formulation; and the fourth group was administered daily by oral gavage with 15 mg/kg of Compound 1 in a methylcellulose-based aqueous suspension formulation. The first day of administration was recorded as day 0, followed by continuous administration for 28 days (FIG. 4).

Figure 4:
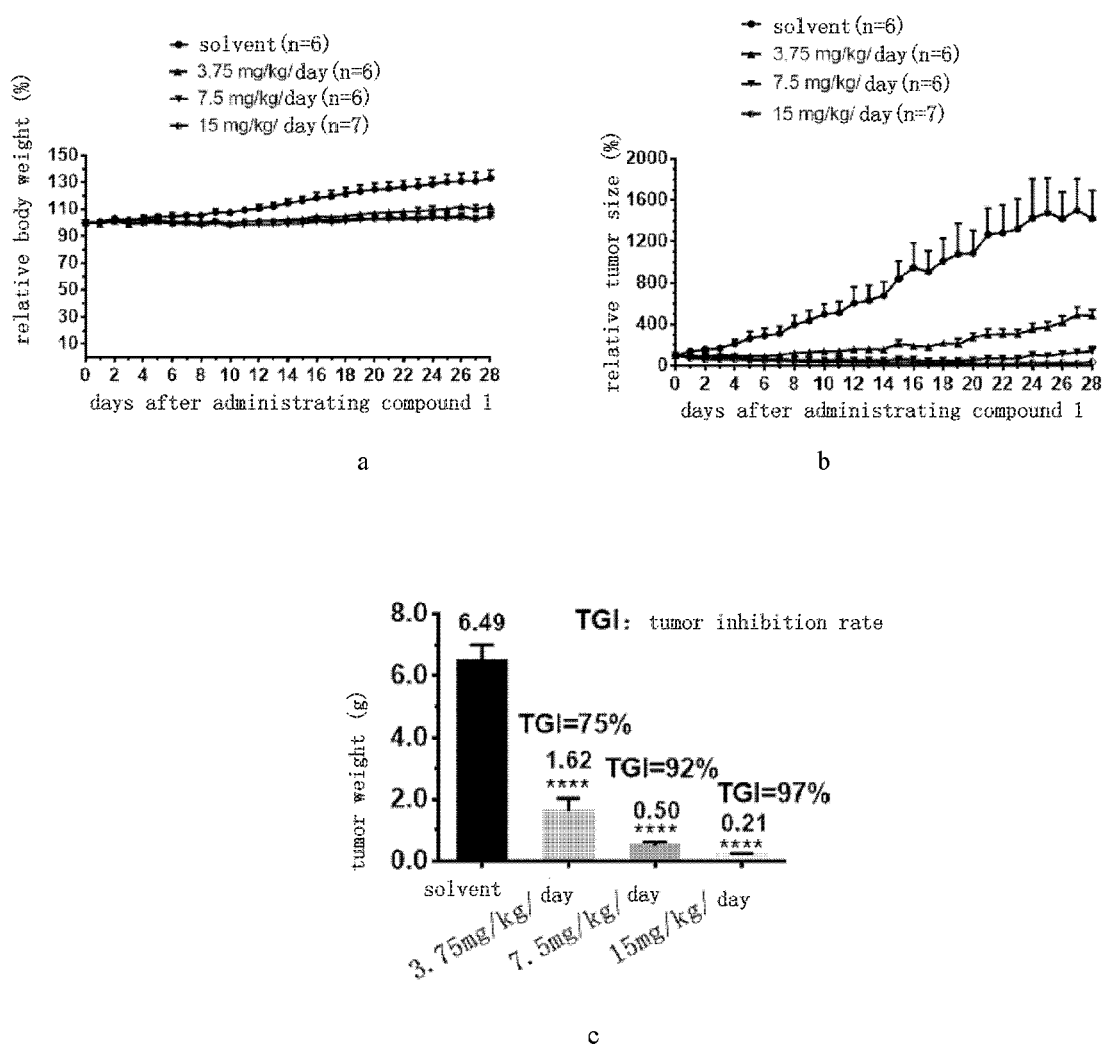

The experimental results were shown in FIG. 4. When the dosage of Compound 1 was 3.75 mg/kg, tumor growth in mice was significantly inhibited after treatment for 28 days, and there is no significant decrease in mice body weight, the tumor inhibition rate being as high as 75%. When the dosage of Compound 1 was 7.5 mg/kg, tumor growth in mice was substantially inhibited after treatment for 28 days and the body weight did not decrease, the tumor inhibition rate being as high as 92%. When the dosage of Compound 1 was 15 mg/kg, tumors in mice were completely suppressed after administration and the body weight did not decrease, the tumor inhibition rate being as high as 97%. The data obtained from the tumor-transplanted mouse model in this example demonstrated that Compound 1 could strongly inhibiting tumor growth in acute myeloid leukemia (AML) in mice.

INDUSTRIAL APPLICABILITY

The present invention provides a novel inhibitor of FLT3 kinase, which may be useful in reducing or inhibiting the activity of wild-type FLT3 kinase and/or mutant FLT3 kinase in a cell or a subject, and/or for preventing or treating FLT3-related conditions in a subject. Therefore, it can be prepared into corresponding medicaments and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A compound of Formula (I), or a pharmaceutically acceptable salt solvate, enantiomer, or diastereomer thereof, having the following structure:

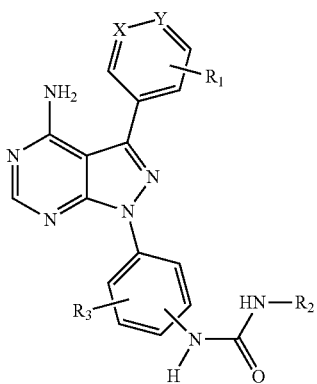

Formula (I)

wherein at least one of X and Y is CH, and the other is selected from the group consisting of CH and N;

$R_1$ is selected from the group consisting of hydrogen, halogen, $C_{1-8}$ alkyl, $C_{1-8}$ haloalkyl, $C_{1-8}$ alkoxy, $C_{1-8}$ alkylamino, $C_{1-8}$ haloalkoxy, $C_{1-8}$ aminoalkyl, $C_{1-8}$ aminoalkoxy, $C_{1-8}$ alkylamino $C_{1-8}$ alkoxy, quaternary ammonium $C_{1-8}$ alkoxy, $C_{1-8}$ alkanoyl $C_{1-8}$ alkyl, arylcarbonyl $C_{1-8}$ alkyl, $C_{1-8}$ alkanoyl $C_{1-8}$ alkoxy, arylcarbonyl $C_{1-8}$ alkoxy, aminosulfonyl, $C_{1-8}$ alkylaminosulfonyl, $C_{3-6}$ heterocycloalkyl, aminoacyl, $C_{1-8}$ alkylaminocarbonyl, $C_{3-6}$ heterocycloalkylcarbonyl, $C_{3-6}$ cycloalkyl, $C_{1-8}$ alkyl($C_{3-6}$ heterocycloalkyl), $C_{1-8}$ alkoxy($C_{3-6}$ heterocycloalkyl), $C_{3-6}$ heterocycloalkylcarbonyl $C_{1-8}$ alkyl, aryloxy, $C_{1-8}$ alkylsulfonyl, $C_{1-8}$ alkylsulfonylamino, $C_{3-6}$ cycloalkylsulfonylamino, $C_{3-6}$ heterocycloalkylaminocarbonyl, acylamino($C_{1-8}$ alkylamino $C_{1-8}$ alkyl), and $C_{1-8}$ alkylamino($C_{1-8}$ alkylamino), wherein aryl and heterocycloalkyl are optionally substituted with 1-3 independent $R_4$;

$R_2$ is selected from the group consisting of $C_{1-8}$ alkyl, $C_{1-8}$ haloalkyl, $C_{1-8}$ alkylamino $C_{1-8}$ alkyl, aryl and heteroaryl, wherein aryl and heteroaryl are optionally substituted with 1-3 independent $R_4$;

$R_3$ is selected from the group consisting of hydrogen and $C_{1-3}$ alkyl;

$R_4$ is independently selected from the group consisting of halogen, $C_{1-8}$ alkyl, $C_{1-8}$ alkoxy, $C_{1-8}$ haloalkyl, $C_{1-8}$ hydroxylalkyl, $C_{1-8}$ aminoalkyl, $C_{1-8}$ alkanoyl, $C_{1-8}$ alkylsulfonyl, and aminoacyl.

2. The compound or a pharmaceutically acceptable salt, solvate, enantiomer, or diastereomer thereof according to claim 1, wherein both X and Y are CH.

3. The compound or a pharmaceutically acceptable salt, solvate, enantiomer, or diastereomer thereof according to claim 1, wherein $R_1$ is a substituent on X or Y.

4. The compound or a pharmaceutically acceptable salt, solvate, enantiomer, or diastereomer thereof according to claim 1, wherein the compound is represented by Formula (II):

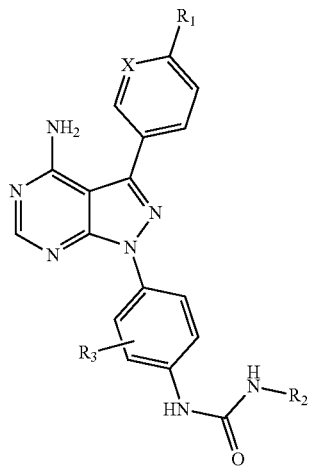

Formula (II)

wherein substituents X, $R_1$, $R_2$, $R_3$ and $R_4$ are defined as in claim 1.

5. The compound or a pharmaceutically acceptable salt, solvate, enantiomer, or diastereomer according to claim 1, wherein $R_1$ is selected from the group consisting of hydrogen, $C_{1-8}$ alkylamino, $C_{1-8}$ alkylamino $C_{1-8}$ alkoxy, quaternary ammonium $C_{1-8}$ alkoxy, $C_{1-8}$ alkylaminosulfonyl, $C_{3-6}$ heterocycloalkyl optionally substituted with $R_4$, aminoacyl, $C_{1-8}$ alkylaminocarbonyl, $C_{3-6}$ heterocycloalkylcarbonyl optionally substituted with $R_4$, $C_{1-8}$ alkyl($C_{3-6}$ heterocycloalkyl) optionally substituted with $R_4$, $C_{1-8}$ alkoxy($C_{3-6}$ heterocycloalkyl) optionally substituted with $R_4$, $C_{3-6}$ heterocycloalkylcarbonyl $C_{1-8}$ alkyl optionally substituted with $R_4$, phenoxyl optionally substituted with $R_4$, $C_{1-8}$ alkylsulfonyl, $C_{1-8}$ alkylsulfonylamino, $C_{3-6}$ cycloalkylsulfonylamino, $C_{3-6}$ heterocycloalkylaminocarbonyl optionally substituted with $R_4$, acylamino($C_{1-8}$ alkylamino $C_{1-8}$ alkyl), and $C_{1-8}$ alkylamino($C_{1-8}$ alkylamino).

6. The compound or a pharmaceutically acceptable salt, solvate, enantiomer, or diastereomer thereof according to claim 1, wherein $R_2$ is selected from the group consisting of $C_{1-8}$ alkyl, $C_{1-8}$ alkylamino $C_{1-8}$ alkyl, phenyl optionally substituted with $R_4$, and heteroaryl optionally substituted with $R_4$.

7. The compound or a pharmaceutically acceptable salt, solvate, enantiomer, or diastereomer thereof according to claim 1, wherein $R_2$ is 5-(tert-butyl)isoxazol-3-yl.

8. The compound or a pharmaceutically acceptable salt, solvate, enantiomer, or diastereomer thereof according to claim 1, wherein $R_3$ is hydrogen.

9. The compound or a pharmaceutically acceptable salt, solvate, enantiomer, or diastereomer thereof according t claim 1, wherein the compound is selected from the group consisting of:
Compound 1
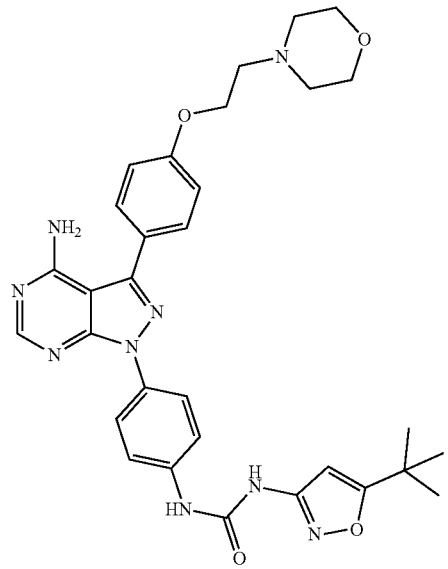
Compound 2
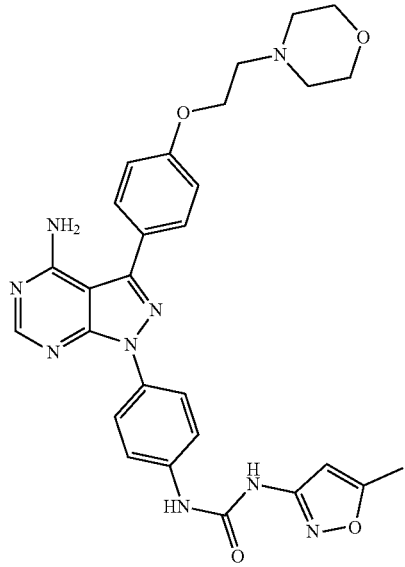
Compound 3
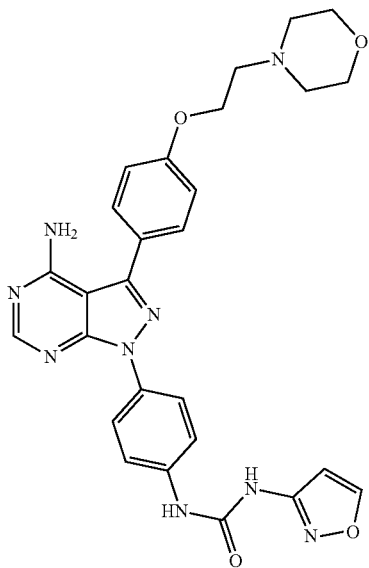
-continued
Compound 4
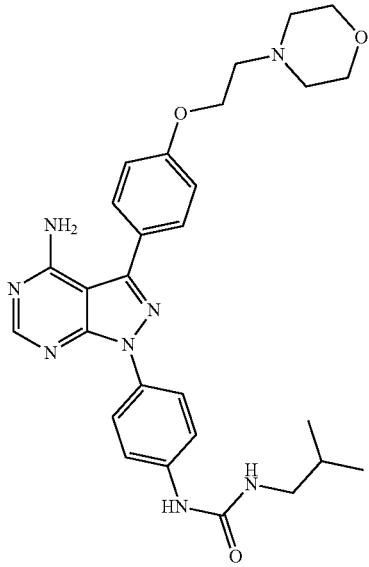

Compound 5
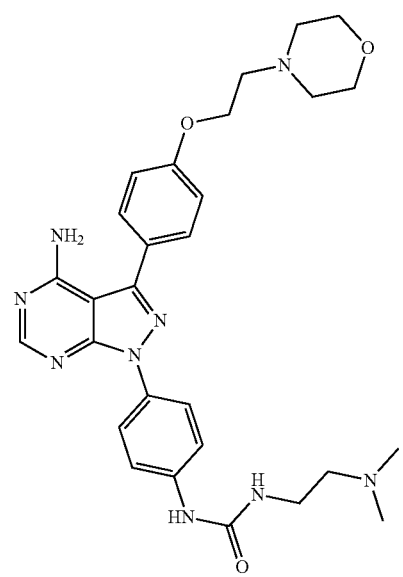
Compound 6
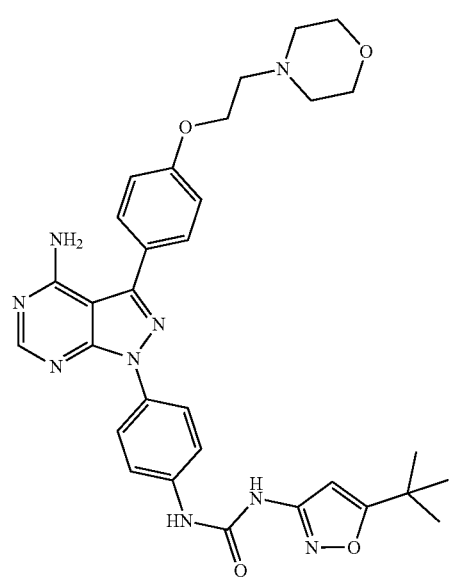
Compound 7
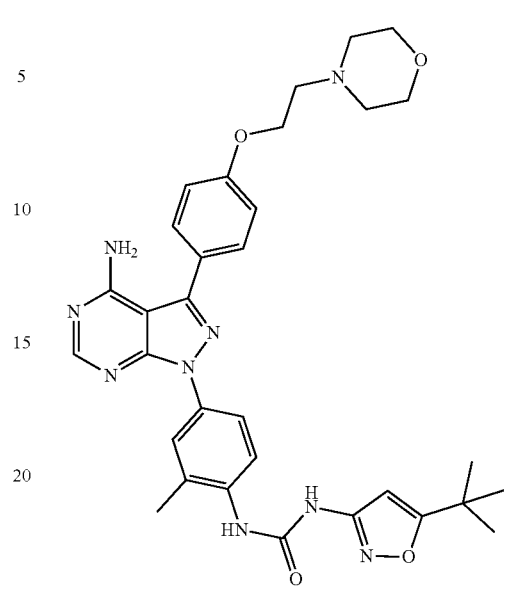
Compound 8
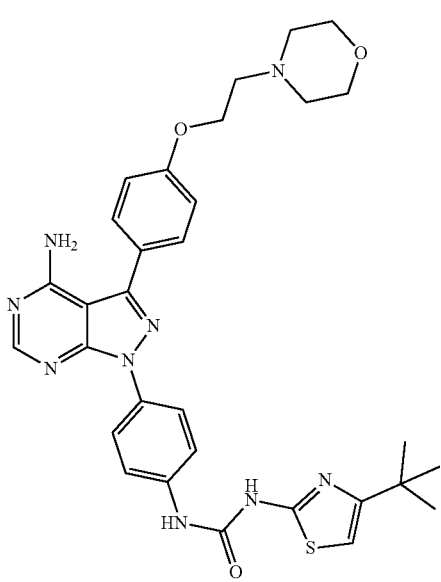

Compound 9
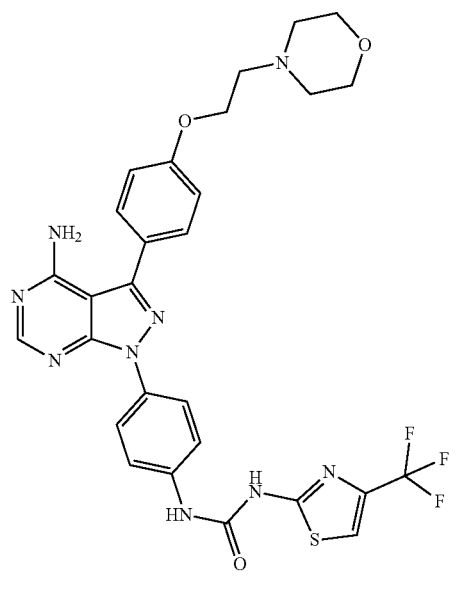
Compound 10
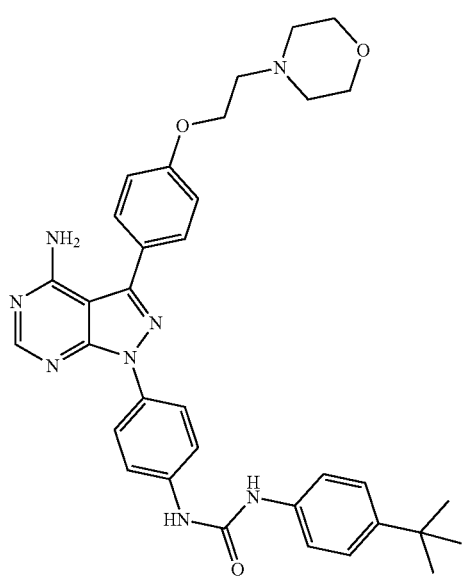
Compound 11
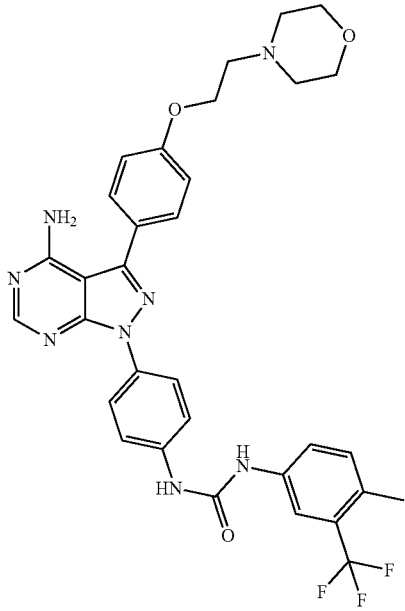
Compound 12
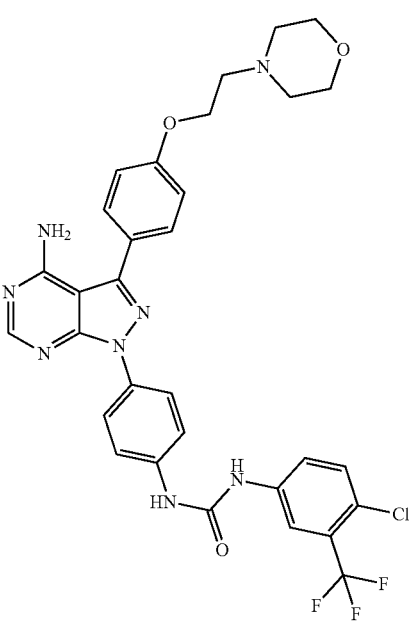

Compound 13
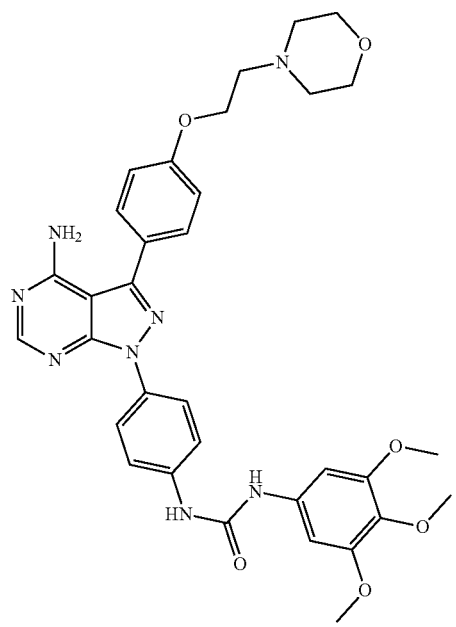
Compound 14
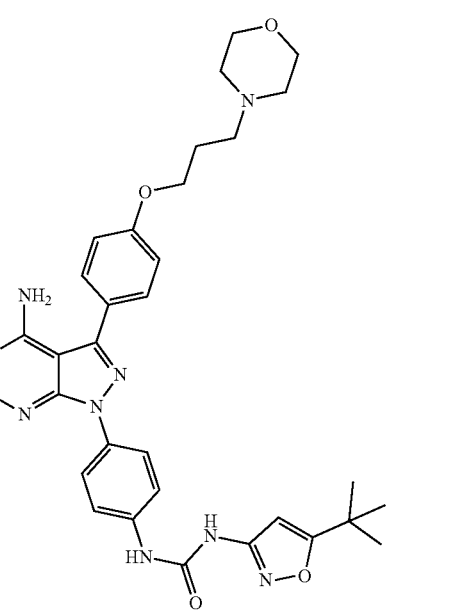
Compound 15
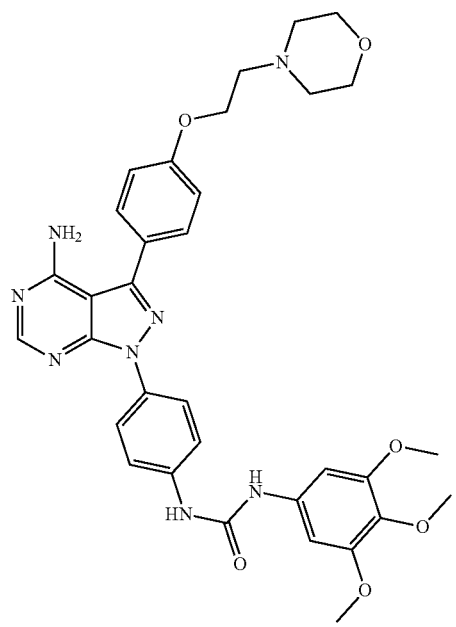
Compound 16
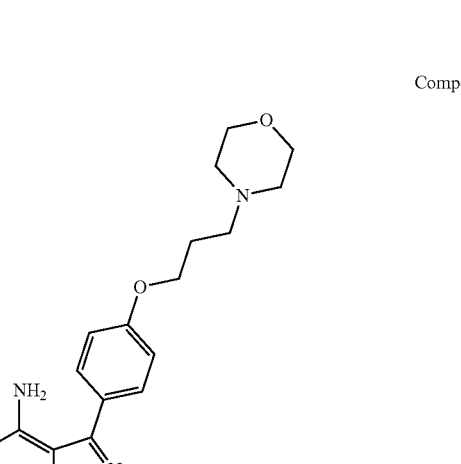
Compound 17
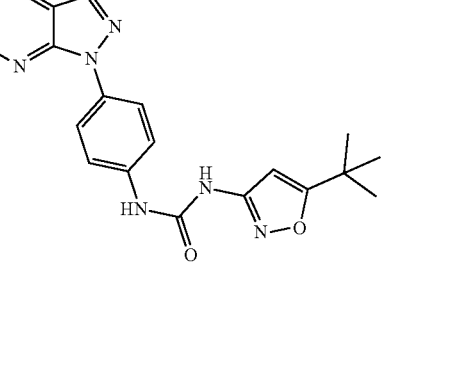

Compound 18
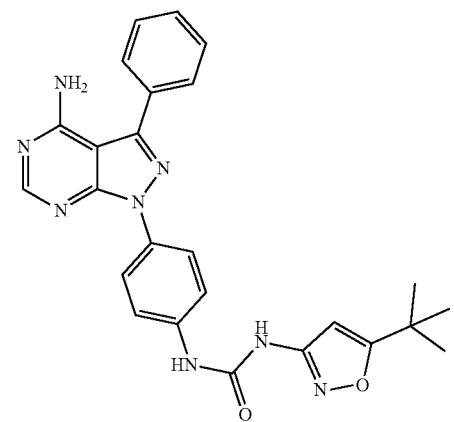
Compound 19
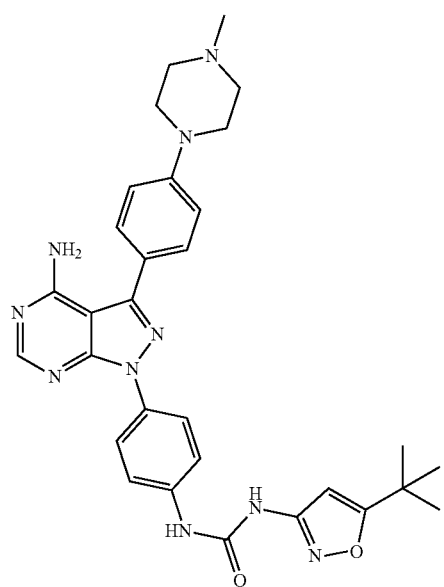
Compound 20
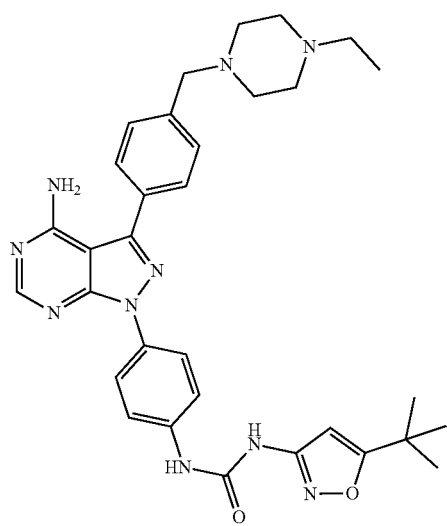
Compound 21
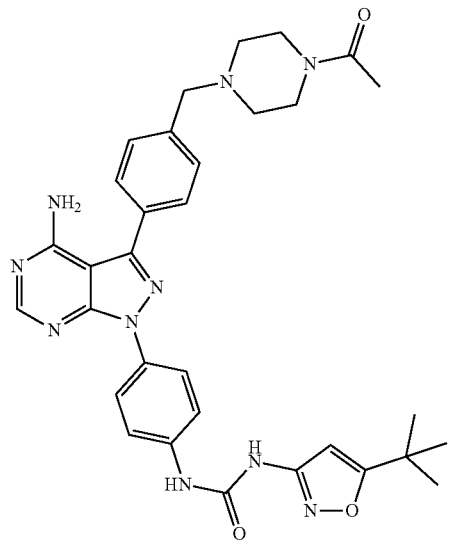
Compound 22
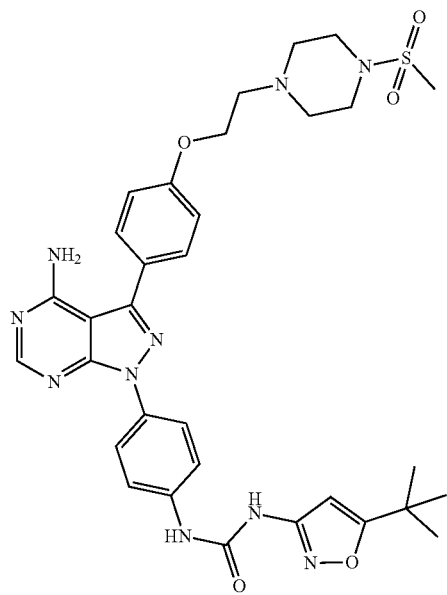

Compound 23
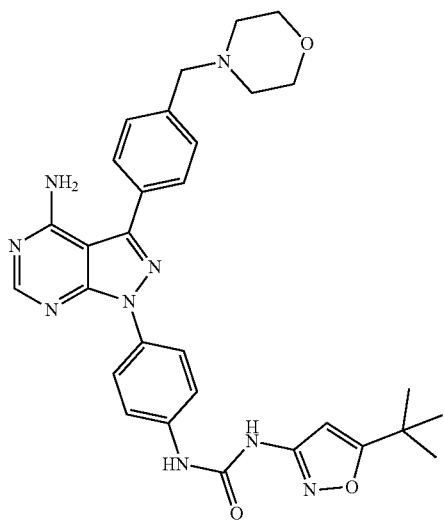
Compound 24
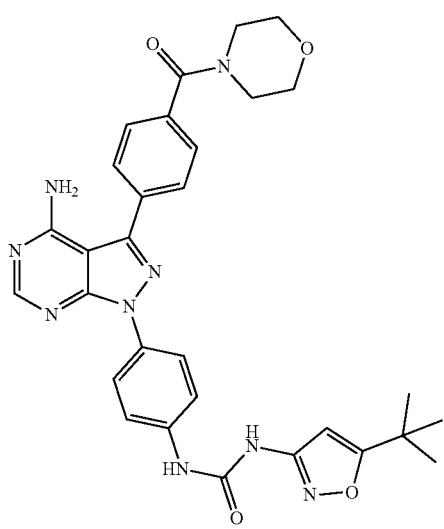
Compound 25
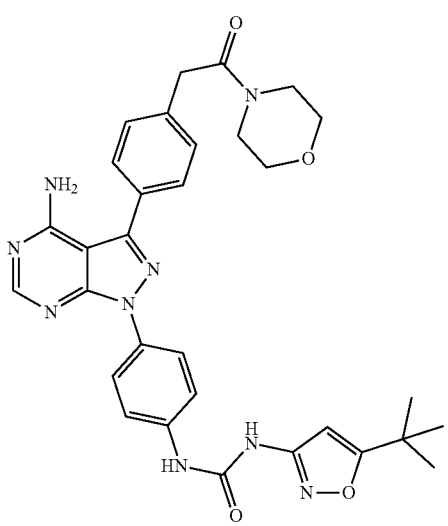
Compound 26
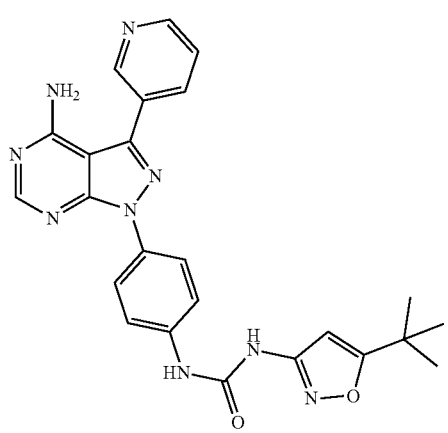
Compound 27
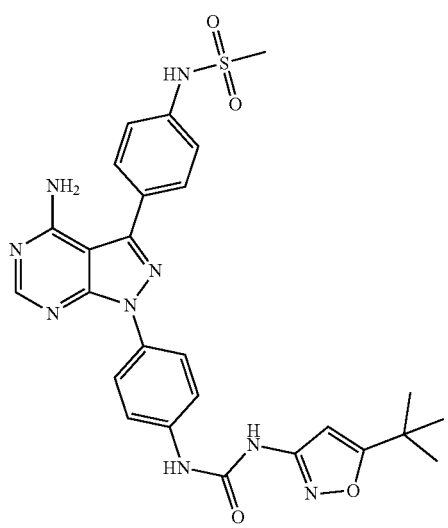
Compound 28
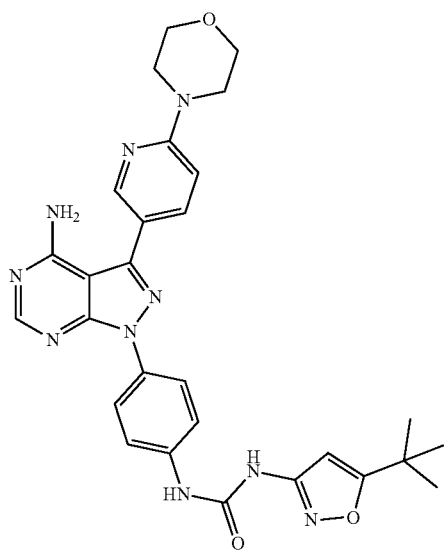

Compound 29
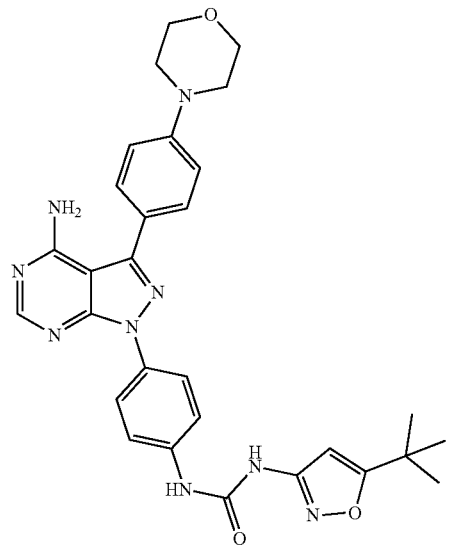
Compound 30
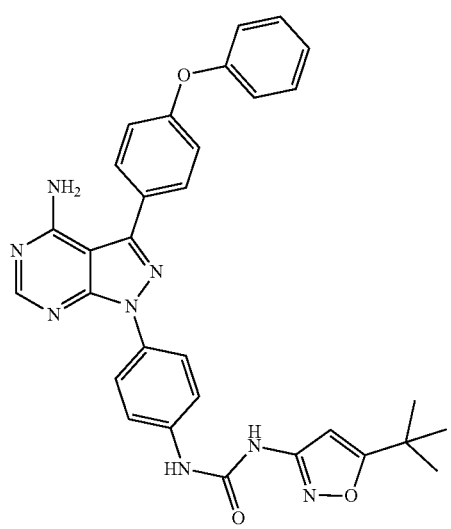
Compound 31
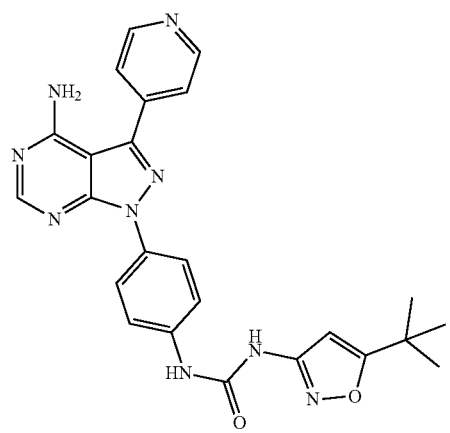
Compound 32
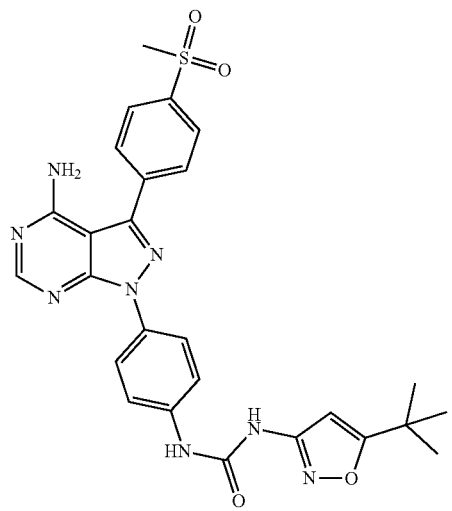
Compound 33
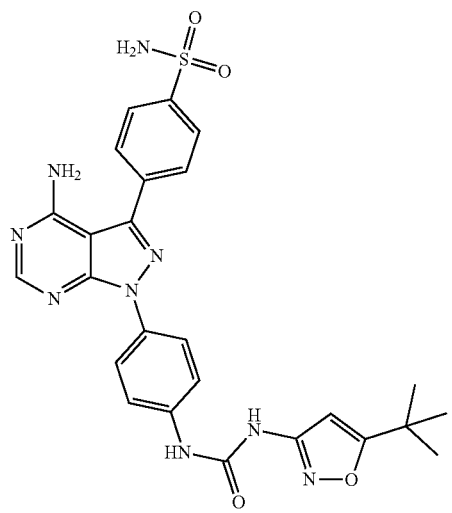
Compound 34
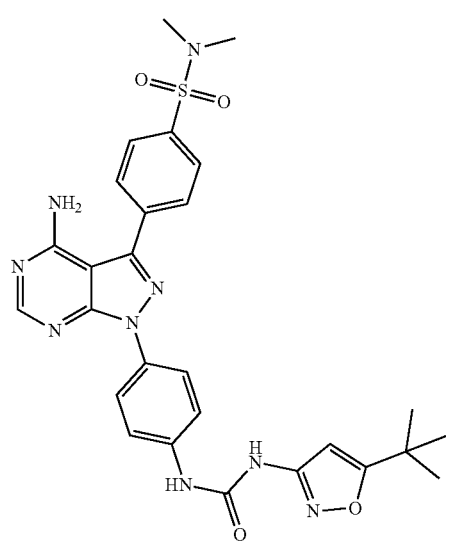

Compound 35
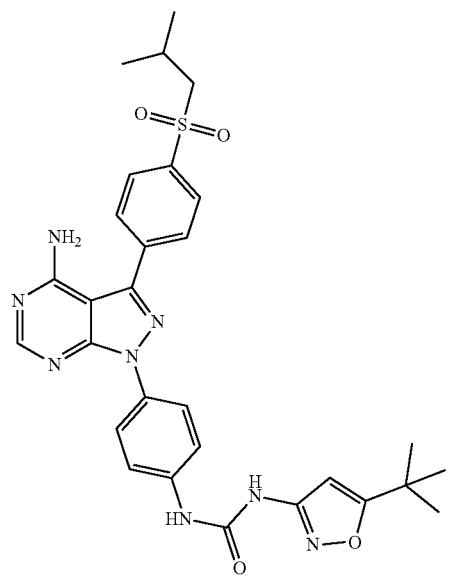
Compound 37
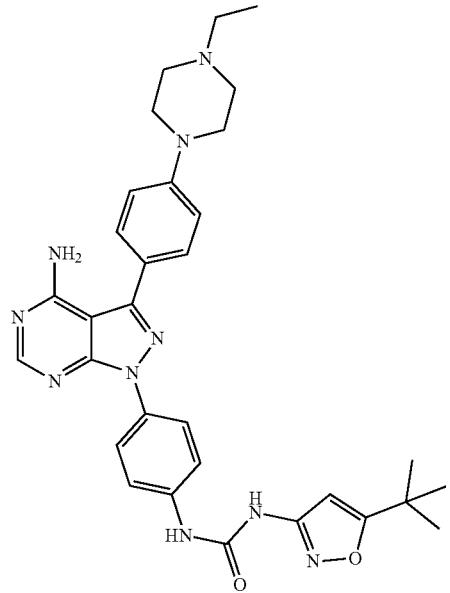
Compound 36
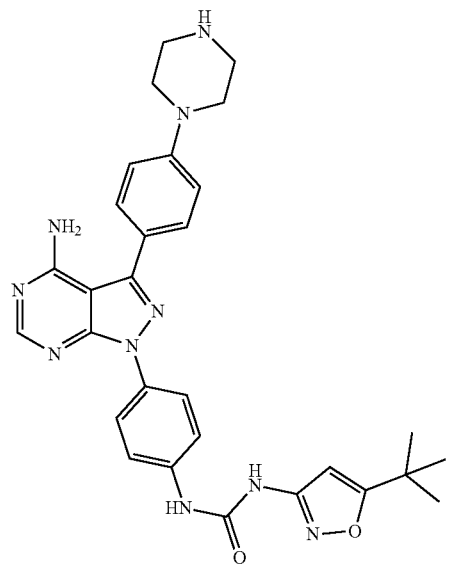
Compound 38
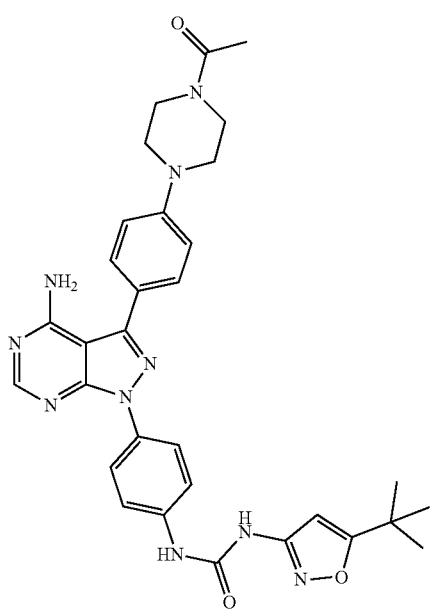

-continued
Compound 39
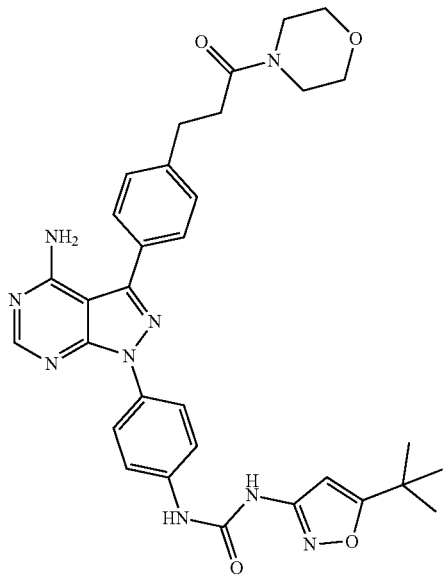
Compound 40
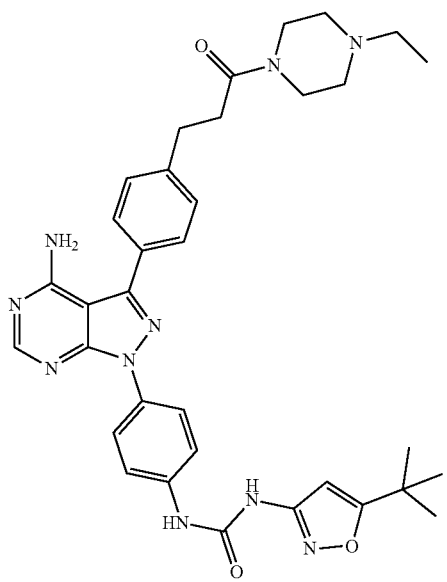
-continued
Compound 41
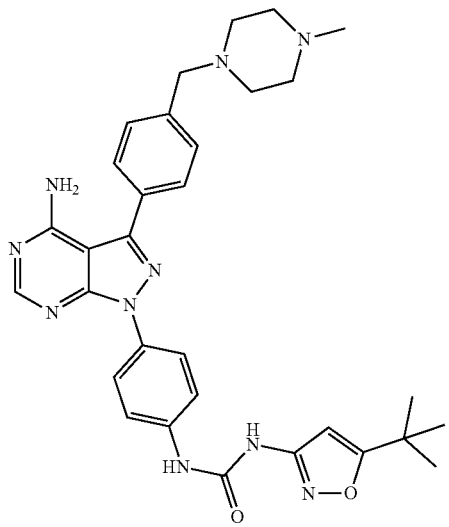
Compound 42
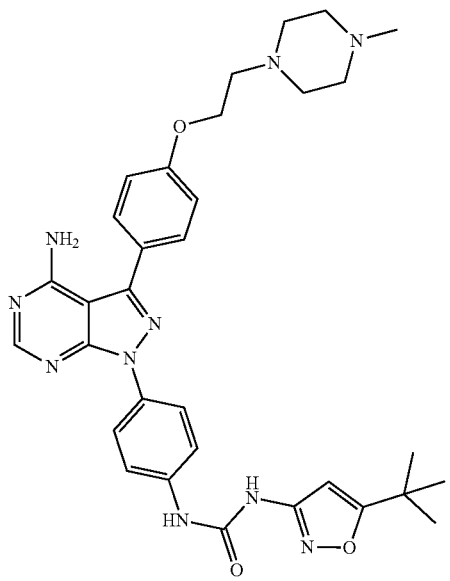

Compound 43
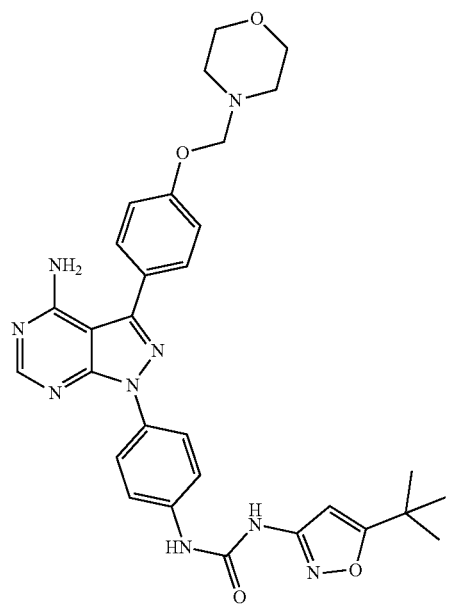
Compound 44
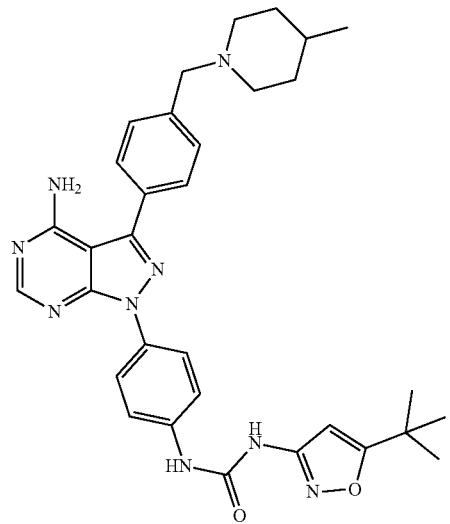
Compound 45
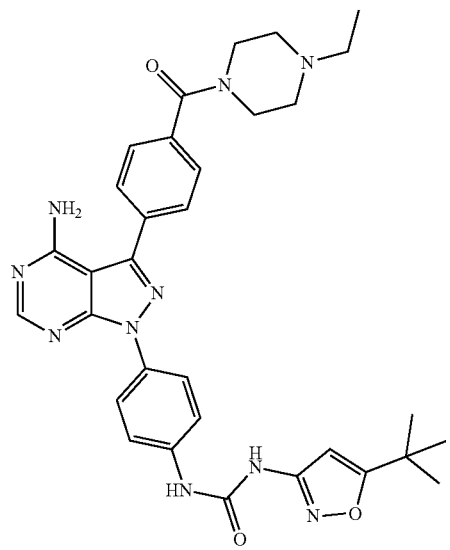
Compound 46
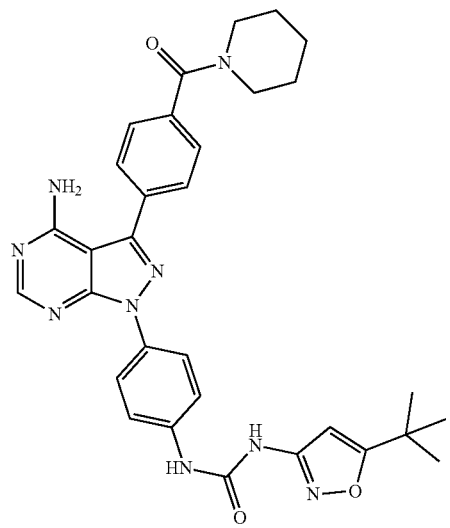

Compound 47
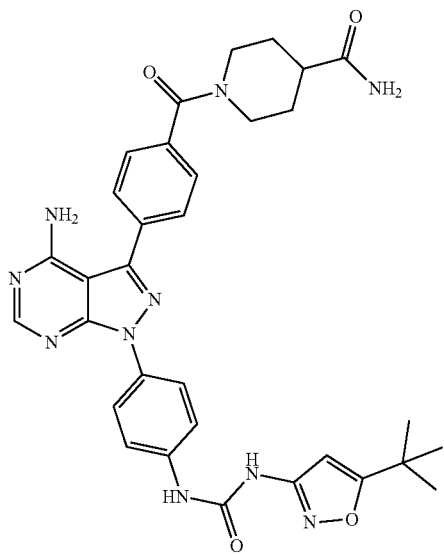
Compound 48
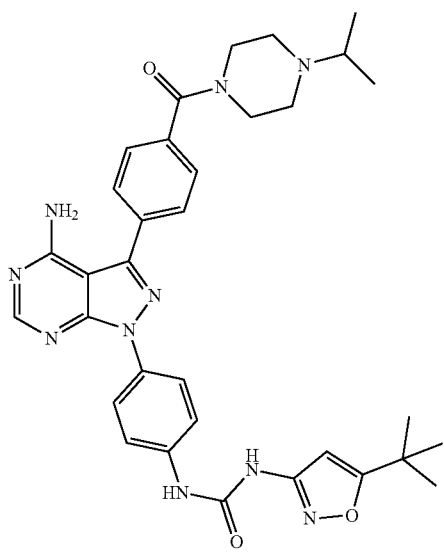
Compound 49
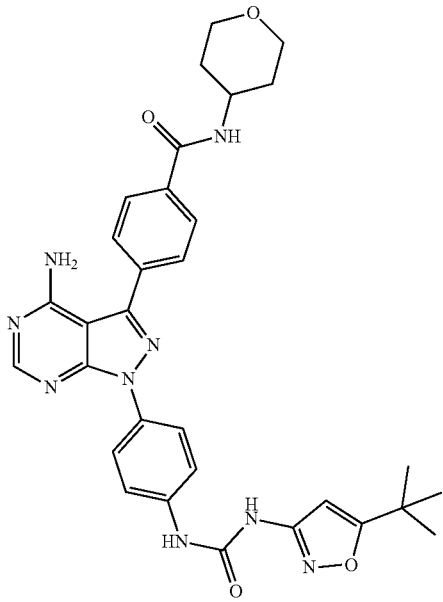
Compound 50
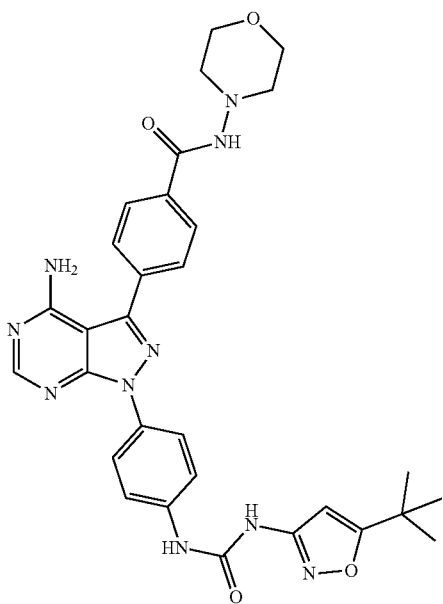

Compound 51
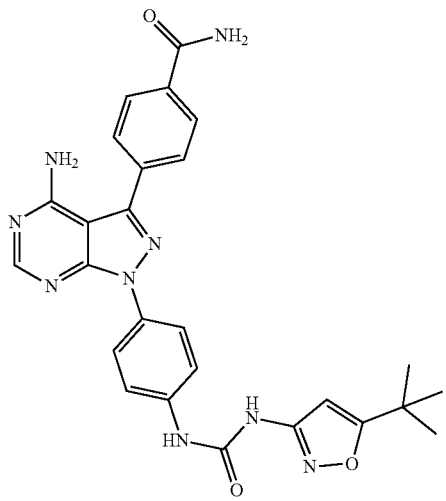
Compound 52
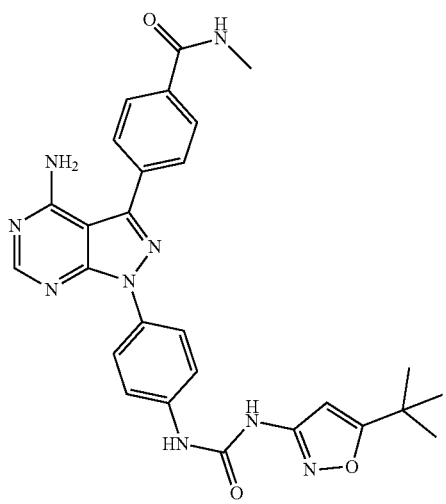
Compound 53
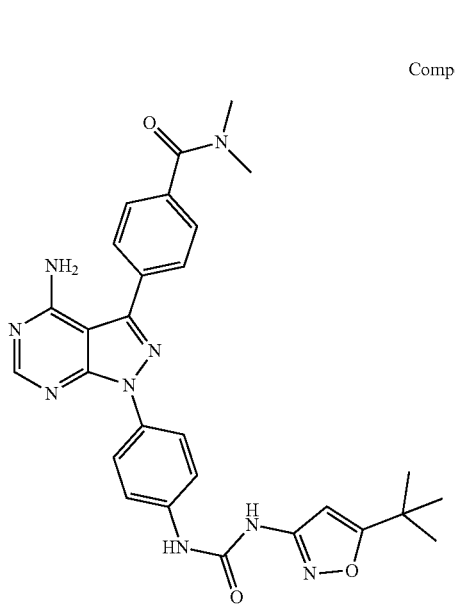
Compound 54
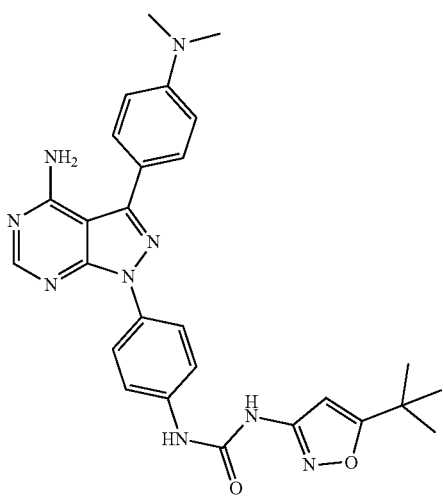
Compound 55
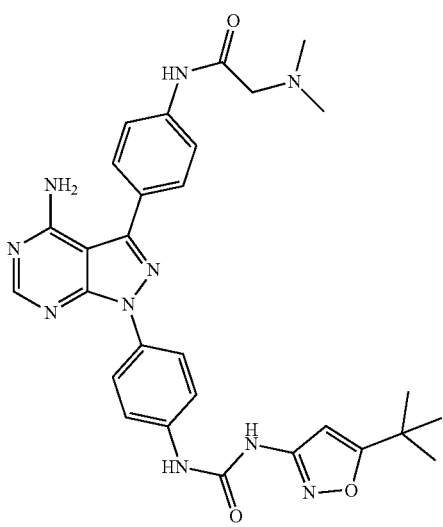
Compound 56
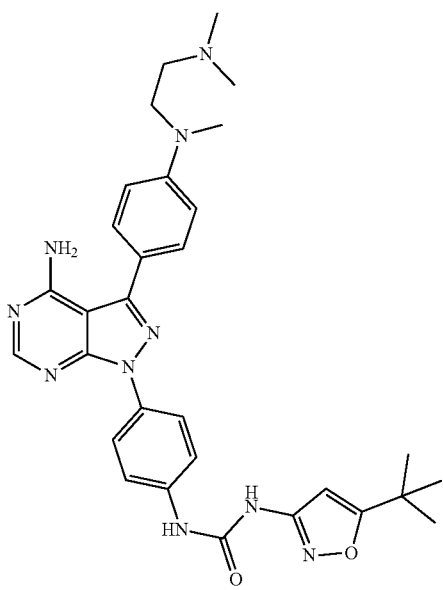

123
-continued
Compound 57
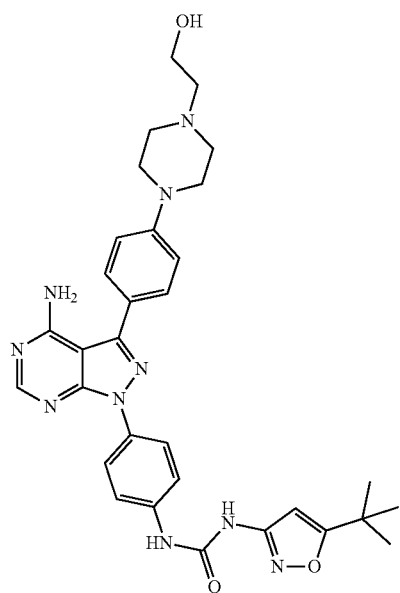
Compound 58
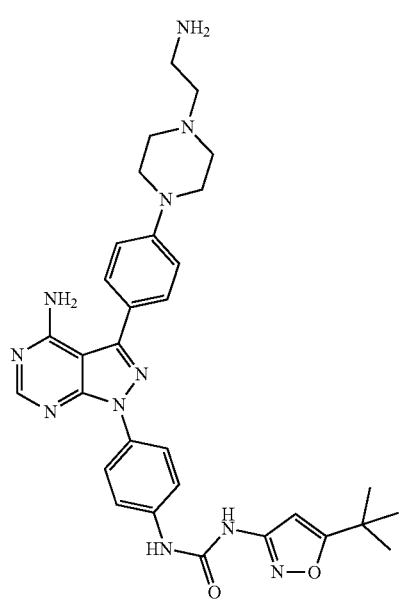
124
-continued
Compound 59
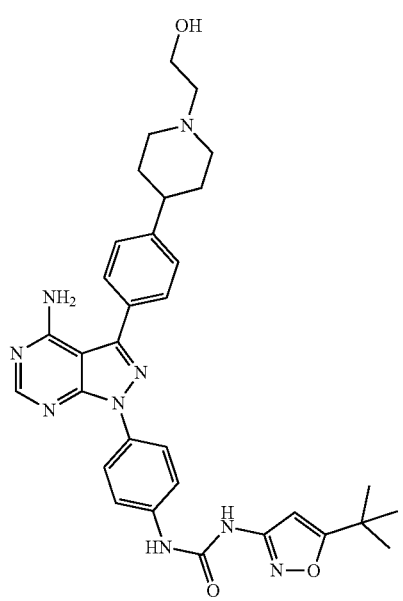
Compound 60
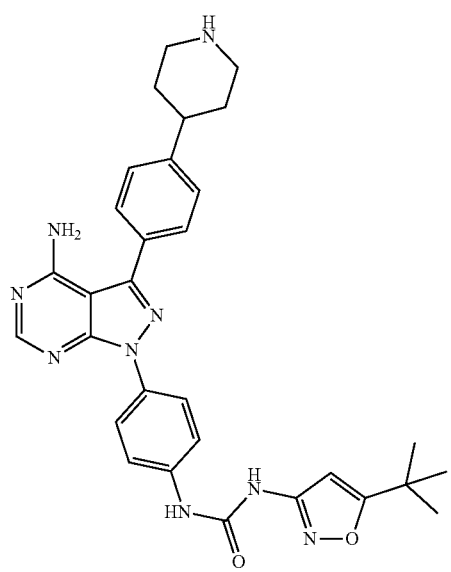

Compound 61
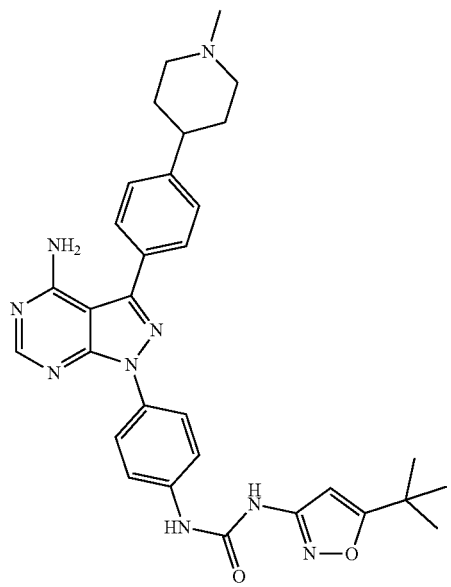
Compound 62
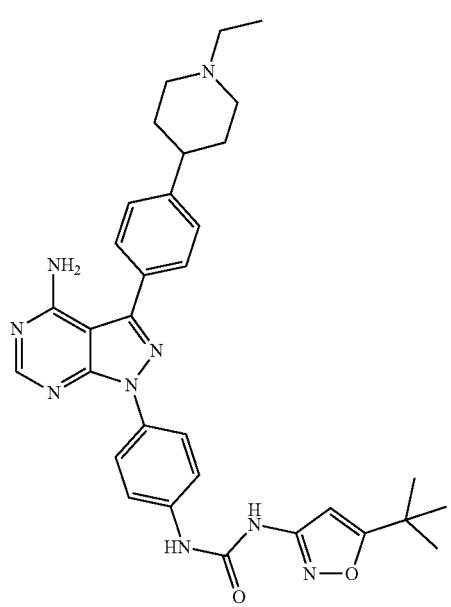
Compound 63
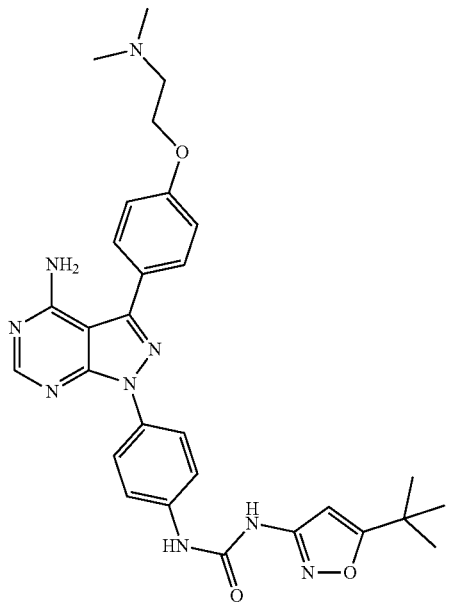
Compound 64
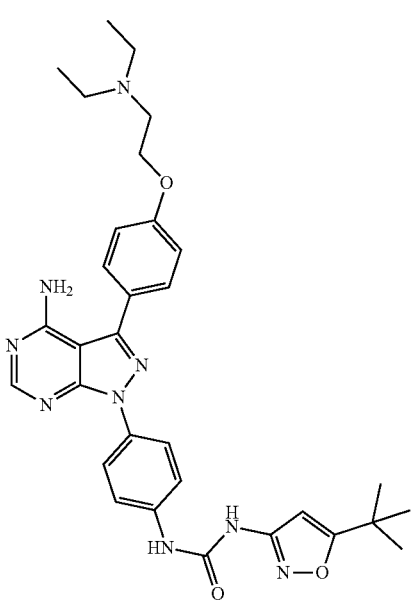

Compound 65

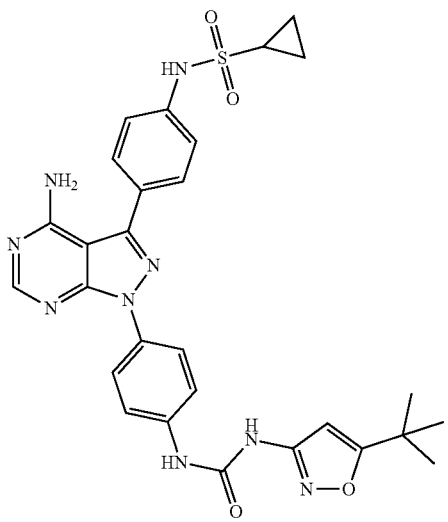

Compound 66

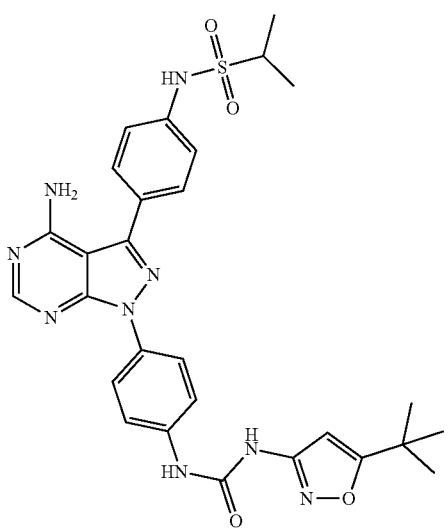

Compound 67

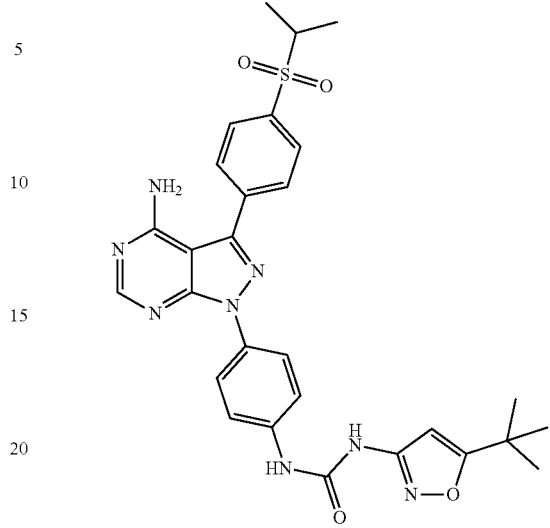

Compound 68

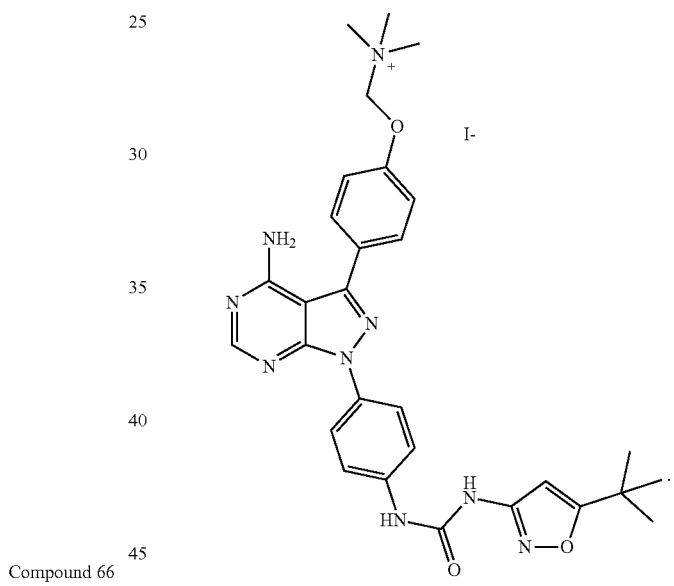

10. A pharmaceutical composition, comprising the compound or a pharmaceutically acceptable salt, solvate, enantiomer, or diastereomer thereof according to claim 1, a pharmaceutically acceptable carrier or excipient, and optionally other therapeutic agents.

11. A method for reducing or inhibiting the activity of wild-type FLT3 kinase 1 and/or mutant FLT3 kinase in a cell or a subject, wherein the method comprises administrating the compound according to claim 1 to a subject.

12. The method according to claim 11, wherein the subject has developed drug resistance due to over-expression of FL ligand, or the cell over-expresses FL ligand or the cell is in a FL ligand-overexpressing environment.

13. The method according to claim 11, wherein the subject or the cell expresses one or more of mutant kinases FLT3/ITD, FLT3/835Y, FLT3/F691L, FLT3/K663Q, FLT3/D835V and FLT3/D835H.

14. The method according to claim 11, wherein the subject is an acute myeloid leukemia patient, or the cell is acute myeloid leukemia cell.

* * * * *